US010731215B2

(12) United States Patent
Ballhause et al.

(10) Patent No.: US 10,731,215 B2
(45) Date of Patent: Aug. 4, 2020

(54) METHOD FOR DETERMINING THE PRESENCE OR ABSENCE OF METHYLATION IN A SAMPLE

(75) Inventors: Matthias Ballhause, Berlin (DE); Kurt Berlin, Stahnsdorf (DE); Theo De Vos, Seattle, WA (US); Dimo Dietrich, Berlin (DE); Volker Liebenberg, Berlin (DE); Catherine Lofton-Day, Seattle, WA (US); Joe Lograsso, Seattle, WA (US); Jennifer Maas, Seattle, WA (US); Fabian Model, Berlin (DE); Matthias Schuster, Berlin (DE); Andrew Z. Sledziewski, Shoreline, WA (US); Reimo Tetzner, Berlin (DE)

(73) Assignee: EPIGENOMICS AG, Berlin (DE)

( * ) Notice: Subject to any disclaimer, the term of this patent is extended or adjusted under 35 U.S.C. 154(b) by 1277 days.

(21) Appl. No.: 11/910,887

(22) PCT Filed: Apr. 17, 2006

(86) PCT No.: PCT/US2006/014667
§ 371 (c)(1),
(2), (4) Date: Nov. 21, 2007

(87) PCT Pub. No.: WO2006/113770
PCT Pub. Date: Oct. 26, 2006

(65) Prior Publication Data
US 2011/0059432 A1 Mar. 10, 2011

Related U.S. Application Data

(60) Provisional application No. 60/672,242, filed on Apr. 15, 2005, provisional application No. 60/780,248, filed on Mar. 8, 2006, provisional application No. 60/723,602, filed on Oct. 4, 2005, provisional application No. 60/697,521, filed on Jul. 8, 2005, provisional application No. 60/676,997, filed on May 2, 2005.

(51) Int. Cl.
*C12Q 1/68* (2018.01)
*C12Q 1/6883* (2018.01)
*C12N 15/10* (2006.01)
*C12Q 1/6806* (2018.01)
*C07H 21/04* (2006.01)

(52) U.S. Cl.
CPC ....... *C12Q 1/6883* (2013.01); *C12N 15/1003* (2013.01); *C12Q 1/6806* (2013.01); *C12Q 2523/125* (2013.01); *C12Q 2600/154* (2013.01); *Y10T 436/143333* (2015.01)

(58) Field of Classification Search
None
See application file for complete search history.

(56) References Cited

U.S. PATENT DOCUMENTS

| 5,532,127 | A | * | 7/1996 | Gallatin | ........... C07K 14/70525 435/6.16 |
| 5,565,332 | A | * | 10/1996 | Hoogenboom | ........ C07K 16/18 435/235.1 |
| 5,786,146 | A | * | 7/1998 | Herman | ............... C12Q 1/6827 435/6.12 |
| 6,124,120 | A | | 9/2000 | Lizardi | |
| 6,251,594 | B1 | | 6/2001 | Gonzalgo et al. | |
| 6,326,145 | B1 | | 12/2001 | Whitcombe et al. | |
| 6,365,729 | B1 | | 4/2002 | Tyagi et al. | |
| 6,410,725 | B1 | * | 6/2002 | Scholl | ................ C12N 15/1003 536/25.41 |
| 6,709,818 | B1 | * | 3/2004 | Nelson | ................. C12Q 1/6886 435/6.14 |
| 6,803,216 | B2 | * | 10/2004 | Hogrefe | ............... C12N 15/102 435/91.2 |
| 6,818,404 | B2 | * | 11/2004 | Shuber | ............................. 435/6 |
| 6,858,388 | B2 | * | 2/2005 | Markowitz et al. | ......... 435/6.14 |
| 6,927,028 | B2 | | 8/2005 | Dennis et al. | |

(Continued)

FOREIGN PATENT DOCUMENTS

| DE | 10013847 | 9/2001 |
| DE | 10019173 | 10/2001 |

(Continued)

OTHER PUBLICATIONS

"Mammal," (Wikipedia.com; accessed Sep. 22, 2011).*
"Murinae," (Wikipedia.com, accessed Mar. 18, 2013).*
"Human Hybrids," by Michael F. Hammer, Scientific American, May 2013, pp. 66-71.*
"List of sequenced animal genomes," Wikipedia.com, accessed Jan. 19, 2018. (Year: 2018).*
"Human Hybrids," Michael F. Hammer, Scientific American, May 2013, pp. 66-71. (Year: 2013).*
Frommer et al., "A genomic sequencing protocol that yields a positive display of 5-methylcytosine residues in individual DNA strands" Proceedings of the National Academy of Sciences, USA, vol. 89, Mar. 1992, pp. 1827-1831. (Year: 1992).*

(Continued)

*Primary Examiner* — Bradley L. Sisson
(74) *Attorney, Agent, or Firm* — Lathrop GPM LLP; James H. Velema, Esq.; Sean M. Coughlin, Esq.

(57) ABSTRACT

Aspects of the present invention relate to compositions and methods for providing DNA fragments from a remote sample. In particular aspects a remote sample comprising DNA is provided, DNA is isolated from the remote sample, and the isolated DNA is treated in a way which allows differentiation of methylated and unmethylated cytosine. Additional, particular embodiments provide compositions and methods for methylation analysis of DNA derived from a remote sample. Other aspects provide for compositions and methods of whole genome amplification of bisulfite treated DNA. Other aspects provide methods for determining the presence or absence of methylation of at least one cytosine, or a series of cytosines in cis, in human DNA of a blood sample, a plasma sample, a serum sample or a urine sample from a human individual.

8 Claims, 2 Drawing Sheets

Specification includes a Sequence Listing.

(56) References Cited

U.S. PATENT DOCUMENTS

| | | | |
|---|---|---|---|
| 7,118,868 B2 | 10/2006 | Berlin | |
| 7,195,870 B2 | 3/2007 | Olek et al. | |
| 2003/0068620 A1* | 4/2003 | Markowitz | C12Q 1/6827 435/6.14 |
| 2003/0087240 A1 | 5/2003 | Whitcombe et al. | |
| 2003/0143606 A1 | 7/2003 | Olek et al. | |
| 2004/0038245 A1 | 2/2004 | Belinsky et al. | |
| 2004/0142334 A1* | 7/2004 | Schacht | C12Q 1/6883 435/6.14 |
| 2005/0069879 A1 | 3/2005 | Berlin | |
| 2006/0223197 A1* | 10/2006 | Vielsack | 436/524 |
| 2006/0234234 A1* | 10/2006 | Van Dongen et al. | 435/6 |
| 2006/0246453 A1* | 11/2006 | Kato et al. | 435/6 |
| 2013/0035248 A1* | 2/2013 | Icenhour | 506/9 |
| 2013/0040344 A1* | 2/2013 | Ju | 435/91.21 |
| 2013/0040843 A1* | 2/2013 | Von Toerne et al. | 506/9 |
| 2013/0040847 A1* | 2/2013 | Thrippleton et al. | 506/9 |

FOREIGN PATENT DOCUMENTS

| | | |
|---|---|---|
| DE | 10019058 | 12/2001 |
| DE | 10032529 | 2/2002 |
| DE | 10037769 | 2/2002 |
| DE | 10043826 | 3/2002 |
| DE | 10054972 | 6/2002 |
| DE | 10054974 | 6/2002 |
| DE | 10061338 | 6/2002 |
| DE | 10164501 | 6/2003 |
| DE | 20121966 | 11/2003 |
| DE | 20121961 | 12/2003 |
| DE | 20121963 | 12/2003 |
| DE | 20121965 | 12/2003 |
| DE | 20121967 | 12/2003 |
| DE | 20121968 | 12/2003 |
| DE | 20121969 | 12/2003 |
| DE | 20121970 | 12/2003 |
| DE | 20121971 | 12/2003 |
| DE | 20121972 | 12/2003 |
| DE | 20121973 | 12/2003 |
| DE | 20121974 | 12/2003 |
| DE | 20121977 | 12/2003 |
| DE | 20121979 | 12/2003 |
| DE | 20121960 | 1/2004 |
| DE | 20121964 | 1/2004 |
| DE | 20121975 | 1/2004 |
| DE | 20121978 | 1/2004 |
| DE | 10230692 | 2/2004 |
| DE | 10255104 | 3/2004 |
| DE | 10245779 | 4/2004 |
| EP | 1340818 | 9/2003 |
| EP | 1369493 | 12/2003 |
| EP | 1478784 | 11/2004 |
| EP | 1609873 | 12/2005 |
| WO | WO 99/28498 | 6/1999 |
| WO | WO 01/38565 | 5/2001 |
| WO | WO 01/62064 | 8/2001 |
| WO | WO 01/62960 | 8/2001 |
| WO | WO 01/62961 | 8/2001 |
| WO | WO 01/68912 | 9/2001 |
| WO | WO 02/18632 | 3/2002 |
| WO | WO 02/18649 | 3/2002 |
| WO | WO 02/072880 | 9/2002 |
| WO | WO 02/077272 | 10/2002 |
| WO | WO 02/103042 | 12/2002 |
| WO | WO 03/014388 | 2/2003 |
| WO | WO 03/027259 | 4/2003 |
| WO | WO 03/044226 | 5/2003 |
| WO | WO 03/052135 | 6/2003 |
| WO | WO 03/064700 | 8/2003 |
| WO | WO 03/085132 | 10/2003 |
| WO | WO 2004/035803 | 4/2004 |
| WO | WO 2004/051224 | 6/2004 |
| WO | WO 2004-051224 | 6/2004 |
| WO | WO 2005/001141 | 1/2005 |
| WO | WO 2005/024056 | 3/2005 |
| WO | WO 2005/038051 | 4/2005 |

OTHER PUBLICATIONS

Cheung et al., "Whole genome amplification using a degenerate oligonucleotide primer allows hundreds of genotypes to be performed on less than one nanogram of genomic DNA," Proceedings of the National Academy of Sciences, Dec. 1996, pp. 14676-14679, vol. 93.

Cottrell et al., "A real-time PCR assay for DNA-methylation using methylation-specific blockers," Nucleic Acids Research, 2004, p. e10, vol. 32, No. 1.

Dean et al., "Comprehensive human genome amplification using multiple displacement amplification," Proceedings of the National Academy of Sciences, Apr. 16, 2002, pp. 5261-5266, vol. 99, No. 8.

Diehl et al., "Detection and quantification of mutations in the plasma of patients with colorectal tumors," Proceedings of the National Academy of Sciences, Nov. 8, 2005, pp. 16368-16373, vol. 102, No. 45.

Eads et al., "CpG Island Hypermethylation in Human Colorectal Tumors Is Not Associated with DNA Methyltransferase Overexpression," Cancer Research, May 15, 1999, pp. 2302-2306, vol. 59.

Frommer et al., "A genomic sequencing protocol that yields a positive display of 5-methylcytosine residues in individual DNA strands," Proceedings of the National Academy of Sciences, Mar. 1992, pp. 1827-1831, vol. 89.

Gardiner-Garden et al., "CpG Islands in Vertebrate Genomes," Journal of Molecular Biology, 1987, pp. 261-282, vol. 196.

Gonzalgo et al., Rapid quantitation of methylation differences at specific sites using methylation-sensitive single nucleotide primer extension (Ms-SnuPE), Nucleic Acids Research, 1997, pp. 2529-2531, vol. 25, No. 12.

Grunau et al., "Bisulfite genomic sequencing: systematic investigation of critical experimental parameters," Nucleic Acids Research, 2001, p. e65, vol. 29, No. 13.

Hawkins et al., "Whole genome amplification—applications and advances," Current Opinion in Biotechnology, 2002, pp. 65-67, vol. 13, No. 1.

Herman et al., "Methylation-specific PCR: A novel PCR assay for methylation status of CpG islands," Proceedings of the National Academy of Sciences, Sep. 1996, pp. 9821-9826, vol. 93.

Lecomte et al., "Detection of Free-Circulating Tumor-Associated DNA in Plasma of Colorectal Cancer Patients and Its Association With Prognosis," International Journal of Cancer, 2002, pp. 542-548, vol. 100.

Li et al., "Whole Genome Amplification of Plasma-Circulating DNA Enables Expanded Screening for Allelic Imbalance in Plasma," Journal of Molecular Diagnostics, Feb. 2006, pp. 22-30, vol. 8, No. 1.

Rand et al., "Headloop suppression PCR and its application to selective amplification of methylated DNA sequences," Nucleic Acids Research, 2005, p. e127, vol. 33, No. 14.

Sadri et al., "Rapid analysis of DNA methylation using new restriction enzyme sites created by bisulfite modification," Nucleic Acids Research, 1996, p. 5058-5059, vol. 24, No. 24.

Solinas et al., "Duplex Scorpion primers in SNP analysis and FRET applications," Nucleic Acids Research, 2001, p. e96, vol. 29, No. 20.

Telenius et al., "Degenerate Oligonucleotide-Primed PCR: General Amplification of Target DNA by a Single Degenerate Primer," Genomics, 1992, pp. 718-725, vol. 13.

Thelwell et al., "Mode of action and application of Scorpion primers to mutation detection," Nucleic Acids Research, 2000, pp. 3752-3761, vol. 28, No. 19.

Tyagi et al., "Molecular Beacons: Probes that Fluoresce upon Hybridization," Nature Biotechnology, Mar. 1996, pp. 303-308, vol. 14.

Utting et al., "*Advances in Brief* Microsatellite Analysis of Free Tumor DNA in Urine, Serum, and Plasma of Patients: A Minimally

(56) References Cited

OTHER PUBLICATIONS

Invasive Method for the Detection of Bladder Cancer," Clinical Cancer Research, Jan. 2002, pp. 35-40, vol. 8, No. 35-40.

Whitcombe et al., "Detection of PCR products using self-probing amplicons and fluorescence," Nature Biotechnology, Aug. 1999, pp. 804-807, vol. 17.

Wong et al., "Quantitative Analysis of Tumor-derived Methylated p16INK4a Sequences in Plasma, Serum, and Blood Cells of Hepatocellular Carcinoma Patents," Clinical Cancer Research, Mar. 2003, pp. 1047-1052, vol. 9.

Xiong et al., "COBRA: a sensitive and quantitative DNA methylation assay," Nucleic Acids Research, 1997, pp. 2532-2534, vol. 25, No. 12.

Zhang et al., "Whole genome amplification from a single cell: Implications for genetic analysis," Proceedings of the National Academy of Sciences, Jul. 1992, pp. 5847-5851, vol. 89.

Wong et al., "Detection of Aberrant p16 Methylation in the Plasma and Serum of Liver Cancer Patients," Cancer Research, 1999, pp. 71-73, vol. 59.

Wong, Ivy H. N. et al.: "*Quantitative Analysis of Tumor-derived Methylated p96INK4a Sequences in Plasma, Serum, and Blood Cells of Hepatocellular Carcinoma Patients*", Clinical Cancer Research; Mar. 2003, vol. 9, pp. 1047-1052.

Clark et al. (1994) "High Sensitivity Mapping of Methylated Cytosines," Nucleic Acids Research. 22(15):2990-2997.

Hashimoto et al. (2007) "Improved Quantification of DNA Methylation Using Methylation-Sensitive Restriction Enzymes and Real-Time PCR," Epigenetics. 2(2):86-95.

Ruike et al. (2010) "Genome-wide analysis of aberrant methylation in human breast cancer cells using methyl-DNA immunoprecipitation combined with high-throughput sequencing," BMC Genomics. 11:137. pp. 1-11.

National Human Genome Research Institute (Oct. 30, 2010) "The Human Genome Project Completion: Frequently Asked Questions," National Institutes of Health. Accessible on the Internet at URL: https://www.genome.gov/11006943/human-genome-project-completion-frequently-asked-questions/. [Last Accessed Nov. 10, 2016].

Pearson (2006) "Human Genome Complete (Again)," Nature News. Macmillan Publishers Limited. Accessible on the Internet at URL: http://www.nature.com/news/2006/060515/full/news060515-12.html. [Last Accessed Nov. 10, 2016].

Venter et al. (2001) "The Sequence of the Human Genome," Science. 291(5507):1304-1351.

* cited by examiner

SEQUENCE LISTING

<160> NUMBER OF SEQ ID NOS: 15

<210> SEQ ID NO 1
<211> LENGTH: 25
<212> TYPE: DNA
<213> ORGANISM: Artificial Sequence
<220> FEATURE:
<223> OTHER INFORMATION: CFF1 forward primer

<400> SEQUENCE: 1
taagagtaat aatggatgga tgatg                                    25

<210> SEQ ID NO 2
<211> LENGTH: 17
<212> TYPE: DNA
<213> ORGANISM: Artificial Sequence
<220> FEATURE:
<223> OTHER INFORMATION: CFF1 reverse primer

<400> SEQUENCE: 2
cctcccatct cccttcc                                             17

<210> SEQ ID NO 3
<211> LENGTH: 25
<212> TYPE: DNA
<213> ORGANISM: Artificial Sequence
<220> FEATURE:
<223> OTHER INFORMATION: CFF1 TaqMan Probe

<400> SEQUENCE: 3
atggatgaag aaagaaagga tgagt                                    25

<210> SEQ ID NO 4
<211> LENGTH: 25
<212> TYPE: DNA
<213> ORGANISM: Artificial Sequence
<220> FEATURE:
<223> OTHER INFORMATION: HB14 forward primer

<400> SEQUENCE: 4
tggtgatgga ggaggtttag taagt                                    25

<210> SEQ ID NO 5
<211> LENGTH: 27
<212> TYPE: DNA
<213> ORGANISM: Artificial Sequence
<220> FEATURE:
<223> OTHER INFORMATION: HB14 reverse primer

<400> SEQUENCE: 5
aaccaataaa acctactcct cccttaa                                  27

<210> SEQ ID NO 6
<211> LENGTH: 30
<212> TYPE: DNA
<213> ORGANISM: Artificial Sequence
<220> FEATURE:
<223> OTHER INFORMATION: HB14 TaqMan probe

<400> SEQUENCE: 6
accaccaccc aacacacaat aacaaacaca                                     30

<210> SEQ ID NO 7
<211> LENGTH: 27
<212> TYPE: DNA
<213> ORGANISM: Artificial Sequence
<220> FEATURE:
<223> OTHER INFORMATION: GSTP1 TaqMan probe 1

<400> SEQUENCE: 7
gtttaaggtt aagtttgggt gtttgta                                        27

<210> SEQ ID NO 8
<211> LENGTH: 29
<212> TYPE: DNA
<213> ORGANISM: Artificial Sequence
<220> FEATURE:
<223> OTHER INFORMATION: GSTP1 TaqMan probe 2

<400> SEQUENCE: 8
ttttgttttg tgttaggttg tttttagg                                       29

<210> SEQ ID NO 9
<211> LENGTH: 20
<212> TYPE: DNA
<213> ORGANISM: Artificial Sequence
<220> FEATURE:
<223> OTHER INFORMATION: GSTP1 forward primer

<400> SEQUENCE: 9
ggagtggagg aaattgagat                                                20

<210> SEQ ID NO 10
<211> LENGTH: 22
<212> TYPE: DNA
<213> ORGANISM: Artificial Sequence
<220> FEATURE:
<223> OTHER INFORMATION: GSTP1 reverse primer

<400> SEQUENCE: 10
ccacacaaca aatactcaaa ac                                             22

<210> SEQ ID NO 11
<211> LENGTH: 25
<212> TYPE: DNA
<213> ORGANISM: Artificial Sequence
<220> FEATURE:
<223> OTHER INFORMATION: HM 17378.71LC TaqMan probe 1

<400> SEQUENCE: 11
gttcgaaatg attttattta gttgc                                          25

<210> SEQ ID NO 12
<211> LENGTH: 17
<212> TYPE: DNA
<213> ORGANISM: Artificial Sequence
<220> FEATURE:

```
<223> OTHER INFORMATION: HM 17378.71LC TaqMan probe 2

<400> SEQUENCE: 12
cgttgatcgc ggggttc                                                  17

<210> SEQ ID NO 13
<211> LENGTH: 26
<212> TYPE: DNA
<213> ORGANISM: Artificial Sequence
<220> FEATURE:
<223> OTHER INFORMATION: HM 17378.71LC  forward primer

<400> SEQUENCE: 13
gtagtagtta gtttagtatt tatttt                                        26

<210> SEQ ID NO 14
<211> LENGTH: 17
<212> TYPE: DNA
<213> ORGANISM: Artificial Sequence
<220> FEATURE:
<223> OTHER INFORMATION: HM 17378.71LC  reverse primer

<400> SEQUENCE: 14
cccaccaacc atcatat                                                  17

<210> SEQ ID NO 15
<211> LENGTH: 32
<212> TYPE: DNA
<213> ORGANISM: Artificial Sequence
<220> FEATURE:
<223> OTHER INFORMATION: HM 17378.71LC  blocker oligo

<400> SEQUENCE: 15
catcatatca aaccccacaa tcaacacaca ac                                 32
```

METHOD FOR DETERMINING THE PRESENCE OR ABSENCE OF METHYLATION IN A SAMPLE

CROSS-REFERENCE TO RELATED APPLICATIONS

The present application is a 35 U.S.C. § 371 filing of International Patent Application No. PCT/US2006/014667, filed 17 Apr. 2006, which claims the benefit of priority to U.S. Provisional Patent Application Nos.: 60/672,242, filed 15 Apr. 2005; 60/676,997, filed 2 May 2005; 60/697,521, filed 8 Jul. 2005; 60/723,602, filed 4 Oct. 2005; and 60/780,248, filed 8 Mar. 2006; all of which are incorporated by reference herein in their entireties.

FIELD OF THE INVENTION

The invention relates generally to novel and substantially improved compositions and methods for providing DNA fragments derived from a remote sample, and for analyses of same.

SEQUENCE LISTING

A Sequence Listing, comprising SEQ ID NOS: 1-15, in paper form is included and attached hereto as part of this application.

BACKGROUND OF ASPECTS OF THE INVENTION

Development of a Medical Test.

The probability of curing a disease (e.g. a cancer disease) is many times predominantly dependent from an early as possible detection of the disease. It is also often advantageous to detect a predisposition for a disease or if for example the disease is already advanced to make an estimation for the most promising treatment for the disease. Such an early as possible detection, prediction or estimation reduces the costs for direct and associated medical treatment. It ensures also a higher quality of life for the affected patient.

This leads to the situation that a lot of samples derived from individuals with a suspected disease have to be tested, the majority may not be affected by the disease. Or, in case of patients with a diagnosed disease, a lot of samples have to be tested, and only a small percentage will respond to a certain treatment.

In general, it is desirable that a test should have a high as possible sensitivity, a high as possible specificity and a high as possible accuracy. Sensitivity is a measure of a test's ability to correctly detect the target disease in an individual being tested. A test having poor sensitivity produces a high rate of false negatives, i.e., individuals who have the disease but are falsely identified as being free of that particular disease. The potential danger of a false negative is that the diseased individual will remain undiagnosed and untreated for some period of time, during which the disease may progress to a later stage wherein treatments, if any, may be less effective. Mathematical it can be described as: Sensitivity=TP/(TP+FN). Thereby TP represents a true positive result and FN a false negative result. A true positive result means that the test is positive and the condition is present while a false negative result is where the test is negative but the condition is not present.

An example of a test that has low sensitivity is a protein-based blood test for HIV. This type of test exhibits poor sensitivity because it fails to detect the presence of the virus until the disease is well established and the virus has invaded the bloodstream in substantial numbers. In contrast, an example of a test that has high sensitivity is viral-load detection using the polymerase chain reaction (PCR). High sensitivity is achieved because this type of test can detect very small quantities of the virus. High sensitivity is particularly important when the consequences of missing a diagnosis are high.

Specificity, on the other hand, is a measure of a test's ability to identify accurately patients who are free of the disease state. A test having poor specificity produces a high rate of false positives, i.e., individuals who are falsely identified as having the disease. A drawback of false positives is that they force patients to undergo unnecessary medical procedures or treatments with their attendant risks, emotional and financial stresses, and which could have adverse effects on the patient's health. A feature of diseases which makes it difficult to develop diagnostic tests with high specificity is that disease mechanisms, particularly in cancer, often involve a plurality of genes and proteins. Additionally, certain proteins may be elevated for reasons unrelated to a disease state. Mathematical specificity can be described as: Specificity=TN/(FP+TN). Thereby TN represents a true negative result and FP a false positive result. A true negative result is where the test is negative and the condition is not present. A false positive result is where the test is positive but the condition is not present.

An example of a test that has high specificity is a gene-based test that can detect a p53 mutation. Specificity is important when the cost or risk associated with further diagnostic procedures or further medical intervention are very high.

Accuracy is a measure of a test's ability on one hand to correctly detect the target disease in an individual being tested and simultaneously on the other to identify accurately patients who are free of the disease state. So accuracy describes a test's sensitivity and specificity simultaneously. Mathematical it is defined as: Accuracy=(TP+TN)/N, wherein TP represents true positive results, TN true negative results and N the number of patients tested.

In general, because of self-evident reasons, a test of choice would be further characterized by at least one of the following criteria, but of course preferably by all of them: (i) high degree of standardization, (ii) large capability for automatization, (iii) avoidance of cross-contaminations of samples, (iv) low handling effort, (v) low cost, (vi) ease of handling, (vii) high reproducibility, (viii) high reliability.

Of course, all of the above described specifications apply not only for the test itself. They also apply to the workflow from collecting a sample to the actual start of the test. In other words a suitable workflow should enable a test with said specifications.

Starting Material for a Test.

It is advantageous for a test with regard to cost reduction and to a high quality of life of the patient that it can be performed non-invasively. If this is not possible, it is desirably to perform it by invasive means which affect as less as possible the patient, which are easy to perform, which cause low costs or combinations thereof. Because of that, remote samples like for example blood, sputum, stool or body fluids are the starting material of choice for a test.

However, the use of remote samples is quite limited by the low amount of DNA, in particular by the low amount of DNA which originates by the diseased cell or tissue. Therefore the workflow from the sample collecting to the start of the test has to be characterized by high yields of DNA.

In most cases the DNA of interest is very diluted in the sample. Typically less than 1% is relevant for the test underlying question. This emphasis that a workflow for collecting, providing, and processing DNA prior the test has to be characterized by high yields of DNA.

A further difficulty, for the use of remote samples is that the samples can be contaminated by a large amount of cells and therewith DNA. The contamination is thereby completely unrelated to the question on which the test is based on. For example such contaminations are bacteria like E. Coli in stool samples or red blood cells in plasma or serum samples. These contaminations are especially critical if they are interfere with the detection of the DNA of interest or if they are present in large amounts. In last case, the percentage of the DNA of interest becomes so small that it can no more be detected. Because of that a workflow for collecting, providing and processing DNA prior a test has to be sure to efficiently remove such contaminations.

Furthermore, the DNA of interest might be partially degraded in a remote sample. This depends on the type of the remote sample and also on the way of collecting and handling the remote sample. A fragmentation of DNA in remote sample down to a fragment size of 100 bp and under it is possible. Therefore a workflow from collecting a sample to the start of a test should ensure that small DNA fragments as well as large DNA fragments are provided and that the DNA does not get further fragmented.

Numerous documents exist which address these problems. Exemplary only the following are cited herein: Diehl F., et al. (2005) PNAS 102(45), 16368-16373; and Li J., et al. (2006) Journal of Molecular Diagnostics, 8(1), 22-30.

Methylation Analysis.

As revealed in recent years, one of the most powerful and promising approaches for detecting a disease, the predisposition for a disease or for estimating a probable response with respect to a certain disease treatment is the methylation analysis of the patient's genomic DNA.

Many diseases, in particular cancer diseases, are accompanied by modified gene expression. This may be a mutation of the genes themselves, which leads to an expression of modified proteins or to an inhibition or over-expression of the proteins or enzymes. A modulation of the expression may however also occur by epigenetic modifications, in particular by changes in the DNA methylation pattern. Such epigenetic modifications do not affect the actual DNA coding sequence. It has been found that DNA methylation processes have substantial implications for health, and it seems to be clear that knowledge about methylation processes and modifications of the methyl metabolism and DNA methylation are essential for understanding diseases, for the prophylaxis, diagnosis and therapy of diseases.

The precise control of genes, which represent a small part only of the complete genome of mammals, involves regulation in consideration of the fact that the main part of the DNA in the genome is not coding. The presence of such 'trunk' DNA containing introns, repetitive elements and potentially actively transposable elements, requires effective mechanisms for their durable suppression (silencing). Apparently, the methylation of cytosine by S-adenosylmethionine (SAM) dependent DNA methyl transferases, which form 5-methylcytosine, represents such a mechanism for the modification of DNA-protein interactions. Genes can be transcribed by methylation-free promoters, even when adjacent transcribed or not-transcribed regions are widely methylated. This permits the use and regulation of promoters of functional genes, whereas the trunk DNA including the transposable elements is suppressed. Methylation also takes place for the long-term suppression of X-linked genes and may lead to either a reduction or an increase of the degree of transcription, depending on where the methylation in the transcription units occurs.

Nearly the complete natural DNA methylation in mammals is restricted to cytosine-guanosine (CpG) dinucleotide palindrome sequences, which are controlled by DNA methyl transferases. CpG dinucleotides are about 1 to 2% of all dinucleotides and are concentrated in CpG islands. According to an art-recognized definition, a region is considered as a CpG island when the C+G content over 200 bp is at least 50% and the percentage of the observed CG dinucleotides in comparison to the expected CG dinucleotides is larger than 0.6 (Gardiner-Garden, M., Frommer, M. (1987) J. Mol. Biol. 196, 261-282). Typically, CpG islands have at least 4 CpG dinucleotides in a sequence of a length of 100 bp.

CpG islands located in promotor regions frequently have a regulatory function for the expression of the corresponding gene. For example, in case the CpG island is hypomethylated, the gene can be expressed. On the other hand, hypermethylation frequently leads to a suppression of the expression. Normally tumour suppressor genes are hypomethylated. But if they become hypermethylated, their expression becomes suppressed. This is observed many times in tumour tissues. By contrast, oncogenes are hypermethylated in healthy tissue, whereas they are hypomethylated in many times in tumour tissues.

The methylation of cytosine has the effect that the binding of proteins is normally prohibited which regulate the transcription of genes. This leads to an alteration of the expression of the gene. Relating to cancer, the expression of genes regulating cell division are thereby altered, for example, the expression of an apoptotic gene is down regulated, while the expression of an oncogene is up regulated. Additionally, hypermethylation may have a long term influence on regulation. Proteins, which deacetylate histones, are able to bind via their 5-methylcytosine binding domain to the DNA when the cytosines get methylated. This results in a deacetylation of the histones, which itself leads to a tighter package of the DNA. Because of that, regulatory proteins are not precluded from binding to the DNA.

The efficient detection of DNA methylation patterns consequently is an important tool for developing new approaches to understand diseases, for the prevention, diagnosis and treatment of diseases and for the screening for disease associated targets. But on the other hand, methods for an efficient detection of DNA methylation require high quality standards in regard to the starting material the genomic DNA. Preferably, the standards are:

I) A sufficient amount of DNA characterized by a methylation pattern specific for a defined condition is comprised in the employed DNA sample. This sufficient amount of DNA is dependent on the method for detecting the methylation pattern as well as on the methylation pattern itself. Typical values are in the range of about 20 pg to about 10 ng. But it has to be considered that the actual amount of this DNA in a sample taken from a patient has to be much higher, at least by a factor of 4-8 times. The reason for this is the loss of DNA during sample providing and sample processing for example DNA isolation;

II) The employed DNA sample has to be free of DNA which might interfere with a choosen method for detecting a desired methylation pattern;

III) The employed DNA sample should preferably also not contain large contamination of DNA which is unrelated to the underlying problem. This is for example *E. Coli* DNA in stool samples or DNA of red blood cells in plasma or serum samples; and IV) The employed DNA should be preferably free of associated or linked proteins, peptides, amino acids, RNA as well as of nucleotides or bases, which are not part of the DNA backbone. These may sterically hinder the detection of methylation.

Pronounced Need in the Art.

At the moment the applicant is not aware of any relevant prior art method. Thereby relevant means that it fulfills the criteria as specified above for providing DNA from remote samples, for providing DNA suitable for methylation analysis, and for medical tests in general.

As the closest prior art, the following documents may be considered: Utting M., et al. (2002) Clinical Cancer Research 8, 35-40. This study indicates that microsatellite marker analysis using free-floating DNA of urine or blood could be relevant for diagnosis and screening of bladder cancer. The sample providing as well as the providing of DNA from the samples is carried out according to standard procedures.

Wong I. H. N., et al. (2003) Clinical Cancer Research 9, 047-1052 describe a new method named RTQ-MSP which is a combination of MSP (methylation sensitive PCR) and real-time PCR. The authors demonstrate that a detection of a particular tumor-derived DNA sequence in plasma, serum and blood cells of already diagnosed hepatocellular carcinoma patients is possible.

U.S. Pat. No. 6,927,028 teaches a method for differentiating DNA species originating form cells of different individuals in biological samples by means of methylation specific PCR. The sample providing as well as the providing of DNA from the samples is carried out according to standard procedures.

Lecomte T., et al. (2002) Int. J. Cancer 100, 542-548 tested free-circulating DNA derived from plasma of colorectal cancer patients for the presence of KRAS2 mutations, for p16 gene promotor methylation, or both. The authors suggest, patients with free-circulating tumor-associated DNA in the blood have a lower probability of a 2-year recurrence-free survival than patients for who no free-circulating tumor-associated DNA in the blood is detected.

SUMMARY OF ASPECTS OF THE INVENTION

Aspects of the present invention relate to compositions and methods for providing DNA fragments from a remote sample.

Particular aspects provide compositions and methods for providing DNA fragments derived from a remote sample, wherein amongst others a remote sample comprising DNA is provided, DNA is isolated from the remote sample, and the isolated DNA is treated in a way which allows differentiation of methylated and unmethylated cytosine. Particular aspects provide compositions and methods for providing a remote sample, the remote sample being characterized in that only a subset of DNA is of interest and the DNA concentration is less about 100 ng/ml. Particular aspects provide compositions and methods for minimizing loss of DNA. Particular aspects provide compositions and methods for isolating as much as possible DNA from a remote sample. Preferably these aspects comprise a subdivision step, a concentration step, or combinations thereof.

Additional, particular embodiments provide compositions and methods for methylation analysis of DNA derived from a remote sample. Particular embodiments provide compositions and methods for identification of a marker. Particular embodiments provide methods for use of a marker.

Other aspects provide for compositions and methods of whole genome amplification of bisulfite treated DNA.

Further aspects provide a kit for carrying out the method of the invention or an embodiment of the method of the invention.

DETAILED DESCRIPTION OF ASPECTS OF THE INVENTION

Figure 1:
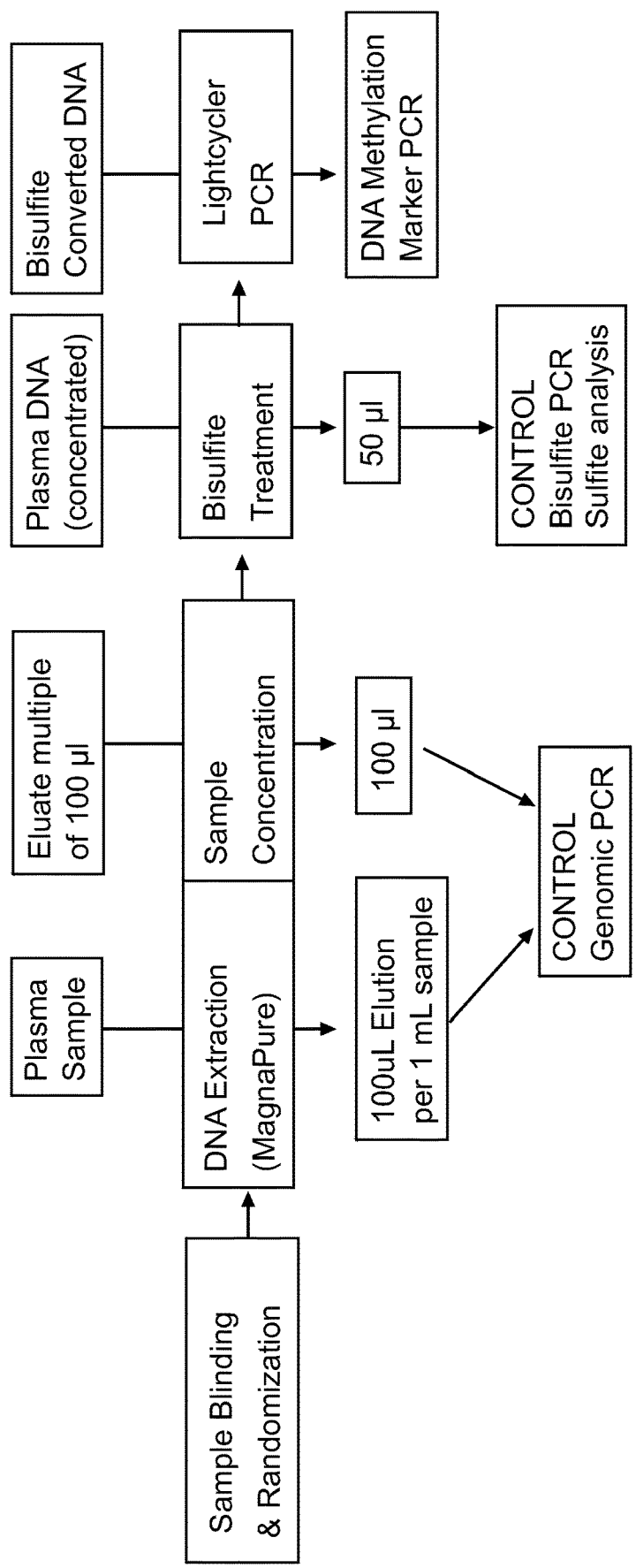
FIG. 1 shows, an overview over one embodiment of the invention.

For achieving various technical objects, aspects the invention teach compositions and methods for providing DNA fragments derived from a remote sample. Said compositions and methods comprise providing a remote sample comprising DNA, isolating DNA from the remote sample, and treating the isolated DNA with a reagent or enzyme which allow differentiation of methylated and unmethylated cytosine.

Particular aspects provide methods to find amongst an enormous plurality of known methods for remote sample providing, DNA isolation and treatments which allowing a differentiation between methylated and unmethylated DNA those methods, which in principle can be used to solve the technical object of the invention. Particular aspects provide further methods to find amongst an enormous plurality of known methods for methylation analysis, marker identification and use of identified markers those methods, which in principle can be used to solve the technical object of the invention. Particular aspects provide suitable combinations and adjustments of these methods with each other in a manner that actually meets the technical object(s).

ADVANTAGES OF ASPECTS OF THE INVENTION

In particular aspects, the exemplary inventive method has the following advantages:

It is characterized by high yields of provided DNA. This is achieved although remote samples are characterized in that they comprise only low levels of DNA, especially low levels of DNA of interest. On the other hand, in many cases the amount of a remote sample is not limited. Therefore according to the invention large amount of remote samples are preferably processed. In particular, a DNA isolation method was selected amongst the enormous number of possible DNA isolation methods which allow the use of large volumes of starting samples. The use of even larger volumes could be achieved according to the invention by dividing the remote sample into subsamples, performing the DNA isolation in parallel, pooling the isolated DNA and concentrating the DNA into a volume suitable for further processing.

The high yields of provided DNA are further determined by the selection of a method for discrimination between methylated and unmethylated cytosine which allows a complete and reliable discrimination and simultaneously minimizes further DNA fragmentation amongst the enormous number of discrimination methods.

In addition, the high yields of DNA after the DNA isolation step and the bisulfite treatment step can even be further raised according to the invention by applying the optional step of whole genome amplification of bisulfite treated DNA.

The exemplary inventive method is further characterized in that contaminations are furthermost avoided. This is based in embodiments of sample collection which efficiently remove components of the sample taken form an individual which are not for interest. For example, the removal of red blood cells from blood to provide a plasma sample. Thereby it is of particular importance on one hand to efficiently remove all red blood cells but minimizing damage to them. Because this will lead to a release of red blood cell DNA, the reason for the removal of the red blood cells. Furthermore, according to in the invention, a DNA isolation method was selected amongst the enormous number of possible DNA isolation methods which excludes the possibility of sample cross contaminations. Taken together, the provided DNA according to the invention is free of DNA contaminations which might interfere with a chosen method for detecting a desired methylation pattern.

The exemplary inventive method is further characterized in that small DNA fragments as well as long DNA fragments are provided. First, this is enabled according to the invention by selection of a DNA isolation method which isolates DNA fragments of at least 100 bp with high efficiency amongst a enormous number of DNA isolation methods. Second, this is enabled according to the invention by selecting of methods of the invention for DNA concentration, for bisulfite treatment, in particular for purification and/or desulfonation of bisulfite treated DNA, and for whole genome amplification amongst the enormous number of other possible methods.

The exemplary inventive method is further characterized in that the provided DNA comprises small DNA fragments as well as long DNA fragments as they are present in the starting remote sample. This particular advantage is achieved according to the invention i) by selecting a DNA isolation method which isolates small DNA fragments at least as small as 100 bp as well as large DNA fragments amongst the enormous number of possible DNA isolation methods; ii) by selecting devices for DNA concentration and purification of bisulfite treated DNA which retain small DNA fragments as well as large DNA fragments amongst the enormous number of possible devices; and iii) by efficiently amplifying small bisulfite treated DNA fragments as well as large ones by the optional step of whole genome amplification of bisulfite treated DNA.

The exemplary inventive method is further characterized in that the provided DNA is free of associated or linked proteins, peptides, amino acids, RNA, nucleotides or bases as well as interfering chemical reagents. According to the invention, this is based therein, that i) a DNA isolation method is selected which is characterized by an efficient removal of associated or linked proteins, peptides, amino acids, RNA, nucleotides or bases amongst the enormous number of possible DNA isolation methods; ii) devices for DNA concentration and purification of bisulfite treated DNA which efficiently remove associated nucleotides or bases amongst the enormous number of possible devices; and iii) a method for discrimination between methylated and unmethylated cytosine is selected which minimizes further DNA fragmentation amongst the enormous number of discrimination methods. The removal of such components is of particular importance because they may sterically hinder the methylation analysis.

Taken together, because of the above explained advantages, the exemplary inventive method allows the use of remote samples for methylation analysis. In particular, said use is characterized in that it is reliable and reproducible. These are two necessary requirements for a medical test.

But, of course, the exemplary inventive method is also characterized by other preferred criteria of a medical test. According to the exemplary inventive method, large amount of samples can be processed. For example, it is possible to carry out the exemplary inventive method in a plate scale. Moreover the different steps can be automated and standardized and therefore robotics can also be used. The different steps are further characterized by a low handling effort. The execution in plate scale, the suitability of the method for automatization and standardization, and the low handling effort also lead to a reduction in costs. In addition the costs are further reduced by the use of devices and solutions which are already available at low expenses. Another advantage of the method of the invention is that every step can easily be performed because only standard laboratory equipment is necessary for its execution. Because of its simplicity, its suitability for automatization, its low handling effort as well as its easy handling, the method of the invention has also a high reliability and reproducibility.

Thus the exemplary inventive method makes remote samples available for methylation based medical test. In other words, it enables a methylation based medical test which is based on non-invasive means or on invasive means which affects as less as possible the patient, which are easy to perform, and which cause low costs.

The exemplary inventive method makes also remote samples available for methylation based discovery of markers. In particular, it allows the identification of markers, characterized by a high sensitivity, a high specificity, or both.

METHOD OF ASPECTS OF THE INVENTION

The method of the invention is a method for providing DNA fragments derived from a remote sample. According to the invention, the method comprises the following steps: providing a remote sample comprising DNA, isolating DNA from the remote sample, and treating the isolated DNA with a reagent or enzyme which allows differentiation of methylated and unmethylated cytosine. In realizing these steps, DNA fragments are provided from a remote sample.

In brief, in particular aspects, the method of the invention is a method for providing DNA fragments derived from a remote sample, comprising:
  providing a remote sample comprising DNA,
  isolating DNA from the remote sample, and
  treating the isolated DNA with a reagent or enzyme which allows differentiation of methylated and unmethylated cytosine.

In particular aspects, the method of the invention is a method which comprises the collecting and preprocessing of a remote sample. The remote sample is thereby characterized in that it comprises genomic DNA. The method of the invention further comprises the extraction of DNA from the collected and preprocessed remote sample. According to the invention, the extracted DNA is subject to a treatment which allows to differentiate if the DNA is methylated or not at a certain position. Such a treatment can be any kind of treatment. Preferably the treatment comprises the use of an enzyme or reagent. Thereby the enzyme can be any kind of enzyme, but preferably the enzyme is protein or RNA molecule. Said reagent can also be any kind of reagent for example but not limited to it a chemical reagent, a pharmaceutical reagent, a biological reagent or a medical reagent.

In an embodiment, the method of the invention is a method, wherein the DNA of the remote sample is characterized in that less than about 5%, less than about 3%, less than about 1%, or less than about 0.1% of the DNA is derived from a defined cell, group of cells, tissue or organ. In a preferred embodiment, the method of the invention is a method, wherein the DNA of the remote sample is characterized in that less than about 1% of the DNA is derived from a defined cell, group of cells, tissue or organ.

According to an embodiment, the provided remote sample comprises less than about 5%, less than about 3%, less than about 1%, or less than about 0.1% DNA which originates from the same defined cell, group of cells, tissue or organ. Preferably, less than about 1% of the DNA is derived from the same defined cell, group of cells, tissue or organ. Thereby said DNA is characterized in having the same methylation pattern at a defined allele or genomic locus.

In an embodiment of the invention, the presence or absence of the said DNA can be detected with more than about 99% confidence interval, more than about 95% confidence interval, more than about 90% confidence interval, more than about 80% confidence interval, more than about 70% confidence interval, or more than about 60% confidence interval. Particularly preferred is a confidence interval of more than about 95%.

According to an embodiment, the percentage of said DNA can be determined within a confidence interval of more than about 99%, more than about 95%, more than about 90%, more than about 80%, more than about 70%, or more than about 60%. Preferably a confidence interval of more than about 95% is applied.

In an embodiment, the method of the invention is a method, wherein the remote sample is characterized in that it comprises less than about 100 ng DNA in 1 ml, less than about 60 ng DNA in 1 ml or less than about 10 ng DNA in 1 ml. In a preferred embodiment, the remote sample comprises less than about 10 ng of DNA in 1 ml remote sample.

According to an embodiment, a remote sample is considered which comprises less than about 1,000 ng, less than about 500 ng, less than about 100 ng, less than about 80 ng, less than about 60 ng DNA, less than bout 40 ng, less than about 20 ng, less than about 10 ng, less than about 1 ng, or less than about 0.1 ng per milliliter remote sample. Preferably, the DNA concentration of a remote sample is less than 10 ng/ml.

In an embodiment the method of the invention is a method, wherein loss of DNA is minimized by at least one selected from the group comprising: selection of a DNA isolation method characterized by high yields of DNA, selection of a method for differentiation of unmethylated and methylated cytosine characterized by high accuracy and high reliability, high accuracy of pipetting, reuse of pipetting device, reuse of device contacted with DNA.

According to an embodiment, it is very important that as much as possible of the DNA of interest is provided for methylation analysis. This importance is based thereon that the DNA of a remote sample comprises only a small percentage of DNA which is relevant for the underlying question. This has been already specified above. Therefore preferably, it is possible to minimize the loss of DNA by at least one of the following provisions: a) selection of a suitable DNA extraction method; b) selection of a suitable method for differentiation if a genomic locus or allele is methylated or not; c) ensuring a high accuracy of pipetting; d) reuse of pipetting devices; and e) reuse of devices brought into contact with DNA of a remote sample.

A suitable DNA extraction method is a method which enables and ensures high yield of DNA. It is further characterized in that it has the possibility of standardization, the possibility of automatization, a high reliability, a high reproducibility, and the exclusion of contamination with for example but not limited to it DNA of other remote samples. Of course, a suitable method should also fulfill as good as possible as much as possible the above specified criteria for a medical test, for processing of a remote sample and for methylation analysis. Therefore in a particular preferred embodiment, the DNA is extracted by means of at least one component of the MagNA Pure Compact Nucleic Acid Isolaton Kit (I) Large Volume (Roche Diagnostics GmbH) or at least a thereto related device.

A suitable method for differentiation between a methylated and a unmethylated genomic locus or allel is characterized in that it allows or ensures a high as possible rate of differentiation with high reliability and high accuracy. Preferably the differentiation is possible for nearly every single site which is capable of being methylated. Furthermore a suitable method should not lead to a fragmentation of DNA. Of course, a suitable method should also fulfill as good as possible as much as possible of the above specified criteria for a medical test, for processing of remote samples and for methylation analysis. Therefore in a particular preferred embodiment, the DNA is treated with bisulfite as essentially carried out as described in WO05/038051 (this reference is incorporated by its entirety).

A high accuracy of pipetting characterized in that only the necessary amount of DNA is transferred to subsidiary steps which enables to exploit the as much as possible of the remote sample DNA. It further assures that the optimum amount of DNA and other reagents is used. This results in optimum reactions and therewith in high quality DNA. Loss of DNA for example but not limited to it by degradation is therewith minimized.

The reuse of pipetting devices is also advantageous. As known in the art, DNA is binding to plastics surfaces as for example pipet tips. But less DNA is bound to a surface which was already brought into contact once with the said DNA. Of course the same holds true for DNA containers for example but not limited to microtiter plates, tubes, columns. However the reuse is also limited by the risk of contaminations. Therefore, only devices brought into contact with DNA of a remote sample are reused for samples or DNA which were derived from the same patient or from the same sample collected from a patient. In another preferred embodiment, the use of devices brought into contact with remote sample DNA is minimized.

In an embodiment the method of the invention is a method, wherein the volume of the remote sample is at least about 1.5 ml, about 2 ml, about 3 ml, about 4 ml, about 5 ml, about 6 ml, about 7 ml, about 8 ml, about 9 ml, about 10 ml, about 11 ml, about 12 ml, about 15 ml, about 20 ml, about 25 ml, about 30 ml, about 40 ml, or about 50 ml. In a preferred embodiment, the volume of the remote sample is at least about 36 ml, about 38 ml, about 40 ml, about 42 ml, or about 45 ml. In a particularly preferred embodiment, the volume of the remote sample is at least about 40 ml. In another preferred embodiment, the volume of the remote sample is at least about 15 ml, about 18 ml, about 20 ml, about 23 ml, or about 25 ml. In a particularly preferred embodiment, the volume of the remote sample is at least about 20 ml. In a further preferred embodiment, the volume of the remote sample is at least about at least about 4 ml, about 5 ml, about 6 ml, about 7 ml, about 8 ml, or about 9 ml. In a particularly preferred embodiment, the volume of the remote sample is at least about 6 ml or about 8 ml.

According to an embodiment, a remote sample is taken or collected from an individual. Said remote sample has a volume of at least about 1.5 ml, about 2 ml, about 3 ml, about 4 ml, about 5 ml, about 6 ml, about 7 ml, about 8 ml, about 9 ml, about 10 ml, about 11 ml, about 12 ml, about 15 ml, about 20 ml, about 25 ml, about 30 ml, about 40 ml, or about 50 ml. Preferably, the volume is at least about 36 ml, about 38 ml, about 40 ml, about 42 ml, or about 45 ml. Most preferably, the volume is at least about 40 ml. Also preferably, the volume is at least about 15 ml, about 18 ml, about 20 ml, about 23 ml, or about 25 ml, and most preferably the volume is at least about 20 ml. Also preferably, the volume is at least about 4 ml, about 5 ml, about 6 ml, about 7 ml, about 8 ml, or about 9 ml. Most preferably, the volume is at least about 6 ml or about 8 ml.

In an embodiment the method of the invention is a method, wherein the remote sample is at least one selected from the group comprising: blood sample, plasma sample, serum sample, body fluid sample, saliva sample, urine sample, semen sample, sample of the fluid from the pleural cavity, sample from the fluid from the peritoneal cavity, sample of the cerebrospinal fluid, smear from a epithelial surface, sputum sample, stool sample, ejaculate sample, tears sample, sweat sample, lymph fluid sample, bronchial lavage sample, pleural effusion sample, meningal fluid sample, glandular fluid sample, fine needle aspirates sample, nipple aspirates fluid sample, spinal fluid sample, conjunctival fluid sample, vaginal fluid sample, duodenal fluid sample, pancreatic juice sample, or bile sample.

According to an embodiment, the remote sample can be any kind of a sample. Preferably, the remote sample is a sample which is characterized in that it comprises at least one component which is mainly located distantly from the other components of the said sample. For example blood is not a remote sample with regard to a red blood cell, but it is a remote sample with regard to a DNA fragment which is derived from a tumor located in the lung. According to a preferred embodiment, a remote sample is a sample of blood, plasma, serum, body fluid, saliva, urine, semen, fluid from the pleural cavity, fluid from the peritoneal cavity, cerebrospinal fluid, smear from a epithelial surface, sputum, stool, ejaculate, tears, sweat, lymph fluid, bronchial lavage, pleural effusion, meningal fluid, glandular fluid, fine needle aspirates, nipple aspirates fluid, spinal fluid, conjunctival fluid, vaginal fluid, duodenal fluid, pancreatic juice, or bile. A person skilled in the art probably knows of additional remote samples. Of course, these samples may also be used according to the method of the invention.

In an embodiment the method of the invention is a method, wherein the remote sample is plasma and the providing of the remote sample comprises one or more of the following:

obtaining at least about 5 ml, about 10 ml, about 15 ml, about 20 ml, about 25 ml, about 30 ml, about 35 ml, about 40 ml, about 45 ml, about 50 ml of blood from an individual;

adding EDTA (ethylene-diamine-tetra-acetic acid) to the blood comprising gentle mixing;

adjusting the blood to a final concentration of about 2.2 µmol/l, about 3.2 µmol/l, about 3.7 µmol/l, about 4.0 µmol/l, about 4.5 µmol/l, about 4.9 µmol/l, about 5.4 µmol/l, about 5.9 µmol/l, or about 6.9 µmol/l, dipotassium EDTA (dipotassium ethylene-diamine-tetra-acetic acid) comprising gently mixing;

centrifuging the blood-EDTA mixture at about 750×g, about 1000×g, about 1500×g, or about 2000×g for about 4 min, about 8 min, about 10 min, about 12 min, or about 20 min at about 1° C., about 4° C., about 7° C., about 10° C., about 15° C., about 21° C., or about 27° C.;

transferring the plasma into a new container;

centrifuging the plasma at about 750×g, about 1000×g, about 1500×g, or about 2000×g for about 4 min, about 8 min, about 10 min, about 12 min, or about 20 min at about 1° C., about 4° C., about 7° C., or about 10° C.;

transferring the re-centrifuged plasma into a new container;

cooling a plasma comprising sample at about 0° C., about 2° C., about 4 cC, about 6° C., or about 10° C.;

freezing, storing or transporting a plasma comprising sample at least at about −10° C., about −20° C., about −50° C., about −60° C., about −70° C., about −80° C., about −90° C., or about −196° C.; and performing the providing of the remote sample from obtaining blood from a individual to freezing the corresponding re-centrifuged plasma within about 1, about 2, about 3, about 4, about 5, about 6, or about 8 hours.

According to an embodiment, a remote sample is plasma. According to an preferred embodiment the providing of plasma comprises one or more of the following steps:

obtaining at least about 5 ml, about 10 ml, about 15 ml, about 20 ml, about 25 ml, about 30 ml, about 35 ml, about 40 ml, about 45 ml, about 50 ml of blood from a individual;

adding EDTA (ethylene-diamine-tetra-acetic acid) to the blood comprising gentle mixing;

adjusting the blood to a final concentration of about 2.2 µmol/l, about 3.2 µmol/l, about 3.7 µmol/l, about 4.0 µmol/l, about 4.5 µmol/l, about 4.9 µmol/l, about 5.4 µmol/l, about 5.9 µmol/l, or about 6.9 µmol/l, dipotassium EDTA (dipotassium ethylene-diamine-tetra-acetic acid) comprising gently mixing by immediately inversion for at least about 2 times, about 4 times, about 6 times, about 8 times, about 10 times, about 12 times, about 14 times, or about 18 times;

centrifuging the blood-EDTA mixture at about 750×g, about 1000×g, about 1500×g, or about 2000×g for about 4 min, about 8 min, about 10 min, about 12 min, or about 20 min at about 1° C., about 4° C., about 7° C., about 10° C., about 15° C., about 21° C., or about 27° C.;

transferring the cleared upper phase into a new container, therein the centrifuged container is held upright and the pipet is tilt to touch the edge of the centrifuged container and the surface of the cleared upper phase, transferring only so much of the cleared upper phase until its surface is more than about 20 mm, about 10 mm, about 7 mm, about 5 mm, or about 4 mm distant from the surface of the next layer the buffy coat layer;

centrifuging the plasma sample at about 750×g, about 1000×g, about 1500×g, or about 2000×g for about 4 min, about 8 min, about 10 min, about 12 min, or about 20 min at about 1° C., about 4° C., about 7° C., or about 10° C.;

transferring the re-centrifuged plasma sample into a new container, therein more than the about 20 ml, about 12 ml, about 8 ml, about 5 ml, or about 4 ml of the lowest re-centrifuged plasma sample remain in the centrifugation container;

cooling a blood sample, plasma sample or intermediate sample at about 0° C., about 2° C., about 4° C., about 6° C., or about 10° C.;

freezing, storing or transporting a plasma sample or an intermediate sample at least at about −10° C., about −20° C., about −50° C., about −60° C., about −70° C., about −80° C., about −90° C., or about −196° C.; and performing the providing of the remote sample starting from obtaining blood from a individual and ending at freezing the corresponding re-centrifuged plasma sample within about 1, about 2, about 3, about 4, about 5, about 6, or about 8 hours.

In a preferred embodiment, the method of the invention is a method, wherein the remote sample is a plasma sample and the providing of the remote sample comprises one or more of the following:

obtaining at least about 35 ml, about 40 ml, about 45 ml, or about 50 ml of blood from a individual;

adjusting the blood to a final concentration of about 3.7 µmol/l, about 4.0 µmol/l, about 4.5 µmol/l, about 4.9 µmol/l, or about 5.4 µmol/l dipotassium EDTA (dipotassium ethylene-diamine-tetra-acetic acid) comprising gently mixing;

centrifuging the blood-EDTA mixture at about 1500×g for about 10 min at about 4° C., preferably no brakes are used for stopping the centrifuge;

transferring the plasma into a new container;

centrifuging the plasma at about 1500×g for about 10 min at about 4° C., preferably no brakes are used for stopping the centrifuge;

transferring the re-centrifuged plasma into a new container;

cooling a plasma comprising sample at about 0° C., about 2° C., or about 4° C.;

freezing, storing or transporting a plasma comprising sample at least at about −70° C., about −80° C., or about −90° C.; and performing the providing of the remote sample from obtaining blood from a individual to freezing the corresponding re-centrifuged plasma within about 4 hours.

According to a preferred embodiment, the remote sample is a plasma sample and the providing of the plasma sample comprises one or more of the following steps:

obtaining at least about 35 ml, about 4 0 ml, about 45 ml, or about 50 ml of blood from an individual;

adjusting the blood to a final concentration of about 3.7 µmol/l, about 4.0 µmol/l, about 4.5 µmol/l, about 4.9 µmol/l, or about 5.4 µmol/l dipotassium EDTA (dipotassium ethylene-diamine-tetra-acetic acid) comprising gently mixing by immediately inversion for about 10 times;

centrifuging the blood-EDTA mixture at about 1500×g for about 10 min at about 4° C., preferably no brakes are used for stopping the centrifuge;

transferring the cleared upper phase into a new container, therein the centrifuged container is held upright and the pipet is tilt to touch the edge of the centrifuged container and the surface of the cleared upper phase, transferring only so much of the cleared upper phase until its surface is more than about 5 mm distant from the surface of the next layer the buffy coat layer;

centrifuging the plasma sample at about 1500×g for about 10 min at about 4° C., preferably no brakes are used for stopping the centrifuge;

transferring the re-centrifuged plasma sample into a new container, therein more than the about 5 ml of the lowest re-centrifuged plasma sample remain in the centrifugation container;

cooling a blood sample, plasma sample or intermediate sample at about 0° C., about 2° C., or about 4° C.;

freezing, storing or transporting a plasma sample or intermediate sample at least at about −70° C., about −80° C., or about −90° C.; and performing the providing of the remote sample starting from obtaining blood from an individual ending at freezing the corresponding re-centrifuged plasma sample within about 4 hours.

In an embodiment the method of the invention is a method, wherein the remote sample is urine and the providing of the remote sample comprises one or more of the following:

performing prostatic palpation, prostatic massage, or both from the middle of the prostate to the left side of the prostate, to the right side of the prostate or both for about 10 s, about 30 s, about 50 s, about 60 s, about 75 s, or about 120 s;

collecting the first about 5 ml, about 10 ml about 15 ml, about 20 ml, about 25 ml, about 30 ml, about 40 ml of voided urine;

adding EDTA to the urine;

adjusting the urine to a final concentration of about 3 mmol/l, about 6 mmol/l, about 7 mmol/l, about 8 mol/l, about 9 mmol/l, about 9.80 mmol/l, about 10 mmol/l, about 11 mmol/l, about 12 mmol/l, about 13 mmol/l, about 14 mmol/l, about 18 mmol/l, or about 25 mmol/l EDTA (ethylene-diamine-tetra-acetic acid) with a pH of about 5.0, about 6.0, about 7.0, about 7.5, about 8.0, about 8.5, about 9.0, about 10;

cooling the urine comprising sample at about 0° C., about 2° C., about 4° C., about 6° C., or about 10° C.;

freezing, storing or transporting the urine comprising sample at least at about −20° C., about −50° C., about −60° C., about −70° C., about −80° C., about −90° C., or about −196° C.; and performing the providing of the urine sample from collecting the first ml of voided urine to freezing the corresponding urine-EDTA mixture within about 15, about 30, about 45, about 60, about 75, about 90, or about 120 min.

According to an embodiment, the remote sample is urine. According to an embodiment, the providing of a urine sample comprises at least one of the following steps:

performing prostatic palpation, prostatic massage, or both from the middle of the prostate to the left side of the prostate, to the right side of the prostate or both for about 10 s, about 30 s, about 50 s, about 60 s, about 75 s, or about 120 s;

collecting the first about 5 ml, about 10 ml about 15 ml, about 20 ml, about 25 ml, about 30 ml, about 40 ml of voided urine immediately after the prostatic palpation, the prostatic massage, or both;

adding dipotassium EDTA to the urine immediately;

adjusting the urine to a final concentration of about 3 mmol/l, about 6 mmol/l, about 7 mmol/l, about 8 mmol/l, about 9 mmol/l, about 9.80 mmol/l, about 10 mmol/l, about 11 mmol/l, about 12 mmol/l, about 13 mmol/l, about 14 mmol/l, about 18 mmol/l, or about 25 mmol/l EDTA (ethylene-diamine-tetra-acetic acid) with a pH of about 5.0, about 6.0, about 7.0, about 7.5, about 8.0, about 8.5, about 9.0, about 10 comprising gently mixing by inversion immediately after collection;

cooling the urine sample at about 0° C., about 2° C., about 4° C., about 6° C., or about 10° C.;

freezing, storing or transporting the urine sample at least at about −20° C., about −50° C., about −60° C., about −70° C., about −80° C., about −90° C., or about −196° C.; and performing the providing of the urine sample from collecting the first milliliter of voided urine to freezing the corresponding urine sample within about 15, about 30, about 45, about 60, about 75, about 90, or about 120 min.

In a preferred embodiment, the method of the invention is a method, wherein the providing of the urine remote sample comprises one or more of the following:

performing prostatic palpation, prostatic massage, or both from the middle of the prostate to the left side of the prostate, to the right side of the prostate or both for about 60 s;

collecting the first about 20 ml of voided urine;

adjusting the urine to a final concentration of about 9 mol/l, about 9.80 mmol/l, about 10 mmol/l, or about 11 mmol/l, EDTA (ethylene-diamine-tetra-acetic acid) with a pH of about 7.5, about 8.0, or about 8.5;

cooling the urine comprising sample at about 0° C., about 2° C., or about 4° C.;

freezing, storing or transporting the urine comprising sample at least at about −70° C., about −80° C., or about −90° C.; and performing the providing of the urine sample from collecting the first ml of voided urine to freezing the corresponding urine-EDTA mixture within about 60 min.

According to a preferred embodiment, the remote sample is a urine sample and the providing of the urine sample comprises at least one of the following steps:

performing prostatic palpation, prostatic massage, or both from the middle of the prostate to the left side of the prostate, to the right side of the prostate or both for about 60 s;

collecting the first about 20 ml of voided urine immediately after the prostatic palpation, the prostatic massage, or both;

adjusting the urine to a final concentration of about 9 mmol/l, about 9.80 mmol/l, about 10 mmol/l, or about 11 mmol/l, EDTA (ethylene-diamine-tetra-acetic acid) with a pH of about 7.5, about 8.0, or about 8.5 immediately after collection comprising gently mixing by inversion immediately after collection;

cooling the urine sample at about 0° C., about 2° C., or about 4° C.;

freezing, storing or transporting the urine sample at least at about −70° C., about −80° C., or about −90° C.; and performing the providing of the urine sample from collecting the first milliliter of voided urine to freezing the corresponding urine sample within about 60 min.

In an embodiment, the providing of a remote sample comprises the processing of a checklist, a standardized protocol, or both.

According to an embodiment, the providing of a remote sample comprises the use of a checklist, of a protocol, or both. According to an preferred embodiment, a checklist used for providing a remote sample comprises a step by step description of actions which are necessary, which have only to be performed, or both. It may further comprise a note about a precaution. According to an embodiment, a protocol used for providing a remote sample comprises i) the providing and use of at least one remote sample identification number, preferable a combination of numbers and letters or preferable a computer-readable code like a bar code, ii) the recordation of characteristic data about the sample, iii) the recordation of characteristic blinded data of the individual the sample is taken from, iv) or combinations thereof.

In an embodiment the method of the invention is a method, wherein the remote sample is divided into different subsamples subsequent to providing the remote sample.

According to an embodiment, a remote sample is split into different subsamples. This is particularly done, in order to obtain high yields of DNA from a sample collected from a patient. According to an embodiment, the volume of a remote sample collected from a single patient can be larger than the volume suitable for further processing. Therefore the collected remote sample is split into subsamples. These subsamples are then further considered as remote samples. Preferably these remote samples are processed in parallel. The splitting of remote samples is done in particular with regard to the DNA extraction step.

In an embodiment, the method of the invention is a method, wherein the remote sample or at least one component of the remote sample is concentrated subsequent to providing the remote sample.

According to an embodiment, a remote sample is concentrated. According to an embodiment, at least one component of a remote sample is concentrated. Preferably this component is a DNA comprising component. The concentration of a remote sample or at least one component of it is particularly done, in order to obtain high yields of DNA from a sample collected from a patient. According to an embodiment, the volume of a remote sample collected from a single patient can be larger than the volume suitable for further processing. Therefore the collected remote sample or at least one component of the remote sample is concentrated. In a preferred embodiment, the High Pure Viral Nucleic Acid Kit or at least one component of it is used i) for providing the remote sample, ii) for isolating DNA, iii) for treating DNA with a reagent or enzyme allowing the differentiation between methylated or non-methylated cytosine, iv) or combinations thereof. In a preferred embodiment, the method of the invention is a method, wherein the concentration comprises ultrafiltration, volume reduction, or both. In a preferred embodiment, the method of the invention is a method, wherein the concentration comprises protein digestion. Said preferred embodiments are either carried out independently of the DNA isolation or as a substep of it. According to an embodiment, the concentration of a remote sample or at least one component of the remote sample comprises ultrafiltration, volume reduction, or both. Preferably the concentration comprises digestion of protein. Said embodiments are either part of the providing of a remote sample or they are part of the isolation of DNA. According to a preferred embodiment, the concentration of a remote sample or at least one component of it comprises at least one selected form the group comprising: protease, serine protease, thiol protease, carboxy protease, metalloprotease, proteinase K, ultrafiltration device, Microcon filter device for example but not limited to it Y-30 Microcon column, filter device, silica surface, silica membrane, magnetic particle, polystyrol particle, polystyrol surface, positively charged surface, and positively charged membrane, charged membrane, charged surface, charged switch membrane, charged switched surface, column of the ZR DNA Clean & Concentrator-5 Kit, column of the Wizard Genomic DNA Purification Kit, column of the QIAamp DNA Micro Kit, a component of the MagNA Pure Compact Nucleic Acid Isolation Kit (I) Large Volume, a component of the QIAamp UltraSens Virus Kit, a component of the RTP DNA/RNA Virus Supersense Kit, a component of the chemagic Viral DNA/RNA Kit special, a component of the chemagic DNA Blood Kit special, a component of the High Pure Viral Nucleic Acid Kit, a component of the Puregene DNA Isolation Kit, a component of the MasterPure™ Complete DNA and RNA Purification Kit, or a component of the NucliSens® Isolation Kit, ethanol precipitation, propanol precipitation, or vacuum concentration amongst others by means of a centrifuge. A person skilled in the art knows to select other suitable devices or kits in considering the above specifications and named kits. The said devices or kits are well known in the art, for a list of current manufacturers please see below.

In an embodiment, the method of the invention is a method, wherein the isolation of DNA comprises one or more of the following:
   treating the remote sample with a protease,
   treating the remote sample with at least one protein degenerating reagent or solution,
   bringing the DNA of the remote sample in contact with a DNA-purifying device,
   washing the DNA on the DNA-purifying device, and
   recovering the DNA from the DNA-purifying device.

According to an embodiment, the remote sample is subjected to at least one of the following steps: i) treating the remote sample with a protease or a protein degrading reagent; ii) treating the remote sample with at least protein degenerating reagent or solution; purifying the DNA by bringing into contact with a DNA purifying device; washing the DNA; and eluting the DNA from the DNA purifying device.

According to an embodiment, the isolation of DNA from a remote sample comprises the treatment with a protein degrading reagent. Such a reagent can be any kind of reagent as known by those skilled in the art. For example, but not limited to it, the protein degrading reagent is cyanogen bromide.

According to an embodiment, the isolation of DNA from a remote sample comprises the treatment with a protein degenerating reagent. Such a reagent can be any kind of reagent as known by those skilled in the art. For example, but not limited to it, the protein degenerating reagent is a chaotropic salt like guanidine hydrochloride or urea; or a detergent like sodium dodecyl sulphate (SDS).

According to an embodiment, the isolation of DNA from a remote sample comprises the washing of DNA, in particular if it is in contact with the DNA purifying device. Suitable solutions and reagents are well known in the art. For example, but not limited to it, the washing solution can be any mixture of a short-chain alcohol with water like 70% ethanol in water.

According to an embodiment, the isolation of DNA from a remote sample comprises the elution of DNA from a DNA purifying device. Such a reagent can be any kind of reagent as known by those skilled in the art. For example, but not limited to it, the eluting solution is water or any elution buffer supplied with the DNA purifying device.

In an embodiment, the method of the invention is a method, comprising the isolation of DNA by means of the treatment of the remote sample with a protease, wherein the protease is at least one selected from the group comprising: serine protease, thiol protease, carboxy protease, metalloprotease, and proteinase K.

According to an embodiment, the extraction of DNA from a remote sample comprises the use of at least one protease selected from the group comprising: serine protease, thiol protease, carboxy protease, metalloprotease, and proteinase K.

In an embodiment, the method of the invention is a method, comprising the isolation of DNA by means of bringing the DNA of the remote sample into contact with a DNA-purifying device, wherein the DNA purifying device is at least one selected from the group comprising: ultrafiltration, Microcon filter device for example but not limited to it Y-30 Microcon column, filter device, silica surface, silica membrane, magnetic particle, polystyrol particle, polystyrol surface, positively charged surface, and positively charged membrane, charged membrane, charged surface, charged switch membrane, charged switched surface, column of the ZR DNA Clean & Concentrator-5 Kit, column of the Wizard Genomic DNA Purification Kit, column of the QIAamp DNA Micro Kit, a component of the MagNA Pure Compact Nucleic Acid Isolation Kit (I) Large Volume, a component of the QIAamp UltraSens Virus Kit, a component of the RTP DNA/RNA Virus Supersense Kit, a component of the chemagic Viral DNA/RNA Kit special, a component of the chemagic DNA Blood Kit special, a component of the High Pure Viral Nucleic Acid Kit, a component of the Puregene DNA Isolation Kit, a component of the MasterPure™ Complete DNA and RNA Purification Kit, or a component of the NucliSens® Isolation Kit. A person skilled in the art may also think of other possibilities like for example but not limited to it ethanol precipitation or propanol precipitation, vacuum concentration amongst others by means of a centrifuge. A person skilled in the art knows to select other suitable devices or kits in considering the above specifications and named kits. The said devices or kits are well known in the art. The current manufacturers are: Roche Diagnostics GmbH for the MagNA Pure Compact Nucleic Acid Isolation Kit (I) Large Volume or the High Pure Viral Nucleic Acid Kit; Quiagen, Inc. for the QIAamp UltraSens Virus Kit, QIAamp DNA Micro Kit or for the QIAamp DNA Blood Maxi Kit; Invitek Gesellschaft für Biotechnik & Biodesign mbH for the RTP DNA/RNA Virus Supersense Kit; chemagen AG for the chemagic Viral DNA/RNA Kit special or the chemagic DNA Blood Kit special; Gentra Systems, Inc. for the Puregene DNA Isolation Kit; Epicentre Technologies for the MasterPure™ Complete DNA and RNA Purification Kit, Millipore Inc. for the Microcon filter device, Zymo Research Corporation for the ZR DNA Clean & Concentrator-5 Kit, Promega U.S. for the Wizard Genomic DNA Purification Kit, and bioMérieux SA for the NucliSens® Isolation Kit. Of course, other devices or kits may be used as long as they are based on these devices or kits equal if they are available at the time the invention was made or in the future.

According to an embodiment, the DNA-purifying device which is used DNA isolation or extraction is characterized by at least one criteria selected from the group comprising ultrafiltration, Microcon filter device for example but not limited to it Y-30 Microcon column, filter device, silica surface, silica membrane, magnetic particle, polystyrol particle, polystyrol surface, positively charged surface, and positively charged membrane, charged membrane, charged surface, charged switch membrane, charged switched surface, column of the ZR DNA Clean & Concentrator-5 Kit, column of the Wizard Genomic DNA Purification Kit, column of the QIAamp DNA Micro Kit, a component of the MagNA Pure Compact Nucleic Acid Isolation Kit (I) Large Volume, a component of the QIAamp UltraSens Virus Kit, a component of the RTP DNA/RNA Virus Supersense Kit, a component of the chemagic Viral DNA/RNA Kit special, a component of the chemagic DNA Blood Kit special, a component of the High Pure Viral Nucleic Acid Kit, a component of the Puregene DNA Isolation Kit, a component of the MasterPure™ Complete DNA and RNA Purification Kit, a component of the NucliSens® Isolation Kit, ethanol precipitation, propanol precipitation, or vacuum concentration amongst others by means of a centrifuge. Of course, other suitable devices or kits may be used according to the invention insofar as their use is obvious for a person skilled in the art while reading the above specifications and named kits.

In an embodiment, the method of the invention is a method, wherein the isolation of DNA is carried out by use of at least one kit selected from the group comprising: MagNA Pure Compact Nucleic Acid Isolation Kit (I) Large Volume, QIAamp UltraSens Virus Kit, QIAamp DNA Blood Maxi Kit, RTP DNA/RNA Virus Supersense Kit, chemagic Viral DNA/RNA Kit special, chemagic DNA Blood Kit special, High Pure Viral Nucleic Acid Kit, Puregene DNA Isolation Kit, MasterPure™ Complete DNA and RNA Purification Kit, or NucliSens® Isolation Kit. A person skilled in the art knows to select other suitable kits in considering the above named kits. The said kits are well known in the art. For the name of the correspondent manufacturers, please refer above. Of course, other kits may be used as long as they are based on these kits equal if they are available at the time the invention was made or in the future.

According to an embodiment, at least one of the following kits is used for DNA extraction: MagNA Pure Compact Nucleic Acid Isolation Kit (I) Large Volume, QIAamp UltraSens Virus Kit, QIAamp DNA Blood Maxi Kit, RTP DNA/RNA Virus Supersense Kit, chemagic Viral DNA/RNA Kit special, chemagic DNA Blood Kit special, High Pure Viral Nucleic Acid Kit, Puregene DNA Isolation Kit, MasterPure™ Complete DNA and RNA Purification Kit, or NucliSens® Isolation Kit. A person skilled in the art might think of other kits while reading the above named kits. Of course those might also be used according to the invention. This includes in particular also kits which are based on the same technology as the above specified kits, but have different or similar name or might be produced by a different manufacturer.

The use of said kits for isolating DNA is preferred because each of them fulfills the following criteria: i) high yields of DNA; ii) avoidance of cross-contaminations; iii) high degree of standardization; iv) high degree of automatization; v) low handling effort; vi) low cost; vii) ease of handling; viii) small fragments as well as large fragments are purified as present in the sample; ix) high reproducibility; x) high reliability; xi) efficient removal of proteins, peptides, amino acids, RNA, nucleotide or bases.

According to a preferred embodiment, the MagNA Pure Compact Nucleic Acid Isolation Kit (I) Large Volume or the QIAamp UltraSens Virus Kit are used for DNA isolation. The reason for this is, they fulfill best the above specified criteria.

According to an particular preferred embodiment, the MagNA Pure Compact Nucleic Acid Isolation Kit (I) Large Volume is used for DNA isolation because it has the highest reproducibility and the highest reliability.

In an embodiment, the method of the invention is a method, wherein isolated DNA derived from different samples is pooled, concentrated or pooled and concentrated.

According to an embodiment, the extracted DNA derived from the same individual is pooled. According to an embodiment, the extracted DNA derived from the same individual is enriched. According to an embodiment, the extracted DNA derived from the same individual is pooled and enriched simultaneously.

In an embodiment, the method of the invention is a method, wherein the isolated DNA is concentrated and the concentration of isolated DNA comprises at least one selected from the group comprising ultrafiltration, Microcon filter device for example but not limited to it Y-30 Microcon column, filter device, ethanol precipitation, propanol precipitation, silica surface, silica membrane, magnetic particle, polystyrol particle, positively charged surface, and positively charged membrane, charged membrane, charged surface, charged switch membrane, charged switched surface, vacuum concentration, vacuum concentration by means of a centrifuge, column of the ZR DNA Clean & Concentrator-5 Kit, column of the Wizard Genomic DNA Purification Kit, column of the QIAamp DNA Micro Kit, a component of the MagNA Pure Compact Nucleic Acid Isolation Kit (I) Large Volume, a component of the QIAamp UltraSens Virus Kit, a component of the RTP DNA/RNA Virus Supersense Kit, a component of the chemagic Viral DNA/RNA Kit special, a component of the chemagic DNA Blood Kit special, a component of the High Pure Viral Nucleic Acid Kit, a component of the Puregene DNA Isolation Kit, a component of the MasterPure™ Complete DNA and RNA Purification Kit, or a component of the NucliSens® Isolation Kit. A person skilled in the art knows to select other suitable devices or kits in considering the above specifications and named kits. The said kits are well known in the art. Regarding the current manufacturers please refer to the said above. Of course, other devices or kits may be used as long as they are based on said devices or kits equal if they are available at the time the invention was made or in the future.

According to an embodiment, the enrichment of DNA is carried out by means of at least one of the following or combinations thereof: ultrafiltration, Microcon filter device for example but not limited to it Y-30 Microcon column, filter device, ethanol precipitation, propanol precipitation, silica surface, silica membrane, magnetic particle, polystyrol particle, positively charged surface, and positively charged membrane, charged membrane, charged surface, charged switch membrane, charged switched surface, vacuum concentration, vacuum concentration by means of a centrifuge, column of the ZR DNA Clean & Concentrator-5 Kit, column of the Wizard Genomic DNA Purification Kit, column of the QIAamp DNA Micro Kit, a component of the MagNA Pure Compact Nucleic Acid Isolation Kit (I) Large Volume, a component of the QIAamp UltraSens Virus Kit, a component of the RTP DNA/RNA Virus Supersense Kit, a component of the chemagic Viral DNA/RNA Kit special, a component of the chemagic DNA Blood Kit special, a component of the High Pure Viral Nucleic Acid Kit, a component of the Puregene DNA Isolation Kit, a component of the MasterPure™ Complete DNA and RNA Purification Kit, or a component of the NucliSens® Isolation Kit.

The use of said devices is particularly preferred because they fulfill best the following criteria for a medical test based on a remote sample: i) high yields of DNA; ii) avoidance of cross-contaminations; iii) high degree of standardization; iv) high degree of automatization; v) low handling effort; vi) low cost; vii) ease of handling; viii) small fragments as well as large fragments are purified as present in the sample; ix) high reproducibility; x) high reliability; xi) efficient removal of proteins, peptides, amino acids, RNA, nucleotide or bases.

According to an particularly preferred embodiment, ultrafiltration devices, in particular Microcon filter devices are used for enrichment or concentration because they have the highest yield of DNA and allow a recovery of small fragments as well as large fragments as present in the sample.

In an embodiment, the method of the invention is a method, wherein the reagent which allows differentiation of methylated and unmethylated cytosine is a reagent that converts unmethylated cytosine to uracil and leaves methylated cytosine unchanged.

According to an embodiment, treatment which allows to differentiate if DNA is methylated or not at a certain position is a treatment that leads to a conversion of unmethylated cytosine to uracil while methylated cytosines remain unchanged. Such a treatment can be any kind of treatment. Preferably the treatment comprises the use of an enzyme or reagent. Thereby the enzyme can be any kind of enzyme, but preferably the enzyme is a protein or RNA molecule. Said reagent can also be any kind of reagent for example but not limited to it a chemical reagent, a pharmaceutical reagent, a biological reagent or a medical reagent.

In an embodiment, the method of the invention is a method comprising a converting reagent as a differentiation allowing reagent, wherein the reagent that converts unmethylated cytosine to uracil and leaves methylated cytosine unchanged is a bisulfite reagent. A person skilled in the art knows how to apply a bisulfite reagent. Suitable kits for application of bisulfite reagent on DNA are available, for example but not limited to it: EZ DNA Methylation-Gold Kit (Zymo Research Corporation), Methylamp DNA Modification Kit (Epigentek Inc.), MethylEasy DNA Bisulphite Modification Kit (Human Genetic Signatures Pty Ltd).

According to an embodiment, the treatment that leads to a conversion of unmethylated cytosine to uracil while methylated cytosines remain unchanged comprises the use of a bisulfite reagent. A person skilled in the art knows applicable methods or kits for bisulfite treatment. For example, but not limited to it, the kits may be: EZ DNA Methylation-Gold Kit (Zymo Research Corporation), Methylamp DNA Modification Kit (Epigentek Inc.), MethylEasy DNA Bisulphite Modification Kit (Human Genetic Signatures Pty Ltd).

According to a preferred embodiment, a bisulfite treatment is essentially carried out as described in WO05/038051 (this reference is incorporated by its entirety). According to this, in one embodiment DNA is reacted with a bisulfite reagent, characterized in that said reaction is carried out in the presence of a compound out of the group of dioxane, one of its derivatives and a similar aliphatic cyclic ether.

In an embodiment DNA is reacted with a bisulfite reagent, characterized in that said reaction is carried out in the presence of a compound of the following formula:

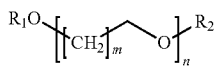

n=1-35000
m=1-3
R1=H, Me, Et, Pr, Bu
R2=H, Me, Et, Pr, Bu

Preferred are thus n-alkylene glycol compounds, particularly their dialkyl ethers, and especially diethylene glycol dimethyl ether (DME).

The bisulfite conversion may take place both in solution as well as also on DNA bound to a solid phase. Preferably sodium disulfite (=sodium bisulfite/sodium metabisulfite) is used, since it is more soluble in water than sodium sulfite. The disulfite salt disproportionates in aqueous solution to the hydrogen sulfite anions necessary for the cytosine conversion. When bisulfite concentration is discussed below, this refers to the concentration of hydrogen sulfite and sulfite anions in the reaction solution. For the method according to the invention, concentration ranges of 0.1 to 6 mol/l are possible.

Particularly preferred is a concentration range of 1 to 6 mol/l, and most particularly preferred, 2-4 μmol/l. However, when dioxane is used, the maximal concentration of bisulfite that can be used is smaller (see below). In selecting the bisulfite concentration, one must consider that a high concentration of bisulfite leads to a high conversion, but also leads to a high decomposition rate due to the lower pH.

Dioxane can be utilized in different concentrations. Preferably, the dioxane concentration amounts to 10 to 35% (vol/vol), particularly preferred is 20 to 30%, and most particularly preferred is 22 to 28%, especially 25%. A dioxane concentration higher than 35% is problematic, since this results in a formation of two phases within the reaction solution. In the particularly preferred embodiments with a dioxane concentration of 22-28%, the final preferred bisulfite concentration amounts to 3.3 to 3.6 μmol/l, and in the most particularly preferred embodiment with a dioxane concentration of 25%, it amounts to 3.5 mol/l (see Examples). The n-alkylene glycol compounds according to the invention can be utilized in a different concentration range. DME is preferably used in concentrations between 1-35% (vol/vol). There is preferably between 5 and 25%, and most preferably 10% DME.

The preferred scavengers utilized according to the invention are chromane derivatives, e.g., 6-hydroxy-2,5,7,8-tetramethylchromane 2-carboxylic acid (also known as: Trolox-C™). Further scavengers are listed in the patent application WO 01/98528 (=DE 100 29 915; =U.S. application Ser. No. 10/311,661; incorporated herein in its entirety).

The bisulfite conversion can be conducted in a wide temperature range from 0 to 95° C. However, as at higher temperatures the rates of both the conversion and decomposition of the DNA increase, in a preferred embodiment the reaction temperature lies between 0-80° C., preferably between 30-80° C. Particularly preferred is a range between 50-70° C.; most particularly preferred between 57-65° C. The optimal reaction time of the bisulfite treatment depends on the reaction temperature. The reaction time normally amounts to between 1 and 18 hours (see: Grunau et al. 2001, Nucleic Acids Res. 2001, 29(13):E65-5; incorporated by reference herein in its entirety). The reaction time is ordinarily 4-6 hours for a reaction temperature of 60° C.

In a particularly preferred embodiment of the method according to the invention, the bisulfite conversion is conducted at mild reaction temperatures, wherein the reaction temperature is then clearly increased for a short time at least once during the course of the conversion. In this way, the effectiveness of the bisulfite conversion can be surprisingly clearly be increased. The temperature increases of short duration are named "thermospikes" below. The "standard" reaction temperature outside the thermospikes is denoted as the basic reaction temperature. The basic reaction temperature amounts to between 0 and 80° C., preferably between 30-80° C., more preferably between 50-70° C., most preferably between 57-65° C., as described above.

The reaction temperature during a thermospike is increased to over 85° C. by at least one thermospike. The optimal number of thermospikes is a function of the basic reaction temperature. The higher the optimal number of thermospikes is, the lower is the basic reaction temperature. At least one thermospike is necessary in each case. And, on the other hand, in principle, any number of thermospikes is conceivable. Of course, it must be considered that with a large number of temperature increases, the decomposition rate of the DNA also increases, and an optimal conversion is no longer assured. The preferred number of thermospikes is thus between 1 and 10 thermospikes each time, depending on the basic reaction temperature. A number of two to 5 thermospikes is thus particularly preferred. The thermospikes increase the reaction temperature preferably to 85 to 100° C., particularly preferably to 90-100° C., and most preferably to 94° C.-100° C.

The duration in time of the thermospikes also depends on the volume of the reaction batch. It must be assured that the temperature is increased uniformly throughout the total reaction solution. For a 20 µl reaction batch when using a thermocycler a duration between 15 seconds and 1.5 minutes, especially a duration between 20 and 50 seconds is preferred. In a particular preferred embodiment the duration is 30 seconds. Operating on a volume of 100 µl the preferred range lies between 30 seconds and 5 minutes, especially between 1 and 3 minutes. Particularly preferred are 1.5-3 minutes. For a volume of 600 µl, a duration of 1 to 6 minutes, is preferred, especially between 2 and 4 minutes. Particularly preferred is a duration of 3 minutes. A person skilled in the art will easily be able to determine suitable durations of thermospikes in relation to a variety of reaction volumes. The above-described use of thermospikes leads to a significantly better conversion rates in the bisulfite conversion reaction, even when the above-described denaturing solvents are not utilized.

According to the invention, the said treatment of DNA with bisulfite is particularly preferred because it has several important advantages in comparison to other known methods or kits of the state of the art. These advantages are: i) higher yield of converted DNA; ii) a nearly complete conversion of unmethylated cytosine while methylated cytosine remain unchanged; and iii) almost no further fragmentation of DNA. These advantages are based in milder reaction conditions because of i) a thermal denaturation of DNA; ii) a comparably lower bisulfite concentration; iii) a slightly more alkaline pH; and iv) the use of a more efficient and more effective radical scavenger.

In a preferred embodiment, the method of the invention is a method, wherein treating DNA with a bisulfite reagent comprises:
  mixing of about 10 to about 250 µl of a solution comprising DNA with about 45 to about 750 µl of bisulfite solution, the bisulfite solution having a pH in the range of about 5.45 to
  about 5.50 comprising about 4.83 to about 4.93 mol/l hydrogensulfite;
  adding about 5 to about 500 µl of an organic radical scavenger solution, the organic radical scavenger solution comprising an organic solvent and about 10 to about 750 mmol/l of 6-hydroxy-2,5,7,8-tetramethyl-chroman-2-carboxylic acid; and
  applying a temperature protocol for about 2 to about 18 h, wherein the reaction is conducted in a temperature range of about 0 to about 80° C. with about 2 to about 5 additional temperature increases, in each case for about 0.5 to about 10 min, to a temperature of about 85 to about 100° C. including an initial temperature increase to a temperature of about 85 to about 100° C.

According to a preferred embodiment, the treatment comprising the use of a bisulfite reagent comprises further:
  mixing of about 10 to about 250 µl of a solution comprising DNA with about 45 to about 750 µl of bisulfite solution, the bisulfite solution having a pH in the range of about 5.45 to about 5.50 comprising about 4.83 to about 4.93 mol/l hydrogensulfite;
  adding about 5 to about 500 µl of an organic radical scavenger solution, the organic radical scavenger solution comprising an organic solvent and about 10 to about 750 mmol/l of 6-hydroxy-2,5,7,8-tetramethyl-chroman-2-carboxylic acid; and
  applying a temperature protocol for about 2 to about 18 h, wherein the reaction is conducted in a temperature range of about 0 to about 80° C. with about 2 to about 5 additional temperature increases, in each case for about 0.5 to about 10 min, to a temperature of about 85 to about 100° C. including an initial temperature increase to a temperature of about 85 to about 100° C.

In a particular preferred embodiment, the method of the invention is a method wherein treating DNA with a bisulfite reagent comprises:
  mixing about 50 to about 150 µl of solution comprising DNA with about 177 to about 531 µl of the bisulfite solution;
  adding about 73 to about 219 µl of dioxane solution, the dioxane solution comprising about 157 mmol/l of 6-hydroxy-2,5,7,8-tetramethyl-chroman-2-carboxylic acid dissolved in 1,4-dioxane; and
  applying a temperature protocol for about 3 to about 16 h, wherein the reaction is conducted in a temperature range of about 57 to about 65° C. with about 2 to about 5 additional temperature increases, in each case for about 3 to about 5 min, to a temperature of about 94 to about 100° C. including an initial temperature increase to a temperature of about 94 to about 100° C.

According to a particular preferred embodiment, the bisulfite treatment of DNA comprises:
  mixing about 50 to about 150 µl of solution comprising DNA with about 177 to about 531 µl of the bisulfite solution;
  adding about 73 to about 219 µl of dioxane solution, the dioxane solution comprising about 157 mmol/l of 6-hydroxy-2,5,7,8-tetramethyl-chroman-2-carboxylic acid dissolved in 1,4-dioxane; and
  applying a temperature protocol for about 3 to about 16 h, wherein the reaction is conducted in a temperature range of about 57 to about 65° C. with about 2 to about 5 additional temperature increases, in each case for about 3 to about 5 min, to a temperature of about 94 to about 100° C. including an initial temperature increase to a temperature of about 94 to about 100° C.

In a particular preferred embodiment, the method of the invention is a method wherein treating DNA with a bisulfite reagent comprises:
  mixing of about 50 to about 150 µl of a solution containing the DNA with about 95 to about 285 µl of the bisulfite solution;
  adding about 15 to about 45 µl of DME solution, the DME solution comprising about 500 mmol/l of 6-hydroxy-2,5,7,8-tetramethyl-chroman-2-carboxylic acid dissolved in diethyleneglycoldimethylether; and
  applying a temperature protocol for about 3 to about 16 h, wherein the reaction is conducted in a temperature range of about 57 to about 65° C. with about 2 to about 5 additional temperature increases, in each case for about 3 to about 5 min, to a temperature of about 94 to about 100° C. including an initial temperature increase to a temperature of about 94 to about 100° C.

According to a particular preferred embodiment, the bisulfite treatment of DNA comprises:
- mixing of about 50 to about 150 µl of a solution containing the DNA with about 95 to about 285 µl of the bisulfite solution;
- adding about 15 to about 45 µl of DME solution, the DME solution comprising about 500 mmol/l of 6-hydroxy-2,5,7,8-tetramethyl-chroman-2-carboxylic acid dissolved in diethyleneglycoldimethylether; and
- applying a temperature protocol for about 3 to about 16 h, wherein the reaction is conducted in a temperature range of about 57 to about 65° C. with about 2 to about 5 additional temperature increases, in each case for about 3 to about 5 min, to a temperature of about 94 to about 100° C. including an initial temperature increase to a temperature of about 94 to about 100° C.

According to an embodiment, the method of the invention is a method, wherein bisulfite treated DNA is subjected directly to methods for methylation analysis. This is especially preferred in view of the avoidance of cross-contaminations in PCR based methods. This embodiment is basically carried out as described in US 2006-0115835 A1, which is incorporated by reference in its entirety). According to this, decontaminated DNA are provided which are suitable for DNA methylation analysis. This embodiment is characterized in that DNA is incubated with a bisulfite reagent comprising solution as described above. This leads to a sulfonation, a deamination, or both of unmethylated cytosine. Deamination is a spontaneous process in an aqueous solution and leads to sulfonated uracil comprising DNA. No desulfonation occurs yet. In a separate step, the DNA comprising sulfonated uracil is brought into contact and incubated with an enzyme which specifically degrades non-sulfonated uracil containing nucleic acids. Such an enzyme is for example Uracil-DNA-Glycosylase (UNG).

In a preferred embodiment for providing a decontaminated template DNA for polymerase based amplification reactions, the sulfonated and/or deaminated template DNA are mixed with an UNG activity and components required for a polymerase mediated amplification reaction or an amplification based detection assay. After degradation of non-sulfonated uracil containing nucleic acids by use of UNG, the UNG activity is terminated and the template DNA is desulfonated by increased temperature. Subsequently the template DNA is ready to be amplified.

In a preferred embodiment, degradation, termination, desulfonation and amplification occur in a single tube during a polymerase based amplification reaction and/or an amplification based assay. Preferably such an amplification is performed in the presence of dUTP instead of dTTP. In a preferred embodiment, sulfonated and partially or completely deaminated DNA after bisulfite treatment is subjected directly to a polymerase based amplification reaction and/or an amplification based assay without any prior desulfonation. The desulfonation occurs during the initial temperature increase of the amplification reaction.

These particular embodiments have the advantage in comparison to known methods of bisulfite treatment that the purification step after bisulfite treatment becomes dispensable. This is a simplification which results in reduction of costs and handling effort, minimizes loss of bisulfite treated DNA and is also time saving.

In an embodiment, the method of the invention is a method, wherein treating DNA with a reagent or enzyme allowing differentiation of the methylation status comprises purifying the treated DNA.

According to an embodiment, the treatment that leads to a conversion of unmethylated cytosine to uracil while methylated cytosines remain unchanged comprises the purification of the bisulfite treated DNA. According to an embodiment, such a purification comprises a desulfonation of the bisulfite treated DNA by bringing the said into contact with a alkaline reagent or solution.

In a preferred embodiment, the method of the invention is a method, wherein purifying the treated DNA comprises the use of at least one selected from the group comprising: ultrafiltration, Microcon filter device, filter device, ethanol, propanol, silica surface, silica membrane, magnetic particle, polystyrol particle, positively charged surface, and positively charged membrane, charged membrane, charged surface, charged switch membrane, charged switched surface, column of the ZR DNA Clean & Concentrator-5 Kit, column of the Wizard Genomic DNA Purification Kit, column of the QIAamp DNA Micro Kit, a component of the MagNA Pure Compact Nucleic Acid Isolation Kit (I) Large Volume, a component of the QIAamp UltraSens Virus Kit, a component of the RTP DNA/RNA Virus Supersense Kit, a component of the chemagic Viral DNA/RNA Kit special, a component of the chemagic DNA Blood Kit special, a component of the High Pure Viral Nucleic Acid Kit, a component of the Puregene DNA Isolation Kit, a component of the MasterPure™ Complete DNA and RNA Purification Kit, or a component of the NucliSens® Isolation Kit. A person skilled in the art knows to select other suitable devices or kits in considering the above specifications and named kits. The said kits are well known in the art. Regarding the current manufacturers please refer to the said above. Of course, other devices or kits may be used as long as they are based on said devices or kits equal if they are available at the time the invention was made or in the future. According to an embodiment, the purification of bisulfite treated DNA comprises the use of at least one of the following or combinations thereof: ultrafiltration, Microcon filter device, filter device, ethanol, propanol, silica surface, silica membrane, magnetic particle, polystyrol particle, positively charged surface, and positively charged membrane, charged membrane, charged surface, charged switch membrane, charged switched surface, column of the ZR DNA Clean & Concentrator-5 Kit, column of the Wizard Genomic DNA Purification Kit, column of the QIAamp DNA Micro Kit, a component of the MagNA Pure Compact Nucleic Acid Isolation Kit (I) Large Volume, a component of the QIAamp UltraSens Virus Kit, a component of the RTP DNA/RNA Virus Supersense Kit, a component of the chemagic Viral DNA/RNA Kit special, a component of the chemagic DNA Blood Kit special, a component of the High Pure Viral Nucleic Acid Kit, a component of the Puregene DNA Isolation Kit, a component of the MasterPure™ Complete DNA and RNA Purification Kit, or a component of the NucliSens® Isolation Kit. According to an preferred embodiment, ultrafiltration devices, in particular Microron filter devices are used for purification, desulfonation, or purification and desulfonation of bisulfite treated DNA because they have the highest yield of bisulfite treated DNA and allow a recovery of small bisulfite treated fragments as well as large bisulfite treated fragments as present in the sample after bisulfite treatment.

In a particular preferred embodiment, the method of the invention is a method, wherein purifying the treated DNA comprises:

adding of about 50 to about 1000 µl of water to the sample after the bisulfite reaction;

applying the mixture onto a Microcon filter device subsequently centrifuging at about 10,000 to about 18,000×g for about 10 to about 30 min;

washing with about 100 to about 800 µl of about 0.2 mol/l sodium hydroxide, and subsequent centrifuging at about 10,000 to about 18,000×g for about 6 to about 25 min;

applying of about 100 to about 800 µl of about 0.1 mol/l sodium hydroxide, and subsequent centrifuging at about 10,000 to about 18,000×g for about 6 to about 25 min;

applying, in 1 to about 8 repetitions, the following: applying of about 100 to about 400 µl water or TE buffer and subsequent centrifuging at about 10,000 to about 18,000×g for about 6 to about 25 min; and eluting by application of about 25 to about 200 µl TE buffer preheated to about 15 to about 65° C., incubation for about 1 to about 30 min at a temperature of about 15 to about 65° C., and subsequent inversion of the Microcon filter device and centrifugation at about 500 to about 5,000×g for about 0.5 to about 30 min.

According to a preferred embodiment, the purification and desulfonation of bisulfite treated DNA comprises:

adding of about 50 to about 1000 µl of water to the sample after the bisulfite reaction;

applying the mixture onto a Microcon filter device subsequently centrifuging at about 10,000 to about 18,000×g for about 10 to about 30 min;

washing with about 100 to about 800 µl of about 0.2 mol/l sodium hydroxide, and subsequent centrifuging at about 10,000 to about 18,000×g for about 6 to about 25 min;

applying of about 100 to about 800 µl of about 0.1 mol/l sodium hydroxide, and subsequent centrifuging at about 10,000 to about 18,000×g for about 6 to about 25 min;

applying, in 1 to about 8 repetitions, the following: applying of about 100 to about 400 µl water or TE buffer and subsequent centrifuging at about 10,000 to about 18,000×g for about 6 to about 2 5 min; and eluting by application of about 25 to about 200 µl TE buffer preheated to about 15 to about 65° C., incubation for about 1 to about 30 min at a temperature of about 15 to about 65° C., and subsequent inversion of the Microcon filter device and centrifugation at about 500 to about 5,000×g for about 0.5 to about 30 min.

In a particular preferred embodiment, the method of the invention is a method, wherein purifying the treated DNA comprises:

a) adding of 200 µl water to the sample after the bisulfite reaction, b) applying the mixture onto a Microcon filter device subsequently centrifuging at about 14,000×g for about 20 min, c) washing with about 400 µl of about 0.2 mol/l sodium hydroxide, and subsequent centrifuging at about 14,000×g for about 10 to about 14 min, d) applying of about 400 µl of about 0.1 mol/l sodium hydroxide, and subsequent centrifuging at about 14,000×g for about 10 to about 14 min, e) applying, in 1 to about 4 repetitions, the following: applying of about 400 µl water or TE buffer and subsequent centrifuging at about 14,000×g for about 12 min; and f) eluting by application of about 45 to about 70 µl TE buffer preheated to about 50° C., incubation for about 10 min at a temperature of about 50° C., and subsequent inversion of the Microcon filter device and centrifugation at about 1,000×g for about 7 min.

According to a particular preferred embodiment, the purification and desulfonation of bisulfite treated DNA comprises:

a) adding of 200 µl water to the sample after the bisulfite reaction, b) applying the mixture onto a Microcon filter device subsequently centrifuging at about 14,000×g for about 20 min, c) washing with about 400 µl of about 0.2 mol/l sodium hydroxide, and subsequent centrifuging at about 14,000×g for about 10 to about 14 min, d) applying of about 400 µl of about 0.1 mol/l sodium hydroxide, and subsequent centrifuging at about 14,000×g for about 10 to about 14 min, e) applying, in 1 to about 4 repetitions, the following: applying of about 400 µl water or TE buffer and subsequent centrifuging at about 14,000×g for about 12 min; and f) eluting by application of about 45 to about 7 0 µl TE buffer preheated to about 50° C., incubation for about 10 min at a temperature of about 50° C., and subsequent inversion of the Microcon filter device and centrifugation at about 1,000×g for about 7 min.

In a particular preferred embodiment, the method of the invention is a method, wherein purifying the treated DNA further comprises at least one of the following:

in step b, applying the mixture in portions onto the Microcon filter device in step b, subsequent to step b, applying of about 400 µl TE buffer, the TE buffer pH 8 containing about 10 mmol/l tris-hydroxymethyl-amino-methan and about 0.1 mmol/l EDTA, subsequent centrifuging at about 14,000×g for about 12 min, in step c, incubating the about 0.2 mol/l sodium hydroxide for about 10 min at room temperature, in step d, incubating the about 0.1 mol/l sodium hydroxide for about 10 min at room temperature, According to a particular preferred embodiment, the purification and desulfonation of bisulfite treated DNA comprises further in addition to the specified above at least one of the following:

in step b, applying the mixture in portions onto the Microcon filter device in step b, subsequent to step b, applying of about 400 µl TE buffer, the TE buffer pH 8 containing about 10 mmol/l tris-hydroxymethyl-amino-methan and about 0.1 mmol/l EDTA, subsequent centrifuging at about 14,000×g for about 12 min, in step c, incubating the about 0.2 mol/l sodium hydroxide for about 10 min at room temperature, in step d, incubating the about 0.1 mol/l sodium hydroxide for about 10 min at room temperature, According to a preferred embodiment, bisulfite treated DNA or bisulfite treated and purified DNA is subjected to a whole genome amplification prior to any further analysis.

In a preferred embodiment, the method of the invention is a method for amplification of at least one nucleic acid, comprising:

providing a nucleic acid sample comprising at least one nucleic acid molecule, treating at least one nucleic acid molecule derived from said sample with an enzyme or reagent which differentiates between methylated bases within said nucleic acid molecule and unmethylated bases within said nucleic acid molecule, extending at least one strand of at least one nucleic acid molecule derived from said sample by at least one nucleotide or PNA-monomer, and amplifying the at least one extended nucleic acid molecule. Thereby the steps of treating at least one nucleic acid molecule derived from said sample and the step of extending at least one strand of at least one nucleic acid molecule derived from said sample can be carried out in arbitrary order.

According to a preferred embodiment, at least one nucleic acid is amplified. The amplification thereby comprises the following steps which may be carried out in any arbitrary order: Providing at least one nucleic acid molecule by providing a nucleic acid sample. Extending at least one strand of at least one nucleic acid molecule by at least one nucleotide or PNA-monomer. Treating at least one nucleic acid molecule with an enzyme or reagent which differentiates between methylated bases within said nucleic acid molecule and unmethylated bases within said nucleic acid molecule. Amplifying at least one nucleic acid molecule. Thereby, preferably, the extended or the treated and extended portions of at least one nucleic acid molecule are used for amplification of said at least one nucleic acid molecules.

In a preferred embodiment, the extension is characterized in that the at least one strand of at least one nucleic acid is extended by one or more single nucleotides or PNA-monomers, by one or more oligonucleotides or PNA-oligomers, by a second nucleic acid derived from the provided nucleic acid sample, or by combinations thereof.

According to a preferred embodiment, the said at least one strand is elongated be either one or more single nucleotides or PNA monomers, by one or more oligonucleotides or PNA-oligomers, by a second nucleic acid preferably derived from the same provided nucleic acid sample as specified above, or by combinations thereof. The nucleotides, oligonucleotides or second nucleic acid can be of any type of nucleotides or nucleotide analog suitable for elongation and as known to those skilled in the art. Preferably, but not limited to it the nucleotides are deoxyribonucleotides, ribonucleotides, locked ribonucleotides or PNA-monomers. Preferably, but not limited to it, the oligonucleotides are oligodeoxyribonucleotides, oligoribonucleotides, or PNA-oligomers, more preferably the PNA-oligomers are arbitrary chimeric oligomers of nucleotides and PNA-monomers, wherein at least one nucleotide is located at the 5' or the 3' end of the chimeric oligomer. The said second nucleic acid can be any nucleic acid either comprised by the provided sample or added during the method of the invention. This second nucleic acid can be of known or unknown sequence. It can be endogenous or artificial. Preferably, the second nucleic acid is a bisulfite treated endogenous nucleic acid provided with the nucleic acid sample.

In a preferred embodiment, the extension is catalyzed template independently.

According to a preferred embodiment, no template is used for extension. This means that the extension occurs randomly or as specified by the used one or more enzymes or further reaction conditions (e.g. but not limited to it, by the provided nucleotides).

In a preferred embodiment, the extension is catalyzed by means of at least one enzyme selected from the group comprising: a transferase, a transferase transferring phosphorus-containing groups, a nucleotidyltransferase, a DNA nucleotidylexotransferase, terminal deoxynucleotidyl transferase (TdT), an enzyme with ribonucleotide transferase activity, a polyribonucleotide nucleotidyltransferase, a tRNA nucleotidyltransferase, RNA uridylyltransferase, a ligase, a ligase forming phosphoric ester bonds, a DNA ligase, a ATP dependent DNA ligase, a single stranded DNA ligase, an ATP dependent single stranded DNA ligase catalyzing intramolecular circularization, CircLigase ssDNA Ligase.

According to a preferred embodiment, the extension reaction is catalyzed by means of at least one enzyme. Said enzyme(s) having at least an activity selected from the group comprising: a transferase activity, a transferase transferring phosphorus-containing groups activity, a nucleotidyltransferase activity, a DNA nucleotidylexotransferase activity, terminal deoxynucleotidyl transferase (TdT) activity, an enzyme with ribonucleotide transferase activity, a polyribonucleotide nucleotidyltransferase activity, a tRNA nucleotidyltransferase activity, RNA uridylyltransferase activity, a ligase activity, a ligase forming phosphoric ester bonds activity, a DNA ligase activity, an ATP dependent DNA ligase activity, a single stranded DNA ligase activity, a ATP dependent single stranded DNA ligase catalyzing intramolecular circularization activity, CircLigase ssDNA Ligase activity. Suitable enzymes are known to those skilled in the art. According to a particular preferred embodiment, the catalyzing enzyme is Terminal Transferase TdT (New England Biolabs Cat # M0252S/L). According to another particular preferred embodiment, the catalyzing enzyme is CircLigase™ ssDNA Ligase (Epicentre Biotechnologies Cat # CL4111K/CL4115K).

In a preferred embodiment, the enzyme or reagent differentiating between methylated bases and unmethylated bases is a bisulfite reagent.

According to a preferred embodiment, the enzyme or reagent differentiating between methylated and unmethylated cytosines is a bisulfite reagent. Suitable reagents as well as suitable methods for differentiation are described above. A person skilled in the art knows how to adjust the use of the said reagents or how to adjust said methods for the amplification of bisulfite treated DNA if case may be.

In a preferred embodiment, the provided nucleic acid is at least in parts DNA, RNA or PNA. According to a preferred embodiment, the nucleic acid provided with nucleic acid sample is a deoxyribonucleic acid (DNA), a ribonucleic acid (RNA), a peptide nucleic acid (PNA) or modifications thereof, for example but not limited to it locked ribonucleic acid (LNA). Of course the provided nucleic acid can also be a combination of said types of nucleic acids.

In a preferred embodiment, the providing of a nucleic acid sample comprises at least one of the following: fragmentation, random fragmentation, fragmentation by mechanical stress, fragmentation by means of an reagent, fragmentation by means of an enzyme, fragmentation by means of an nuclease, fragmentation by means of an restriction endonuclease.

According to a preferred embodiment, the providing of a nucleic acid sample comprises also a fragmentation of the comprised nucleic acids. Suitable methods for fragmentation are known to those skilled in the art. Preferable, the methods of fragmentation are characterized by one or more of the following: random fragmentation, fragmentation by mechanical stress, fragmentation by means of an reagent, fragmentation by means of an enzyme, fragmentation by means of an nuclease, fragmentation by means of an restriction enzyme.

In a preferred embodiment, the amplifying of at least one extended nucleic acid molecule comprises at least one of the following: a polymerase, a heatstable polymerase, a nucleotide, oligonucleotide, a ligase, a reverse transcriptase, a RNA polymerase, a RNase.

According to a preferred embodiment, the extended nucleic acid is amplified by means of one or more enzymes or reagent selected from the group comprising: a polymerase, a heatstable polymerase, a nucleotide, oligonucleotide, a ligase, a reverse transcriptase, a RNA polymerase, a RNase.

In a preferred embodiment, the amplifying of at least one extended nucleic acid molecule comprises the use of at least one method selected from the group comprising: amplification method, PCR method, isothermal amplification method, NASBA method, LCR method or combinations thereof.

According to a preferred embodiment, the extended nucleic acid is amplified according to an amplification method, a PCR method, a isothermal amplification method, a NASBA method, a RACE PCR method, a LCR method or combinations thereof. Suitable methods for amplification are already described herein with exception of the RACE PCR method. A person skilled in the art knows how to adjust said suitable methods for the amplification of bisulfite treated DNA if case may be.

In a preferred embodiment, the methylation of the provided nucleic acid molecule is analyzed by comprising at least one method selected from the group comprising: amplification method, PCR method, isothermal amplification method, NASBA method, LCR method, methylation specific amplification method, MSP (Methylation Specific PCR) method, nested MSP method, HeavyMethyl™ method, detection method, methylation specific detection method, bisulfite sequencing method, detection by means of DNA-arrays, detection by means of oligonucleotide microarrays, detection by means of CpG-island-microarrays, detection by means of restriction enzymes, simultaneous methylation specific amplification and detection method, COBRA method, real-time PCR, HeavyMethyl™ real time PCR method, MSP MethyLight™ method, MethyLight™ method, MethyLight™ Algo™ method, QM method, Headloop MethyLight™ method, HeavyMethyl™ MethyLight™ method, HeavyMethyl™ Scorpion™ method, MSP Scorpion™ method, Headloop Scorpion™ method, methylation sensitive primer extension, and Ms-SNuPE (Methylation-sensitive Single Nucleotide Primer Extension) method or combinations thereof.

According to a preferred embodiment, the provided nucleic acid molecule is analyzed with regard to it methylation. Preferably with regard to its cytosine methylation. Suitable methods are for example, but not limited to, amplification method, PCR method, isothermal amplification method, NASBA method, LCR method, methylation specific amplification method, MSP (Methylation Specific PCR) method, nested MSP method, HeavyMethyl™ method, detection method, methylation specific detection method, bisulfite sequencing method, detection by means of DNA-arrays, detection by means of oligonucleotide microarrays, detection by means of CpG-island-microarrays, detection by means of restriction enzymes, simultaneous methylation specific amplification and detection method, COBRA method, real-time PCR, HeavyMethyl™ real time PCR method, MSP MethyLight™ method, MethyLight™ method, MethyLight™ Algo™ method, QM method, Headloop MethyLight™ method, HeavyMethyl™ MethyLight™ method, HeavyMethyl™ Scorpion™ method, MSP Scorpion method, Headloop Scorpion™ method, methylation sensitive primer extension, and Ms-SNuPE (Methylation-sensitive Single Nucleotide Primer Extension) method or combinations thereof. The said methods are described in detail below.

A particular preferred embodiment comprises
providing a DNA sample comprising at least one DNA molecule,
extending at least one strand of the said provided at least one DNA molecule by at least one single nucleotide or PNA-monomer,
treating the extended at least one DNA strand with an enzyme or reagent which differentiates between methylated cytosine within the said DNA molecule and unmethylated cytosine within said DNA molecule, and
amplifying at least one treated DNA molecule comprising at least one extended strand.

According to a particular preferred embodiment, the said comprised steps for amplification of bisulfite treated are carried out in the following order: i) providing a DNA sample comprising at least one DNA molecule; ii) extending at least one strand of the said provided at least one DNA molecule by at least one single nucleotide or PNA-monomer; iii) treating the extended at least one DNA strand with an enzyme or reagent which differentiates between methylated cytosine within the said DNA molecule and unmethylated cytosine within said DNA molecule; and iv) amplifying at least one treated DNA molecule comprising at least one extended strand. Of course, additional steps may also be included before, in-between, or after the said steps.

In a particular preferred embodiment, the extending of at least one strand of the provided at least one DNA molecule comprises terminal deoxynucleotidyl transferase and one or more nucleotides.

According to a particular preferred embodiment, at least one strand of a provided DNA molecule is extended by means of a terminal deoxynucleotidyl transferase, preferably by means of the Terminal deoxynucleotidyl Transferase TdT (New England Biolabs Cat # M0252S/L). In addition, the extension is carried out in the presence of ribonucleotides, preferably in the presence of either only adenosintriphoshate; in the presence of only thymidintriphosphate; in the presence of only guanosintriphosphate; in the presence of only cytidintriphosphate; or in the presence of only uraciltriphosphate. More preferably the extension is carried out in the presence of deoxynucleotides, preferably in the presence of either only deoxyadenosintriphosphate; in the presence of only deoxythymidintriphosphate; in the presence of only deoxyguanosintriphosphate; in the presence of only deoxycytidintriphosphate; or in the presence of only deoxyuraciltriphophate. The TdT catalyzes the elongation of said at least one single strands by polymerizing the respective nucleotides onto the 3' hydroxyl group of the terminal nucleoside of the single strand. The TdT adds 300-400 nucleotides within 30 min for addition of a dA-tail or for addition of a dT-tail and about 10-100 nucleotides for a dG-tailing or a dC-tailing.

In a particular preferred embodiment, the amplifying of the treated DNA molecule is characterized in that an oligonucleotide or oligomer is at least in parts hybridized to the extended portion of the said DNA molecule.

According to a particular preferred embodiment, a extended bisulfite treated single stranded DNA molecule is amplified by means of at least one oligonucleotide or PNA-oligomer. Thereby said oligonucleotide or oligomer hybridizes completely or in parts onto the extended portion of the extended bisulfite treated single stranded DNA molecule. According to a particular preferred embodiment, the oligonucleotide or oligomer hybridizes completely onto the extended portion. Thereby an amplification of the whole genome provided with the nucleic acid sample is achieved. Furthermore, this embodiment is characterized in that a representative amplification of the whole genome provided in the nucleic acid sample is amplified in large amounts. According to another particular preferred embodiment, the oligonucleotide or oligomer hybridizes only in parts to the extended portion. Thereby a specific amplification of regions of interest is achieved. According to a preferred embodiment, the at least one oligonucleotide or oligomer for amplification hybridizes completely onto the treated DNA strand. This preferred embodiment is already part of another embodiment, in which the extension step is dispensable. According to this embodiment, at least one nucleic acid is provided in form of a nucleic acid sample, the provided nucleic acid sample is treated with an enzyme or reagent which differentiates between methylated and unmethylated bases within said provided nucleic acid, and the treated nucleic acid is amplified by means of at least one oligonucleotide or PNA-oligomer which hybridizes onto said treated nucleic acid. In a preferred embodiment, the said at least one oligonucleotide or PNA-oligomer is guanine-poor and rich in adenine, thymine and cytosine.

Another particular preferred embodiment comprises
providing a DNA sample comprising at least one double stranded DNA molecule or at least two single stranded DNA molecules,
treating the provided DNA with an enzyme or reagent which differentiates between methylated cytosine within the said DNA and unmethylated cytosine within said DNA, wherein treated single stranded DNA molecules are provided,
extending at least one of the said treated single stranded DNA molecules by at least one oligonucleotide or PNA-oligomer or by at least one additional treated single stranded DNA molecule, and
amplifying at least one single stranded DNA molecule after treatment and extension.

According to a particular preferred embodiment, the said comprised steps for amplification of bisulfite treated are carried out in the following order: i) providing a DNA sample comprising at least one DNA molecule; ii) treating the provided DNA with an enzyme or reagent which differentiates between methylated cytosine within the said DNA molecule and unmethylated cytosine within said DNA molecule; iii) extending at least one strand of the provided and treated DNA by at least one single nucleotide or PNA-monomer; and iv) amplifying at least one treated DNA molecule comprising at least one extended strand. Of course, additional steps may also be included before, in-between, or after the said steps.

According to a particular preferred embodiment, the at least one strand of treated DNA is extended by ligation of a oligonucleotide or a chimeric oligomer. The chimeric oligomer being characterized in that it comprises nucleotides and PNA-monomers, wherein at least one nucleotide is located at the 5' or the 3' end of the chimeric oligomer.

According to a particular preferred embodiment, the at least one strand of treated DNA is extended by ligation of a second DNA strand. This second DNA strand can be derived as well by the provided sample or it can be added during the method of the invention. This second DNA strand can be of known or unknown sequence. It can further be endogenous (sequence of a genome for example but not limited to it, the human genome) or it can be artificial. Preferably, the said second DNA strand is a bisulfite treated single DNA strand derived as the first bisulfite treated single DNA strand from the provided nucleic acid sample.

In a preferred embodiment, the extending of at least one treated single stranded DNA molecule comprises a single stranded DNA ligase.

According to a preferred embodiment, the extension reaction is carried out by use of a single stranded DNA ligase. This is in particular preferred, in case the extension reaction is a ligation reaction of a end of a bisulfite treated single strand with another end. Preferably, the single stranded DNA ligase is the CircLigase™ ssDNA Ligase (Epicentre Biotechnologies). But, of course, other ligases might be used according to the invention as long as they are able to ligate bisulfite treated DNA.

In a preferred embodiment, the amplifying of the said DNA molecule is characterized in that at least one oligonucleotide or oligomer is at least in parts hybridized on the extended portion of the treated single stranded DNA molecule.

According to a particular preferred embodiment, a extended bisulfite treated single stranded DNA molecule is amplified by means of at least one oligonucleotide or PNA-oligomer. Thereby said oligonucleotide or oligomer hybridizes completely or in parts onto the extended portion of the extended bisulfite treated single stranded DNA molecule. According to a particular preferred embodiment, the oligonucleotide or oligomer hybridizes completely onto the extended portion. Thereby an amplification of the whole genome provided with the nucleic acid sample is achieved. According to another particular preferred embodiment, the oligonucleotide or oligomer hybridizes only in parts to the extended portion. Thereby a specific amplification of regions of interest is achieved. The specificity is then determined by the sequence of the used oligonucleotides or oligomers and the amplification condition.

According to a preferred embodiment, the at least one oligonucleotide or oligomer for amplification hybridizes completely onto the bisulfite treated single DNA strand. This is in particular preferred for an embodiment, in which the 5' end of the bisulfite treated single DNA strand is ligated to its 3' end resulting into a intramolecular circularization. The oligonucleotide or oligomer hybridization can thereby occur at any site within the bisulfite treated circularisized single DNA strand.

In a preferred embodiment, the treated single stranded DNA molecule is intramolecular ligated during the extension step, and the amplifying is characterized in that at least one oligonucleotide or oligomer hybridizes at an arbitrary site of the circularisized treated single stranded DNA molecule. This embodiment is characterized in that a representative amplification of the whole genome provided in the nucleic acid sample is amplified in large amounts.

A survey for whole genome amplification can be gathered from Hawkins et al.: Whole genome amplification—applications and advances. *Curr Opin Biotechnol.* 2002 February; 13(1):65-7; which is incorporated by reference in its entirety. According to these methods, fragments are amplified by means of a DNA polymerase and primers. The primers may be linker-specific primers, random primers or degenerated primers. Up to now, different WGA methods are described.

In the so-called primer extension pre-amplification (PEP), the amplification is performed by means of a random mixture of oligonucleotide primers having a length of approx. 15 nucleotides (Zhang et al.: Whole genome amplification from a single cell: implications for genetic analysis. Proc Natl Acad Sci USA 89:5847-51, 1992; which is incorporated by reference in its entirety). In the DOP-PCR (degenerate oligonucleotide primed polymerase chain reaction), however, only a degenerate primer is used (cf: Telenius et al.: Degenerate oligonucleotide-primed PCR: general amplification of target DNA by a single degenerate primer; Genomics 13: 718-25, 1992; which is incorporated by reference in its entirety). Another WGA method is the so-called linker/adaptor-PCR. Therein, linkers are ligated to fragments. In the subsequent amplification, primers are used, which specifically bind to the linkers (survey in: Cheung and Nelson: Whole genome amplification using a degenerate oligonucleotide primer allows hundreds of genotypes to be performed on less than one nanogram of genomic DNA. Proc Natl Acad Sci USA. 93:1467 6-9, 1996; which is incorporated by reference in its entirety. The above WGA methods based on PCR have several drawbacks, however. For instance a generation of unspecific amplification artifacts may occur. Further, often an incomplete coverage only of all genome regions will take place. Further, in part short DNA fragments with lengths of less than 1 kB only are generated, (cf: Dean et al.: Comprehensive human genome amplification using multiple displacement amplification. Proc Natl Acad Sci USA. 99:5261-6, 2002; which is incorporated by reference in its entirety). The most powerful method for a whole genome amplification is therefore at present the isothermal "Multiple Displacement Amplification" (MDA, cf: Dean et al. 2002 as above; U.S. Pat. No. 6,124,120). The DNA is reacted with random primers and a DNA polymerase. Polymerases are used here, which are capable to displace the non-template strand of the DNA double strand during the amplification (e.g. a φ29 polymerase). The displaced strands in turn serve as a matrix for the extension of further primers. By using this method, an amplification by more than 5,000 is possible. The average product length is more than 10 kB, and the amplification is distributed rather uniformly over the complete pool of fragments. Commercial kits for the MDA are at present available from two suppliers ("GenomiPhi" from Amersham Biosciences, on the world-wide web at address amershambiosciences.com; "Repli-g" from Molecular Staging, on the world-wide web at address molecularstaging.com).

According to a particular preferred embodiment, the whole genome amplification is achieved by means of a linker/adapter PCR. According to another particular preferred embodiment, the whole genome amplification is achieved by means of multiple displacement amplification.

The herein specified embodiments have the advantage that a whole genome amplification of DNA after bisulfite treatment is enabled. The underlying problem is that a bisulfite treatment, even a mild one, has a negative effect on the integrity of the treated DNA. In other words the DNA molecule treated with bisulfite is fragmented into subfragments. These subfragments are hard to be amplified because of the small size and the property of random primers (oligonucleotides or oligomers) usually used for whole genome amplification to bind on genomic DNA only in large distances. An ever better whole genome amplification characterized in being more representative and resulting in larger amounts of amplified DNA is achieved by two particular preferred embodiments. According to the first particular preferred embodiment, nucleotides are added to one or both of the single strands of a double stranded DNA molecule before bisulfite treatment, preferably by means of terminal deoxynucleotidyl transferase (TdT) activity. After bisulfite treatment, the DNA is amplified using primers which are specific for the added nucleotides. For example in case a poly dA-tail was added, poly dT primers are used. According to the second particular embodiment, a single strand bisulfite converted DNA molecule is provided by bisulfite treatment of a double strand DNA molecule. This single DNA strand is then a) ligated intermolecular to other (at least one) also in the same manner provided single bisulfite treated DNA strands, resulting in an extended single DNA strand; b) it is ligated intramolecular by ligation of its 5' end with its 3' end, resulting in a circularisized single strand DNA molecule; or c) combinations of a) and b) wherein an extended single DNA strand is circularisized. After ligation the single stranded DNA is amplified by random primers. Because of the elongation of the single stranded DNA molecules the polymerase can longer bind and amplify to the bisulfite treated DNA. In other words, the polymerase has a higher processivity as compared to just bisulfite treated non-extended DNA. In addition the ligation to intermolecular chains has also the advantage that fragments are efficiently amplified on which only a few or even no random primer are hybridized.

In an embodiment, the method of the invention is a method as specified above for determining the methylation status of at least one cytosine, a methylation pattern, or both in the DNA of the remote sample, comprising at least one of the following:

determining the methylation status of at least one cytosine in the DNA of the remote sample, each cytosine located at a defined position, determining a methylation pattern in the DNA of the remote sample.

According to an embodiment, at least one of the above specified embodiments is used for determining the methylation status of at least one CpG position in the DNA of the remote sample, a methylation pattern within the DNA of the remote sample, or both, further comprising at least one of the following:

determining the methylation status of at least one CpG position in the DNA of the remote sample, each CpG position located at a defined position, determining a methylation pattern within the DNA of the remote sample.

In an embodiment, the method of the invention is a method for determining a methylation status, a methylation pattern, or both, wherein determining of the methylation status, the methylation pattern, or both comprises the use of at least one method selected from the group comprising: amplification method, PCR method, isothermal amplification method, NASBA method, LCR method, methylation specific amplification method, MSP (Methylation Specific PCR) method, nested MSP method, HeavyMethyl™ method, detection method, agarose gel, staining of an agarose gel, methylation specific detection method, bisulfite sequencing method, detection by means of DNA-arrays, detection by means of oligonucleotide microarrays, detection by means of CpG-island-microarrays, detection by means of restriction enzymes, simultaneous methylation specific amplification and detection method, COBRA method, real-time PCR, HeavyMethyl™ real time PCR method, MSP MethyLight™ method, MethyLight™ method, MethyLight™ Algo™ method, QM method, Headloop MethyLight™ method, HeavyMethyl™ MethyLight™ method, HeavyMethyl™ Scorpion™ method, MSP Scorpion™ method, Headloop Scorpion™ method, methylation sensitive primer extension, and Ms-SNuPE (Methylation-sensitive Single Nucleotide Primer Extension) method.

According to an embodiment, the determining of a methylation status of at least one CpG position, determining of at least one methylation pattern, or both comprises the use of at least one of the following methods or combinations thereof: amplification method, PCR method, isothermal amplification method, NASBA method, LCR method, methylation specific amplification method, MSP (Methylation Specific PCR) method, nested MSP method, HeavyMethyl™ method, detection method, agarose gel, staining of an agarose gel, methylation specific detection method, bisulfite sequencing method, detection by means of DNA-arrays, detection by means of oligonucleotide microarrays, detection by means of CpG-island-microarrays, detection by means of restriction enzymes, simultaneous methylation specific amplification and detection method, COBRA method, real-time PCR, HeavyMethyl™ real time PCR method, MSP MethyLight™ method, MethyLight™ method, MethyLight™ Algo™ method, QM method, Headloop MethyLight™ method, HeavyMethyl™ MethyLight™ method, HeavyMethyl™ Scorpion™ method, MSP Scorpion™ method, Headloop Scorpion™ method, methylation sensitive primer extension, and Ms-SNuPE (Methylation-sensitive Single Nucleotide Primer Extension) method.

According to an embodiment, the amplification method can be any kind of amplification method. A person skilled in the art is in knowledge of suitable amplification methods. According to a preferred embodiment, the amplification method is a PCR method. A person skilled in the art knows suitable PCR methods which can be used according to the invention. According to a preferred embodiment, the amplification method is a isothermal amplification. Suitable amplification methods for use according to the invention are well known in the art. Such a method can be for example but not limited to it the Primer Extension method. According to a preferred embodiment, the amplification method is a NASBA method. NASBA methods are RNA-DNA based amplification methods which comprise the use of a Reverse Transcriptase, a RNA polymerase and a RNase. A person skilled in the art is aware of NASBA methods which can be used according to the invention. According to a preferred embodiment, the amplification method is a Ligase Chain Reaction method. In general, these are amplification methods which are based on the use of a ligase. A person skilled in the art knows suitable LCR which can be used according to the invention.

According to an embodiment, the amplification method is a methylation specific amplification. Suitable methylation specific amplification methods are known to those skilled in the art. According to a preferred embodiment, the methylation specific amplification method is the Methylation Specific PCR (MSP) method. The MSP method allows the assessing of the methylation status of virtually any group of CpG sites within a CpG island, independent of the use of methylation-sensitive restriction enzymes (Herman et al. Proc. Natl. Acad. Sci. USA 93:9821-9826, 1996; U.S. Pat. No. 5,786,146; each of which are incorporated by reference in their entireties). Briefly, DNA is modified by sodium bisulfite converting all unmethylated, but not methylated cytosines to uracil, and subsequently amplified with primers specific for methylated versus unmethylated DNA. MSP primer pairs contain at least one primer, which hybridizes to a bisulfite treated CpG dinucleotide. Therefore, the sequence of said primers comprises at least one CpG dinucleotide. MSP primers specific for non-methylated DNA contain a "T" at the 3' position of the C position in the CpG. Preferably, therefore, the base sequence of said primers is required to comprise a sequence having a length of at least 9 nucleotides which hybridizes to the bisulfite converted nucleic acid sequence, wherein the base sequence of said oligomers comprises at least one CpG dinucleotide. MSP requires only small quantities of DNA and is sensitive to 0.1% methylated alleles of a given CpG island locus. Bisulfite treatments and amplification method described herein may be used in combination with this detection method.

According to a preferred embodiment, the amplification is a nested MSP method. The nested MSP method is essentially carried out as described in WO 02/18649 and US 20040038245 (each of which are incorporated by reference in their entireties). This MSP method considers the apparent conflict of requiring high specificity of the MSP primer to sufficiently differentiate between CG and TG positions and of allowing a mismatch in order to create a unique restriction site.

It comprises the expanding of copy numbers of the genetic region of interest. Therefore a polymerase chain reaction is used to amplify a portion of said region wherein the methylation of interest resides. Thereby an amplification product is generated. An aliquot of said product is then used in a second, methylation-specific, polymerase chain reaction to detect the presence of methylation. In other words a non methylation specific PCR is performed prior to the methylation specific PCR.

According to a preferred embodiment, the amplification method is the HeavyMethyl™ method. The HeavyMethyl™ method is essentially carried out as described in WO 02/072880 and Cottrell S E et al. Nucleic Acids Res. 2004 Jan. 13; 32(1):e10 (each of which are incorporated by reference in their entireties). This method comprises the use of blocking probe oligonucleotides which may be hybridized to the bisulfite treated template nucleic acid concurrently with the PCR primers. Preferably, the blocking oligonucleotides are characterized in that their base sequence comprises a sequence having a length of at least 9 nucleotides which hybridizes to the chemically treated nucleic acid sequence. Thereby the base sequence of said blocker oligonucleotides comprises at least one CpG, TpG or CpA dinucleotide. The amplification of the template nucleic acid is suppressed in case the complementary sequence of the blocking probe is present in the template. In such a case the amplification is terminated at the 5' position of the blocking probe. The blocking probe may be designed to hybridize to the bisulfite treated nucleic acid in a methylation status specific manner. For example, methylated nucleic acids within a population of unmethylated nucleic acids can be detected by suppressing the amplification of nucleic acids which are unmethylated at a position in question. Therefore a blocking probe would comprise a 'CpA' or 'TpA' at the position in question, as opposed to a 'CpG' if the suppression of amplification of methylated nucleic acids is desired. The use of blocker oligonucleotides requires for an efficient disruption of polymerase-mediated amplification that the blocker oligonucleotides cannot be elongated by the polymerase. According to the HeavyMethyl™ method, this is achieved through the use of blockers that are 3'-deoxyoligonucleotides, or oligonucleotides derivatized at the 3' position with other than a "free" hydroxyl group. For example, but not limited to it, 3'-O-acetyl oligonucleotides are representative of a preferred class of blocker molecules.

Additionally, polymerase-mediated degradation of the blocker oligonucleotides should be precluded. Preferably, such preclusion comprises either i) the use of a polymerase lacking 5'-3' exonuclease activity, or ii) the use of modified blocker oligonucleotides. These modified blocker oligonucleotides are characterized in having, for example, thioate bridges at the 5'-terminii. This renders the blocker molecule nuclease-resistant. Particular applications may not require such 5' modifications of the blocker oligonucleotide. For example, degradation of the blocker oligonucleotide will be substantially precluded if the blocker- and primer-binding sites overlap. Thereby the binding of the primer is precluded (e.g., in case of excess blocker oligonucleotide). Therefore the polymerase cannot bind on the primer and elongated it. Because no polymerase is extending the primer, the blocking oligonucleotide will not be degraded. A particularly preferred embodiment of the HeavyMethyl™ method, for purposes of the present invention and as implemented herein, comprises the use of peptide nucleic acid (PNA) oligomers as blocking oligonucleotides. Such PNA blocker oligomers are ideally suited because they are neither degraded nor extended by the polymerase.

According to an embodiment, the detection method can be any kind of detection method. A person skilled in the art is in knowledge of suitable detection methods. Preferably, a detection method can be any kind of detection method which comprises the use of a fluorescent dye, a non-fluorescent dye, a mass label, a separation by size, or a separation by weight. For example, but not limited to it, the detection method is a separation by size in an agarose gel followed by a staining of DNA by means of a fluorescent dye. According to a preferred embodiment, the detection method is a methylation specific detection. A person skilled in the art knows suitable methylation specific detection methods. According to a preferred embodiment, the methylation specific detection method is a bisulfite sequencing method. The bisulfite sequencing method is essentially carried out as described in Frommer et al, Proc. Natl. Acad. Sci. USA 89:1827-1831, 1992. The bisulfite sequencing method is a method wherein the sequencing of a previously amplified fragment of the bisulfite treated genomic DNA is carried out. As the bisulfite treated DNA is amplified before sequencing, an amplification method as described herein may be used in combination with this detection method. It is further especially preferred that the results of a bisulfite sequencing are essentially analyzed as described in EP 02090203.7, which is incorporated by reference in its entirety. In brief, according to this method the degree of methylation of a cytosine is determined by means of an electropherogram of one or more bases. Thereby the area underneath the electropherogram of a detected base is calculated. The degree of methylation is then deduced by comparison this value for a cytosine position to be analyzed with the value obtained for an unmethylated cytosine. For better results, the determination and the consideration of the conversion rate of cytosine to uracil of the bisulfite treatment and/or a standardization of electropherogram signals is favorable.

According to a preferred embodiment, the detection method is a method of detection by means of a DNA-array. A person skilled in the art knows a lot of suitable DNA-arrays. Preferably, a DNA array comprises DNA molecules which are bound to or elsewise associated with a solid phase. The array can be characterized, for example but not limited to it, in that the DNA molecules are arranged on the solid phase in the form of a rectangular or hexagonal lattice. Thereby the solid phase is at least one phase selected from the group comprising: silicon, glass, polystyrene, aluminum, steel, iron, copper, nickel, silver, gold, nitrocellulose, or plastics such as but not limited to it nylon. But also combinations of the said materials are thinkable. For detection, the DNA hybridized on the array is labeled, preferably with a fluorescent dye. Such labelling is for example, but not limited to it, the simple attachment of Cy3 and Cy5 dyes to the 5'-OH of the DNA fragment. The detection of the fluorescence of the hybridized DNA may be carried out, for example, but not limited to it, via a confocal microscope.

According to a particular preferred embodiment, the detection method is a method of detection by means of a oligonucleotide microarray. An overview of the prior art in oligomer array manufacturing can be gathered from a special edition of Nature Genetics (Nature Genetics Supplement, Volume 21, January 1999, and from the literature cited therein; this reference is incorporated according to its entirety as well as the therein cited references).

According to a particular preferred embodiment, the detection method is a method of detection by means of a CpG-island-microarray. Thereby the immobilized or associated DNA of the array comprises sequences which were derived from CpG islands.

According to a particular preferred embodiment, the detection method is a method of detection by means of a DNA-array as essentially described in WO 99/28498, WO 01/38565, or in WO 02/18632, each of which are incorporated by reference in their entireties.

According to a preferred embodiment, the detection method is a method of detection by means of restriction enzymes. A person skilled in the art is in knowledge of suitable methods. According to a preferred embodiment, the methylation specific amplification and the detection are carried out simultaneously. Suitable methods are known to those skilled in the art. According to a particular preferred embodiment, the method for simultaneous methylation specific amplification and detection is the COBRA method. The COBRA method is a quantitative methylation method useful for determining DNA methylation levels at specific gene loci in small amounts of genomic DNA (Xiong & Laird, Nucleic Acids Res. 25:2532-2534, 1997; which is incorporated by reference in its entirety). According to the COBRA method, restriction enzyme digestion is used to reveal methylation-dependent sequence differences in PCR products of bisulfite-treated DNA. Methylation-dependent sequence differences are first introduced into the genomic DNA by bisulfite treatment. PCR amplification of the bisulfite converted DNA is then performed using methylation unspecific primers followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. Additionally, restriction enzyme digestion of PCR products amplified from bisulfite-converted DNA is also used, in the method described by Sadri & Hornsby (Nucl. Acids Res. 24:5058-5059, 1996; which is incorporated by reference in its entirety). Bisulfite treatments and amplification methods described herein may be used in combination with this detection method.

According to a particular preferred embodiment, the method for simultaneous methylation specific amplification and detection is a real-time PCR method. A person skilled in the art knows suitable real-time PCR methods. According to a particular preferred embodiment, the real-time PCR method is a HeavyMethyl™ method. The HeavyMethyl™ method is thereby performed as described above by means of a real-time PCR machine.

According to a particular preferred embodiment, the real-time PCR method is a MethyLight™ method. The MethyLight™ method is a high-throughput quantitative methylation method that utilizes fluorescence-based real-time PCR (TaqMan™) technology that requires no further manipulations after the PCR step (Eads et al., Cancer Res. 59:2302-2306, 1999). Briefly, the MethyLight™ process begins with a mixed sample of genomic DNA that is converted, in a bisulfite reaction, to a mixed pool of methylation-dependent sequence differences according to standard procedures. Fluorescence-based PCR is then performed either in an "unbiased" (with primers that do not overlap known CpG methylation sites) PCR reaction, or in a "biased" (with PCR primers that overlap known CpG dinucleotides) reaction. Sequence discrimination can occur either at the level of the amplification process or at the level of the fluorescence detection process, or both.

The MethyLight™ method may be used as a quantitative test for methylation patterns in the genomic DNA sample, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe overlie any CpG dinucleotides. Alternatively, a qualitative test for genomic methylation is achieved by probing of the biased PCR pool with either control oligonucleotides that do not "cover" known methylation sites (a fluorescence-based version of the "MSP" technique also named MSP MethyLight™ method), or with oligonucleotides covering potential methylation sites.

The MethyLight™ process can be used with a "TaqMan®" probe in the amplification process. For example, double-stranded genomic DNA is treated with bisulfite and subjected to one of two sets of PCR reactions using TaqMan® probes; e.g., with either biased primers and TaqMan® probe, or unbiased primers and TaqMan® probe. The TaqMan® probe is dual-labeled with fluorescent "reporter" and "quencher" molecules, and is designed to be specific for a relatively high GC content region so that it melts out at about 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system.

Variations on the TaqMan® detection technology that are also suitable include the use of dual-probe technology (LightCycler™), fluorescent amplification primers (Sunrise™ technology), Molecular Beacon Probes (Tyagi S., and Kramer F. R., Nature Biotechnology 14, 303-308, 1996), Sorpion primers (Whitcombe et al., Nature and Biotechnology, 17, 804-807, 1999), or LNA (Locked Nucleid Acid) Double-Dye Oligonucleotide probes (Exiqon A/S). All of these techniques may be adapted in a manner suitable for use with bisulfite treated DNA, and moreover for methylation analysis within CpG dinucleotides.

Bisulfite treatments and amplification methods described herein may be used in combination with the MethyLight™ method or its variants.

According to a particular preferred embodiment, the real-time PCR method is the MethyLight™ ALGO™ method. The MethyLight™ ALGO™ method is an improved method of the MethyLight™ method as essentially described in EP 04090255.3, which is incorporated by reference in its entirety. According to this improved method, the degree of methylation is calculated from the signal intensities of probes using different algorithms.

According to a particular preferred embodiment, the real-time PCR method is the QM (quantitative methylation) assay. This assay is a methylation unspecific and therefore unbiased real-time PCR amplification. It is accompanied by the use of two methylation specific probes (MethyLight™) one for the methylated amplificate and a second for the unmethylated amplificate. In this way, two signals are generated which can be used a) to determine the ratio of methylated (CG) to unmethylated (TG) nucleic acids, and at the same time b) to determine the absolute amount of methylated nucleic acids. For the later, a calibration of the assay is necessary with a known amount of control DNA.

According to preferred embodiment, the method for simultaneous methylation specific amplification and detection is a Headloop PCR method. The Headloop PCR method is a suppression PCR method. It essentially carried out as described in Rand K. N., et al., Nucleic Acid Research, 33(14), e127, which is incorporated by reference in its entirety. It is a PCR method for distinguishing related sequences in which the selectivity of amplification is dependent from the amplicon's sequence. A 5' extension is included in one (or both) primer(s) that corresponds to sequences within one of the related amplicons. After copying and incorporation into the amplificate this sequence is then able to loop back, anneal to the internal sequences and prime to form a hairpin structure. This structure prevents then further amplification. Thus, amplification of sequences containing a perfect match to the 5' extension is suppressed while amplification of sequences containing mismatches or lacking the sequence is unaffected.

According to a particular preferred embodiment, the method for simultaneous methylation specific amplification and detection is a combination of the Headloop PCR method and the MethyLight™ method, also named Headloop MethyLight™ method.

According to preferred embodiment, the method for simultaneous methylation specific amplification and detection is a Scorpion™ method. This method was first described by Whitcombe et al.: Detection of PCR products using self-probing amplicons and fluorescence. Nat Biotechnol. 1999; 17(8):804-7; Thelwell et al.: Mode of action and application of Scorpion™ primers to mutation detection. Nucleic Acids Res. 2000 Oct. 1; 28(19):3752-61; U.S. Pat. Nos. 6,326,145; 6,365,729; US 20030087240 A1; each of which are incorporated by reference in their entireties). Several embodiments of this method are known to those skilled in the art. All of these methods have the intramolecular probing in common. According to the so-called Hairloop variant, Scorpion™ primers possess a specific probe sequence at their 5' end. This sequence is present in a hairloop like configuration. A fluorescent dye and a quencher are located in spatial proximity at the end of the probing sequence. After denaturation subsequent to an amplification cycle, the probe hybridizes intramolecularly onto the elongated primer sequence of the same strand. Thereby the hairloop is opened, the dye and the quencher are separated and thus the dye's signal can be detected.

Other Scorpion™ method variants are for example the Duplex variant (Solinas et al.: Duplex Scorpion™ primers in SNP analysis and FRET applications. Nucleic Acids Res. 2001 Oct. 15; 29(20):E96), or the variants as described in U.S. Pat. No. 6,326,145 and US 20030087240, each of which are incorporated by reference in their entireties.

According to a particular preferred embodiment, the Scorpion™ method is a method as essentially described in WO 05/024056, which is incorporated by reference in its entirety. According to a particular preferred embodiment, the method for simultaneous methylation specific amplification and detection is a combination of the HeavyMethyl™ method and the Scorpion™ method, also named HeavyMethyl™ Scorpion™ method.

According to a particular preferred embodiment, the method for simultaneous methylation specific amplification and detection is a combination of the HeavyMethyl™ method and the MethyLight™ method, also named HeavyMethyl™ MethyLight™ method.

According to a particular preferred embodiment, the method for simultaneous methylation specific amplification and detection is a combination of the MSP method and the Scorpion™ method, also named MSP Scorpion™ method.

According to a particular preferred embodiment, the method for simultaneous methylation specific amplification and detection is a combination of the Headloop method and the Scorpion™ method, also named Headloop Scorpion™ method.

According to a preferred embodiment, the method for simultaneous methylation specific amplification and detection is a method of methylation specific primer extension. A person skilled in the art knows several methods which can be used according to the invention.

According to a particular preferred embodiment, the method of methylation specific primer extension is the Ms-SNuPE (methylation-sensitive Single Nucleotide Primer Extension) method. The Ms-SNuPE method is a method as essentially carried out as described in Gonzalgo et al., Nucleic Acids Research 25(12), 2529-2531, 1997 and U.S. Pat. No. 6,251,594.

According to the Ms-SNuPE method, regions of interest are amplified by PCR from bisulfite treated DNA. After purification of the PCR products, primers are proximately hybridized in front of the position to be analyzed. The primer is then elongated by a single nucleotide either with labeled dCTP or with differently labeled dTTP. In case the cytosine in the original DNA was methylated, then dCTP will be incorporated because methylated cytosines remain unchanged during bisulfite treatment. In the other case, the cytosine in the original DNA was unmethylated, then dTTP will be incorporated because unmethylated cytosine is converted to uracil by bisulfite treatment and subsequent PCR will substitute uracil by thymine. By detection of the different labels, it can be distinguished if a cytosine of a CpG position was methylated or unmethylated. The MS-SNuPE method can also be performed in a quantitative manner.

According to a particular preferred embodiment, the method of methylation specific primer extension is a method as essentially described in WO 01/062960, WO 01/062064, or WO 01/62961.

All of these methods can be performed in a quantitative manner. According to WO 01/062960, the primer to be extended hybridizes with its 3' terminus completely or only partially onto the positions of interest. An extension of at least one nucleotide occurs only if the primer hybridizes completely. WO 01/062064 discloses a method in which the primer to be extended hybridizes proximately adjacent or at a distance of up to ten bases to the position to be analyzed. The primer is then extended by at least a single nucleotide. The third method is described in WO 01/62961. According to this method, two set of oligonucleotides are hybridized to the amplified DNA after bisulfite treatment. The first type of oligonucleotide hybridizes 5' proximately adjacent or at a distance of up to 10 bases to the position to be analyzed. The second type of oligonucleotide hybridizes on the amplified DNA so that its 5' terminus hybridizes 3' proximately adjacent to said position to be analyzed. Through this, the two oligonucleotide are separated from each other by a gap of in the range of 1 to 10 nucleotides. The first type of oligonucleotide is then extended by means of a polymerase, wherein not more than the number of nucleotides lying between the two oligonucleotides are added. Thereby nucleotides are used which comprise differentially labeled dCTP and/or dTTP. The two oligonucleotides are then linked to each other by means of a ligase enzyme. In case the cytosine in the original DNA was methylated, then dCTP will be incorporated. In case the cytosine in the original DNA was unmethylated, then dTTP will be incorporated.

Of course other similar methods, which are further developed methods of the named methods or combinations thereof are also useable according to the invention.

In an embodiment, the method of the invention is a method as specified above for identification of a marker, further comprising:
  identification of at least one methylation pattern comprising the methylation status of at least two CpG positions, said CpG positions are comprised by one DNA fragment and are localized in cis, and wherein the methylation pattern differs between DNA derived from a cell, group of cells, tissue, organ or individual characterized by a condition A and DNA derived from a cell, group of cells, tissue, organ or individual characterized by a condition B; and
  selecting a cut off value for the percentage of DNA fragments characterized by a identified methylation pattern within a mixture of DNA fragments, wherein a percentage value equal to or larger than the cut off value is indicative for condition A and a percentage value smaller than the cut off value is indicative for condition B, or wherein a percentage value smaller than the cut off value is indicative for condition A and a percentage value equal to or larger than the cut off value is indicative for condition B.

According to an embodiment, a marker is identified, whereby at least one of the herein described embodiments is comprised. The marker identification further comprises at least the following additional steps: i) identifying at least one methylation pattern, and ii) selecting a threshold value of the fraction of DNA fragments comprising said at least one methylation pattern in comparison to all DNA fragments within a group of DNA fragments. Thereby step i) is characterized in that in two aspects. First, the methylation pattern comprises at least the methylation status of two CpG position, said CpG positions are comprised by one DNA fragment and are localized in cis. As a person skilled in the art knows, a localization in cis means that the corresponding CG dinucleotides have the same orientation on the same DNA strand. The second aspect refers to the said at least one methylation pattern in that DNA obtained from a cell, group of cells, tissue, organ or individual characterized by a condition A can be distinguished from DNA obtained from a cell, group of cells, tissue, organ or individual characterized by a condition B by one of the said methylation patterns or a combination of them.

According to a preferred embodiment, step i) is characterized in that the marker is a pre-identified methylation pattern. Thereby said pattern might be known to be indicative for a condition which is similar to the condition of interest.

According to a preferred embodiment, step ii) is realized in that a) a value representing the fraction of DNA fragments comprising said at least one methylation pattern in comparison to all DNA fragments within a group of DNA fragments is equal to or larger than the threshold value is indicative for a condition A, and b) a value representing said fraction of DNA fragments is smaller than the threshold value is indicative for condition B.

According to preferred embodiment, step ii) is realized in that a) a value representing the fraction of DNA fragments comprising said at least one methylation pattern in comparison to all DNA fragments within a group of DNA fragments is larger than the threshold value is indicative for a condition A, and b) a value representing said fraction of DNA fragments is equal to or smaller than the threshold value is indicative for condition B.

According to a preferred embodiment, step ii) is realized in that a) a value representing the fraction of DNA fragments comprising said at least one methylation pattern in comparison to all DNA fragments within a group of DNA fragments is smaller than the threshold value is indicative for a condition A, and b) a value representing said fraction of DNA fragments is equal to or larger than the threshold value is indicative for condition B.

According to preferred embodiment, step ii) is realized in that a) a value representing the fraction of DNA fragments comprising said at least one methylation pattern in comparison to all DNA fragments within a group of DNA fragments is equal to or smaller than the threshold value is indicative for a condition A, and b) a value representing said fraction of DNA fragments is larger than the threshold value is indicative for condition B. According to these embodiments of step ii), condition A, condition B, or both can be any condition as described herein.

According to a preferred embodiment, the herein described embodiments for identifying a marker are characterized in that they allow the identification of a marker with at least one criteria selected from the group comprising: more than about 20% sensitivity, more than about 30% sensitivity, more than about 35% sensitivity, more than about 40% sensitivity, more than about 50% sensitivity, more than about 60% sensitivity, more than about 70% sensitivity, more than about 80% sensitivity, more than about 90% sensitivity, more than about 95% sensitivity, more than about 99% sensitivity, more than about 40% specificity, more than about 50% specificity, more than about 60% specificity, more than about 70% specificity, more than about 80% specificity, more than about 85% specificity, more than about 90% specificity, more than about 95% specificity, or more than about 99% specificity.

In a preferred embodiment, the method of the invention is a method for identifying of a marker, wherein the identification of a marker is enabled with at least one of the following:
  a sensitivity of more than about 20%, about 30%, about 35%, about 40%%, about 50%, about 60%, about 70%, about 80%, about 90%, about 95%, or about 99%;
  a specificity of more than about 40%, about 50%, about 60%, about 70%, about 80%, about 85%, about 90%, about 95%, or about 99%.

Said particularly preferred embodiment was applied by the applicant in several studies for identifying a marker. One of these studies led to the identification of a colon cancer marker, which became the subject matter of the U.S. 60/672, 242; U.S. 60/676,997; U.S. 60/697,521 and U.S. 60/723, 602. Said marker is specified by a sensitivity of 57% at a specificity of 96% in a set of 233 samples obtained from healthy individuals and 127 samples obtained from colorectal cancer patients or by a sensitivity of 50% at a specificity of 95% in a set of 83 samples obtained from healthy individuals and 209 samples obtained from colorectal cancer patients. Explicit reference is made to U.S. 60/723,602, which is incorporated by reference in its entirety. U.S. 60/723,602 demonstrates that said particular preferred embodiment of the invention enables the identification of a marker with at least a sensitivity of more than about 20%, about 30%, about 35%, about 40%, about 50%, about 60%, about 70%, about 80%, about 90%, about 95%, or about 99%; a specificity of more than about 40%, about 50%, about 60%, about 70%, about 80%, about 85%, about 90%, about 95%, or about 99%; or both. As a person skilled in the art knows, the values for sensitivity and specificity are specific for a performed study. Further, they are dependent from each other and it is possible to rise the value for one by lowering the value for the other.

According to a preferred embodiment, the method of the invention is a method for identifying of a marker, wherein the identification of a marker is enabled with
  a sensitivity of more than about 20%, about 30%, about 35%, about 40%, about 50%, about 60%, about 70%, about 80%, about 90%, about 95%, or about 99%; and
  a specificity of more than about 40%, about 50%, about 60%, about 70%, about 80%, about 85%, about 90%, about 95%, or about 99%.

According to a preferred embodiment, the herein described embodiments for identifying a marker are characterized in that they allow the identification of a marker with a sensitivity of more than about 20%, about 30%, about 35%, about 40%, about 50%, about 60%, about 70%, about 80%, about 90%, about 95%, or about 99% at a specificity of more than about 40%, about 50%, about 60%, about 70%, about 80%, about 85%, about 90%, about 95%, or about 99%.

In a particularly preferred embodiment, the method of the invention is a method for identification of a marker, wherein a colon cancer marker is identified characterized by at least one of the following:
  a sensitivity of at least about 25%, about 35%, about 40%, about 50%, about 55%, about 60%, about 70%, about 80%, about 85%, about 90%, about 95%, or about 99%; and
  a specificity of at least about 65%, about 75%, about 80%, about 85%, about 90%, about 95%, or about 99%.

According to a preferred embodiment, a colon cancer marker is identified, the marker having at least one of the following characteristics:
  a sensitivity of at least about 25%, about 35%, about 40%, about 50%, about 55%, about 60%, about 70%, about 80%, about 85%, about 90%, about 95%, or about 99%; and
  a specificity of at least about 65%, about 75%, about 80%, about 85%, about 90%, about 95%, or about 99%.

In a particularly preferred embodiment, the method of the invention is a method for identification of a marker, wherein a colon cancer marker is identified characterized by
  a sensitivity of at least about 25%, about 35%, about 40%, about 50%, about 55%, about 60%, about 70%, about 80%, about 85%, about 90%, about 95%, or about 99%; and a specificity of at least about 65%, about 75%, about 80%, about 85%, about 90%, about 95%, or about 99%.

According to a preferred embodiment, a colon cancer marker is identified, the marker having a sensitivity of at least about 25%, about 35%, about 40%, about 50%, about 55%, about 60%, about 70%, about 80%, about 85%, about 90%, about 95%, or about 99% at a specificity of at least about 65%, about 75%, about 80%, about 85%, about 90%, about 95%, or about 99%.

In a preferred embodiment, the method of the invention is a method for identification of a marker characterized by selecting a cut off value, wherein the cut off value is selected according to at least one of the following criteria:
- a sensitivity of more than about 15%, about 25%, about 35%, about 40%, about 50%, about 55%, about 60%, about 70%, about 80%, about 85%, about 90%, or about 95%; and
- a specificity of more than about 20%, about 40%, about 50%, about 60%, about 65%, about 70%, about 75%, about 80%, about 85%, about 90%, about 95% or about 99%.

According to a preferred embodiment, a marker is identified by selecting a threshold value according to at least one of the following:
- a sensitivity of more than about 15%, about 25%, about 35%, about 40%, about 50%, about 55%, about 60%, about 70%, about 80%, about 85%, about 90%, or about 95%; and
- a specificity of more than about 20%, about 40%, about 50%, about 60%, about 65%, about 70%, about 75%, about 80%, about 85%, about 90%, about 95% or about 99%.

According to a preferred embodiment, a marker is identified by selecting a threshold value according to a sensitivity of more than about 15%, about 25%, about 35%, about 40%, about 50%, about 55%, about 60%, about 70%, about 80%, about 85%, about 90%, or about 95% at a specificity of more than about 20%, about 40%, about 50%, about 60%, about 65%, about 70%, about 75%, about 80%, about 85%, about 90%, about 95% or about 99%.

In a preferred embodiment, the method of the invention is a method for identification of a marker for at least one of the following: diagnosing a condition, providing a prognosis of a condition, predicting treatment response of a condition, determining a predisposition for a condition, predicting a predisposition for a condition, determining a progression of a condition, predicting a progression of a condition, grading a condition, staging a condition, classification of a condition, characterization of a condition, or combinations thereof, wherein the condition is a healthy condition or an adverse event, wherein one of the said is deduced from the percentage value for DNA fragments characterized by pre-identified methylation pattern within a mixture of DNA fragments, and wherein the corresponding methylation status of CpG positions are measured according to an embodiment described herein, further comprising at least one of the following:
- deducing one of the said for a condition A in case the percentage value is equal to or larger than the selected cut off value;
- deducing one of the said for condition B in case the percentage value is smaller than the selected cut off value;
- deducing one of the said for condition B in case the percentage value is larger than the selected cut off value; and deducing one of the said for condition A in case the percentage value is equal to or smaller than the selected cut off value.

According to a preferred embodiment, a marker is identified for at least one application or use selected from the group comprising: diagnosing a condition, providing a prognosis of a condition, predicting treatment response of a condition, determining a predisposition for a condition, predicting a predisposition for a condition, determining a progression of a condition, predicting a progression of a condition, grading a condition, staging a condition, classification of a condition, characterization of a condition, or combinations thereof. This embodiment is characterized in that
i) the condition is a healthy condition or an adverse event;
ii) the methylation status of the CpG positions of at least one pre-identified methylation pattern are determined for a DNA sample derived from an individual, thereby the determination is preferably carried out according to an embodiment described herein;
iii) determining the proportion of DNA fragments, the fragments are characterized in that they comprise the pre-identified methylation pattern; and
iv) diagnosing of a condition, providing a prognosis of a condition, predicting treatment response of a condition, determining of a predisposition for a condition, predicting of a predisposition for a condition, determining of a progression of a condition, predicting of a progression of a condition, grading of a condition, staging of a condition, classification of a condition, characterization of a condition, or combinations thereof by comparing the determined proportion of DNA fragments with a pre-selected threshold value. According to a particular preferred embodiment, the diagnosing of a condition, the providing a prognosis of a condition, the predicting treatment response of a condition, the determining of a predisposition for a condition, the predicting of a predisposition for a condition, the determining of a progression of a condition, predicting of a progression of a condition, the grading of a condition, the staging of a condition, the classification of a condition, the characterization of a condition, or combinations thereof is made through the determination that said proportion of DNA fragments is greater than, greater than or equal to, equal to, equal to or less than, or less than the pre-selected threshold value.

In a preferred embodiment, the method of the invention is a method for identification of a marker, wherein condition A, condition B, or both are a healthy condition or at least one adverse event, the adverse event comprises at least one category selected from the group comprising: undesired drug interactions; cancer diseases, proliferative diseases or therewith associated diseases; CNS malfunctions; damage or disease; symptoms of aggression or behavioral disturbances; clinical; psychological and social consequences of brain damages; psychotic disturbances and personality disorders; dementia and/or associated syndromes; cardiovascular disease of the gastrointestinal tract; malfunction, damage or disease of the respiratory system; lesion, inflammation, infection, immunity and/or convalescence; malfunction, damage or disease of the body as an abnormality in the development process; malfunction, damage or disease of the skin, of the muscles, of the connective tissue or of the bones; endocrine and metabolic malfunction, damage or disease; and headaches or sexual malfunction.

According to a preferred embodiment for identification of a marker, a condition A, a condition B, or both or a condition in general is a healthy condition or at least one adverse event. Thereby the adverse event comprises at least one category selected from the group comprising: undesired drug interactions; cancer diseases, proliferative diseases or therewith associated diseases; CNS malfunctions; damage or disease; symptoms of aggression or behavioral disturbances; clinical; psychological and social consequences of brain damages; psychotic disturbances and personality disorders; dementia and/or associated syndromes; cardiovascular disease of the gastrointestinal tract; malfunction, damage or disease of the respiratory system; lesion, inflammation, infection, immunity and/or convalescence; malfunction, damage or disease of the body as an abnormality in the development process; malfunction, damage or disease of the skin, of the muscles, of the connective tissue or of the bones; endocrine and metabolic malfunction, damage or disease; and headaches or sexual malfunction.

According to a preferred embodiment, the method of the invention comprises controls. According to a particular preferred embodiment, the collecting of a remote samples comprises the selection and pre-determination of control criteria. Preferably at least one of the control criteria are:

1. Sample selection criteria: Samples selected from patients of a defined disease, samples selected from healthy individuals, samples selected from patients with a similar disease as the defined disease, and samples selected from patients with a non-similar disease as the defined disease.
2. Criteria further specifying samples derived from patient with the defined disease. Such criteria are for example, but not limited to it, stage, grade, class, classification, characteristics, symptoms, previous medical treatment, presence or absence of disease history, availability of histological analysis.
3. General criteria: a) Samples are excluded if the samples are derived from patients or individuals known to have an infectious disease for example but not limited to it HIV (Human Immunodeficiency Virus), HBV (Hepatitis B Virus) or HCV (Hepatitis C Virus). b) Samples are only included
    if they are derived from an individual of a pre-defined minimum age,
    if they are derived from a patient for whom a medical record is available,
    or both.
4. Criteria further specifying samples derived from a healthy individual: Only samples are included which were derived from individuals
    with no histological abnormalities of the organ or the defined disease usually affects,
    with no history regarding the defined disease within a to be determined time frame.
5. Criteria further specifying samples selected from patients with a similar disease as the defined disease: Hereby it has to be pre-determined what a similar disease is. Only samples of patients are included which are characterized by pre-defined criteria for example but not limited to stage, grade, class, classification, characteristics, symptoms, previous medical treatment, presence or absence of disease history, availability of histological analysis.
6. Criteria further specifying samples selected from patients with a non-similar disease as the defined disease: Only samples of patients are included who's disease is active at the time of the analysis, who have no history of the defined disease within a pre-defined time frame. If the non-similar disease is affecting the same tissue or organ than the defined disease, a further selection of samples is preferred according to pre-defined criteria for example but not limited to stage, grade, class, classification, characteristics, symptoms, previous medical treatment, presence or absence of disease history, availability of histological analysis.

According to a particular preferred embodiment, the DNA isolation, bisulfite treatment and methylation analysis of a remote samples comprises the selection and pre-determination of control criteria. Preferably at least one of the control criteria as listed in Table 1 is used.

TABLE 1

Controls suitable for the method of the invention

Positive Controls:

A known amount of DNA is subjected to embodiments of the invention. The concentration of the provided DNA is analyzed. These controls are a measure of the variation in-between batches of remote samples.
Control for isolating DNA:

A solution comprising fully methylated DNA and BSA (bovine serum albumin) is subjected to embodiments of the DNA isolation step. This control gives a measure of the variation of the DNA isolation in-between batches of remote samples. It is further a control for the correct operation of the DNA isolation step.
Control for isolating DNA and for bisulfite treatment a) A solution comprising fully methylated DNA and BSA is subjected to DNA isolation and bisulfite treatment.
b) A solution comprising fully methylated DNA and genomic DNA is introduced at the bisulfite treatment step.
These two type of controls give a measure of the variability and the correct operation of the bisulfite treatment step.
Run of a calibration study Upfront calibration by use of only controls as specified above for the DNA isolation and bisulfite treatment. Such a calibration study gives a range of process variability against which the study is calibrated.
Batch inclusion controls Sample set are excluded in case the controls (see above) within a batch are not within the process variability range of 3 standard deviations (STDev) of the process calibration mean.
Negative Controls - Contamination measured by PCR DNA isolation: a solution comprising BSA and no DNA. Bisulfite treatment: a solution comprising elution buffer and no DNA. Methylation analysis: a solution comprising no DNA, for example but not limited to it water.
Contamination or mishandling control In case a negative control named above is positive, the batches will be excluded from further investigation. The rate of contamination or sample mishandling is determined and is a measure for the quality of the method of the invention.
Prior study inclusion criteria A set of rules is established for inclusion or exclusion of samples based on the performance of the batch controls prior to the study.

The term batch controls may refer herewith to any control as specified in table 1 and which is included into a set of remote samples, said set of samples being processed in parallel according to the invention.

A person with ordinary skills in the art knows how to apply the specified controls of the above embodiments.

Kit.

The subject of the present invention is also a kit, comprising at least one of the following:
    a container;
    one or more solutions, substances, devices or combinations thereof for collecting a urine comprising sample;

one or more solutions, substances, devices or combinations thereof for collecting a plasma comprising sample;
one or more solutions, substances, devices or combinations thereof for DNA isolation;
one or more solutions, substances, devices or combinations thereof for bisulfite treatment of DNA;
one or more solutions, substances, devices or combinations thereof for methylation status or methylation pattern determination;
a description for carrying out an embodiment of the invention.

A preferred kit comprises a container;
one or more solutions, substances, devices or combinations thereof for DNA isolation;
one or more solutions, substances, devices or combinations thereof for bisulfite treatment of DNA;
one or more solutions, substances, devices or combinations thereof for methylation status or methylation pattern determination;
a description for carrying out an embodiment of the invention.

A particular preferred kit comprises in addition at least one of the following: i) one or more solutions, substances, devices or combinations thereof for collecting a urine comprising sample; ii) one or more solutions, substances, devices or combinations thereof for collecting a plasma comprising sample; and iii) one or more solutions, substances, devices or combinations thereof for amplification of bisulfite converted DNA.

A particular preferred kit comprises a container; one or more solutions, substances, devices or combinations thereof for collecting a plasma or a urine comprising sample; one or more solutions, substances, devices or combinations thereof for DNA isolation; one or more solutions, substances, devices or combinations thereof for bisulfite treatment of DNA; one or more solutions, substances, devices or combinations thereof for amplification of bisulfite converted DNA; one or more solutions, substances, devices or combinations thereof for methylation status or methylation pattern determination; and a description for carrying out an embodiment of the invention.

Another particular preferred kit comprises a container and one or more solutions, substances, devices or combinations thereof for amplification of bisulfite converted DNA. Thereby bisulfite converted DNA can be just bisulfite treated or bisulfite treated and purified (desulfonated) DNA. According to the specified kits herein, the one or more solutions, substances, devices or combinations thereof for amplification of bisulfite converted DNA comprise i) a ligase activity, a terminal transferase activity, or both; ii) a polymerase activity; iii) at least one primer; and iv) at least one nucleotide, at least one oligomer, or both.

Preferably, according to the specified kits herein i) the ligase activity is any ligase as specified herein in particular a single stranded DNA ligase; ii) the terminal transferase activity is a transferase activity as specified herein in particular a terminal deoxynucleotidyl transferase; iii) the polymerase activity is an enzyme useful for amplification in particular it is a DNA polymerase, a heatstable DNA polymerase, a RNA transcriptase, a RNA transcriptase in combination with a RNase as an additional enzyme, or a ligase; iv) the primer or primers are primers as specified herein in particular random primers, guanin-poor random primers, specific primers, gene specific primers, or extension specific primers; v) the oligomer is an oligomer as specified herein in particular an oligonucleotide or a chimeric oligomer of at least one PNA-monomer and a 5' or 3' terminal nucleotide. A gene specific primer is any primer which is able to hybridize under stringent or moderately stringent conditions onto a DNA molecule which was derived from the initially provided DNA sample. In contrast thereto, an extension specific primer is any primer which is able to hybridize under stringent or moderately stringent conditions onto a extended portion of a DNA molecule, whereby the extension is realized as described herein. Of course also primers which are in part specific for the extended portion and in part specific for a provided bisulfite treated DNA molecule are also comprised. Of course a preferred kit may only comprise one or more but not all of the said components.

In a preferred kit either
the ligase activity is a single stranded DNA ligase;
the terminal transferase activity is a terminal deoxynucleotidyl transferase;
the polymerase activity is a DNA polymerase, a heatstable DNA polymerase, a RNA transcriptase, a RNA transcriptase, in combination with a RNase as an additional enzyme, or a ligase;
the primer or primers are random primers, guanin-poor random primers, specific primers, gene specific primers, or extension specific primers;
the oligomer is a oligonucleotide or a chimeric oligomer of at least one PNA-monomer and a 5' or 3' terminal nucleotide; or combinations thereof.

A particular preferred kit also comprises a description or manual for carrying out an amplification of bisulfite treated DNA according to a method specified herein.

A preferred kit comprising a container and one or more solutions, substances, devices or combinations thereof for amplification of bisulfite converted DNA comprises in addition one or more solutions, substances, devices or combinations thereof for bisulfite treatment of DNA. Preferably, this also includes one or more solutions, substances, devices or combinations thereof for purifying especially for desulfonation of bisulfite treated DNA.

According to a particular preferred kit, such one or more solutions, substances, devices or combinations thereof for bisulfite treatment of DNA comprise a bisulfite reagent as specified herein and a radical scavenger or radical scavenger solution as specified herein. Preferably, a particular preferred kit comprises in addition a purification device as described herein for example a Microcon™ filter device, a basic reagent or solution like sodium hydroxide as specified herein, or both.

A preferred kit of the invention comprises further one or more of the following:
a description for carrying out a method of the invention for providing a plasma sample; and
a description for carrying out a method of the invention for providing a urine sample.

A preferred kit of the invention, which comprises one or more solutions, substances, devices or combinations thereof for collecting a plasma comprising sample, comprises in addition at least one of the following:
a container comprising EDTA;
a container comprising negative pressure;
a syringe;
one or more container suitable for centrifugation;
one or more pipets;
one or more container suitable for cooling, freezing, storing, transporting, or combinations thereof of the plasma comprising sample;
a case report form; and
a process checklist.

A preferred kit of the invention, which comprises one or more solutions, substances, devices or combinations thereof for collecting a urine comprising sample, comprises in addition at least one of the following:
- a urine collection cup;
- a pipet;
- one or more container comprising EDTA suitable for cooling, freezing, storing, transporting, or combinations thereof of the urine comprising sample;
- a case report form; and
- a process checklist.

Subject of the invention is further a kit as specified above, further comprising at least one of the following:
- one or more solutions, substances, devices or combinations thereof for concentrating a remote sample or at least one component of a remote sample;
- one or more solutions, substances, devices or combinations thereof for concentrating a isolated DNA of a remote sample; or one or more solutions, substances, devices or combinations thereof for purifying bisulfite treated DNA.

According to the invention a kit is preferred comprising one or more of the following:
A) a container;
B) One or more solutions, substances, devices or combinations thereof for collecting a urine comprising sample such as, but not limited to it, at least one urine collection cup, at least one pipet, at least one container comprising EDTA suitable for cooling freezing, storing, transporting, or combinations thereof, at least one case report form, a least one process check list;
C) One or more solutions, substances, devices or combinations thereof for collecting a plasma comprising sample such as, but not limited to it, at least one container comprising EDTA preferably comprising negative pressure or the possibility of applying negative pressure for example a syringe, at least one container suitable for centrifugation, at least one pipet, at least one container comprising EDTA suitable for cooling freezing, storing, transporting, or combinations thereof, at least one case report form, a least one process check list;
D) One or more solutions, substances, devices or combinations thereof for concentrating a remote sample or at least one component of a remote sample as described herein;
E) One or more solutions, substances, devices or combinations thereof for DNA isolation as specified herein;
F) One or more solutions, substances, devices or combinations thereof for concentrating a isolated DNA of a remote sample as described herein;
G) One or more solutions, substances, devices or combinations thereof for bisulfite treatment of DNA as specified herein;
H) One or more solutions, substances, devices or combinations thereof for purifying bisulfite treated DNA.
I) One or more solutions, substances, devices or combinations thereof for methylation status or methylation pattern determination as specified herein;
J) A description for carrying out at least one embodiment described herein.

Use of a Method or a Kit of the Invention.

The methods and kits disclosed herein are preferably used for the analysis of at least one DNA methylation status, at least one DNA methylation level, or of at least one DNA methylation pattern. Of course also combinations of the said are preferred.

Preferably, the embodiments and kits described herein are used for DNA methylation analysis. In particular such analysis comprises the detection and quantification of the methylation or the non-methylation of at least one CpG position. Further, it comprises the identification of at least one CpG position, the methylation of said position or positions is indicative for a condition described herein. Preferably, such analysis comprises the identification of a methylation status, a methylation level, or a methylation pattern. Particularly preferred, such analysis comprises the identification of at least one methylation pattern which is indicative for a condition described herein. Preferably, such analysis comprises the determination of a methylation status at a CpG position, the determination of a methylation level at a CpG position, the quantification of a methylation pattern, or combinations thereof. Particularly preferred, such analysis comprises the quantification of a methylation pattern.

The methods and test kits disclosed herein are further preferably used for identifying an indication-specific target, comprising
a) detecting the percentage of DNA fragments characterized by a defined methylation pattern within a mixture of DNA fragments which are derived from a diseased cell, group of cells, tissue or organ;
b) detecting the percentage of DNA fragments characterized by a defined methylation pattern within a mixture of DNA fragments which are derived from a healthy cell, group of cells, tissue or organ; and
c) defining an indication-specific target based on differences in the percentages of the DNA derived from the diseased cell, group of cells, tissue or organ in comparison to the DNA derived from the healthy cell, group of cell, tissue or organ.

Preferably, the embodiments and kits described herein are used for the identification of an indication specific target. This embodiment comprises the detection and quantification of a fraction of DNA fragments within a group of DNA fragments. The group of DNA fragments is thereby characterized in that it is obtained from a diseased cell, group of cells, tissue or organ. The fraction of DNA fragments is thereby characterized in that each DNA fragment comprises at least one methylation pattern which is specific or indicative for disease associated with the cell, group of cells, tissue or organ. This embodiment comprises also a second detection and quantification of a fraction of DNA fragments within a group of DNA fragments. The group of DNA fragments is thereby characterized in that is obtained from a healthy cell, group of cells, tissue or organ.

The fraction of DNA fragments is thereby characterized in that each DNA fragment comprises at least one methylation pattern which is specific or indicative for said disease. In addition, this embodiment comprises the identification of an indication-specific target. The identification is thereby determined by quantitative differences of said fractions of DNA fragments obtained from diseased cell, group of cells, tissue or organ and obtained from healthy cell, group of cell, tissue or organ.

The use of the methods and kits described herein is especially preferred for identifying an indication-specific target, wherein the indication-specific target is a DNA section, a RNA molecule, a protein, a peptide or metabolic compound.

In particular preferred is the use of embodiments and kits described herein for the identification of an indication-specific target. According to this embodiment, the indication-specific target is a DNA section, a RNA molecule, a protein, a peptide or metabolic compounds.

The use of the methods and kits described herein is further especially preferred, wherein a per se known modulator of said DNA section, said RNA molecule, said protein, said peptide or said metabolic compound is assigned to the specific indication of the diseased cell, group of cell or tissue.

In particular, the use of an embodiment or of a kit described herein is preferred in case a per se known modulator of said DNA section, said RNA molecule, said protein, said peptide or said metabolic compound is assigned to the specific indication of the diseased cell, group of cell or tissue.

Preferably, the use of a said assigned modulator is preferred for preparing a pharmaceutical composition in case of a specific indication, or a specific cancer indication. This is in particular preferred if the indication is a cancer indication.

The use of the methods and kits described herein is further especially preferred for at least one of the following with regard to a patient or individual: diagnosing a condition, prognosing a condition, predicting a treatment response, diagnosing a predisposition for a condition, diagnosing a progression of a condition, grading a condition, staging a condition, classification of a condition, characterization of a condition, or combinations thereof, wherein the condition is a healthy condition or an adverse event, the adverse event comprises at least one category selected from the group comprising: undesired drug interactions; cancer diseases, proliferative diseases or therewith associated diseases; CNS malfunctions; damage or disease; symptoms of aggression or behavioral disturbances; clinical; psychological and social consequences of brain damages; psychotic disturbances and personality disorders; dementia and/or associated syndromes; cardiovascular disease of the gastrointestinal tract; malfunction, damage or disease of the respiratory system; lesion, inflammation, infection, immunity and/or convalescence; malfunction, damage or disease of the body as an abnormality in the development process; malfunction, damage or disease of the skin, of the muscles, of the connective tissue or of the bones; endocrine and metabolic malfunction, damage or disease; and headaches or sexual malfunction.

In particular preferred is the use of embodiments or kits disclosed herein for at least one of the applications or uses selected from the group comprising: diagnosing a condition, prognosing a condition, predicting a treatment response, diagnosing a predisposition for a condition, diagnosing a progression of a condition, grading a condition, staging a condition, classification of a condition, characterization of a condition, or combinations thereof. According to this embodiment, the condition is a healthy condition or an adverse event. Said adverse event comprises at least one category selected from the group comprising: undesired drug interactions; cancer diseases, proliferative diseases or therewith associated diseases; CNS malfunctions; damage or disease; symptoms of aggression or behavioral disturbances; clinical; psychological and social consequences of brain damages; psychotic disturbances and personality disorders; dementia and/or associated syndromes; cardiovascular disease of the gastrointestinal tract; malfunction, damage or disease of the respiratory system; lesion, inflammation, infection, immunity and/or convalescence; malfunction, damage or disease of the body as an abnormality in the development process; malfunction, damage or disease of the skin, of the muscles, of the connective tissue or of the bones; endocrine and metabolic malfunction, damage or disease; and headaches or sexual malfunction.

The use of the methods and kits described herein is further especially preferred for distinguishing cell types or tissue, or for investigating cell differentiation, wherein condition A and condition B are different cell conditions.

The embodiments and kits disclosed herein are also preferable used for distinguishing cell types, tissues or for investigating cell differentiation. This serves in a particularly preferred manner for analyzing the response of a patient to a drug treatment.

Definitions

In particular aspects, the term "methylation status" refers to, but is not limited to, the presence or absence of methylation of a single nucleotide in a single DNA molecule, said nucleotide being capable of being methylated.

In particular aspects, the term "methylation level" refers to, but is not limited to, the average methylation occupancy at a single nucleotide in a plurality of DNA molecules, said nucleotide being capable of being methylated.

In particular aspects, the term "methylation pattern" refers to, but is not limited to, the methylation status of a series of nucleotides located in cis on a single DNA molecule, said nucleotides being capable of being methylated.

In particular aspects, the term "remote sample" includes, but is not limited to, a sample having genomic DNA, wherein the sample is taken from a site (e.g., organ, tissue, body fluid, group of cells, cell, etc.) that is remote with respect to or that is distinct from the site of the cell, group of cells, tissue, or organ from which said genomic DNA originated.

In particular aspects, the term treatment also comprises, but is not limited to, the prophylaxis and the follow-up treatment (e.g. of a tumor not detectable anymore or of a stable tumor). The term prophylaxis comprises in conjunction with the detection the medical check-up, too. In particular aspects, the terms detection or diagnosis and/or treatment or therapy of a cancer disease comprise, but is not limited to, as an option also the detection and/or treatment of metastases of primary tumors in other tissues.

In particular aspects, the term prognosis comprises, but is not limited to, herein statements about the probability of a therapy success or treatment success, and/or statements about the aggressiveness of a disease, and/or statements about the assumed life time without the occurrence of further disease symptoms or metastases and/or about the probability of the necessity of an additional treatment, and/or about the compatibility of undesired side effects.

In particular aspects, a DNA microarray is, but is not limited to, an arbitrary construct with a substrate or carrier, on which or in which different nucleic acid species, such as genes, gene fragments or other oligonucleotides or polynucleotides are arranged, respectively at different defined places assigned to the respective nucleic acid species. At respectively one place one nucleic acid species is arranged, there may however a defined mixture of different nucleic acid species also be arranged at respectively one place, and then every place carries a different mixture. The nucleic acids may be immobilized, this is however not necessarily required, depending on the used substrate or carrier. Not limiting examples for microarrays are: nucleic acid microarrays, gene microarrays, microtiter plates with nucleic acid solutions in the wells, the nucleic acids being immobilized or not immobilized, membranes with nucleic acids immobilized thereupon, and oligonucleotide arrays, microarrays or chips, characterized by that oligonucleotides having a length of up to under 200 bp are immobilized on a surface.

In particular aspects, a modulator of a target is, but is not limited to, a compound or substance, which either inhibits or induces the generation of the target, or reduces or increases the activity of the generated target, referred to the in vitro or in vivo activity in absence of the substance. In so far, a modulator may on the one hand be a substance, modulatingly affecting the development cascade of the target. On the other hand, a modulator may be a substance, which forms a bond with the generated target, and that such that further physiological interactions with endogenous substances are at least reduced or increased. Modulators may also be molecules, which affect and inhibit or activate the transcription of the target gene. Such molecules may for instance be polyamides or zinc finger proteins, which prevent, by binding to DNA regions of the basal transcription machinery, the transcription. The transcription may also take place indirectly by the inhibition of transcription factors, which are essential for the transcription of the target gene. The inhibition of such transcription factors may be guaranteed by binding to so-called decoy aptamers. Modulators may be natural or synthetic molecules that specifically bind to a target or target forerunner or target successor. They may also be target-specific antibodies, for instance human, humanized and non-humanized polyclonal or monoclonal antibodies. The term antibodies further includes phage display antibodies, ribozyme display antibodies (covalent fusion between RNA and protein) and RNA display antibodies (produced in vitro). The term also includes antibodies, which are modified by chimerization, humanization or deimmunization, and specific fragments of the light and/or heavy chain of the variable region of basic antibodies of the above type. The production or extraction of such antibodies with given immunogenes is well known to the average person skilled in the art and needs not to be explained in detail. Further are included bispecific antibodies, which on the one hand bind to a trigger molecule of an immune effector cell (e.g. CD3, CD16, CD64), and on the other hand to an antigen of the tumor target cell. This will cause in the case of a binding that for instance a tumor cell is killed. Modulators may for instance also be suitable target-specific anticalins and affibodies mimicrying an antibody.

In particular aspects, a cancer disease is, but is not limited to, an organ-specific cancer disease, such as lung cancer, ovary cancer, scrotal cancer, prostate cancer, pancreas cancer, breast cancer, cancer of an organ of the digestive tract etc. Suitable sequences with regard to all aspects of the present invention are for instance described in the documents DE 20121979 U1, DE 20121978 U1, DE 20121977 U1, DE 20121975 U1, DE 20121974 U1, DE 20121973 U1, DE 20121972 U1, DE 20121971 U1, DE 20121970 U1, DE 20121969 U1, DE 20121968 U1, DE 20121967 U1, DE 20121966 U1, DE 20121965 U1, DE 20121964 U1, DE 20121963 U1, DE 20121961 U1, DE 20121960 U1, DE 10019173 A1, DE 10019058 A1, DE 10013847 A1, DE 10032529 A1, DE 10054974 A1, DE 10043826 A1, DE 10054972 A1, DE 10037769 A1, DE 10061338 A1, DE 10245779 A1, DE 10164501 A1, DE 10161625 A1, DE 10230692, DE 10255104, EP 1268855, EP 1283905, EP 1268857, EP 1294947, EP 1370685, EP 1395686, EP 1421220, EP 1451354, EP 1458893, EP 1340818, EP 1399589, EP 1478784, WO 2004/035803, and WO 2005/001141, to which explicitly reference is made herewith.

In particular aspects, a pharmaceutical composition according to the invention may be performed, but is not limited to, in a usual way. As counter-ions for ionic compounds can for instance be used Na+, K+, Li+ or cyclohexyl ammonium. Suitable solid or liquid galenic preparation forms are for instance granulates, powders, dragees, tablets, (micro) capsules, suppositories, syrups, juices, suspensions, emulsions, drops or injectable solutions (IV, IP, IM, SC) or fine dispersions (aerosols), transdermal systems, and preparations with protracted release of active substance, for the production of which usual means are used, such as carrier substances, explosives, binding, coating, swelling, sliding or lubricating agents, tasting agents, sweeteners and solution mediators. As auxiliary substances are named here magnesium carbonate, titanium dioxide, lactose, mannite and other sugars, talcum powder, milk protein, gelatin, starch, cellulose and derivatives, animal and vegetable oils such as cod-liver oil, sunflower oil, peanut oil or sesame oil, polyethylene glycols and solvents, such as sterile water and mono or multi-valent alcohols, for instance glycerin. A pharmaceutical composition according to the invention can be produced by that at least one modulator used according to the invention is mixed in a defined dose with a pharmaceutically suitable and physiologically well tolerated carrier and possibly further suitable active, additional or auxiliary substances with a defined inhibitor dose, and is prepared in the desired form of administration.

In particular aspects, Response markers are, but are not limited to, proteins or RNA molecules or modifications of a nucleic acid (such as SNP or methylation), which are correlated with the cellular response of a cell to an exogenous substance, in particular a therapeutic substance. Different patients react in different ways to a specific therapy. This is based on the patient-individual cellular responses to a therapeutic substance. By a differential analysis of identical tissues of different persons, the persons suffering from the same disease and being treated with the same therapy, however reacting in different ways to the therapy (e.g. by healing processes of different speeds or different disadvantageous effects such as side effects), such response markers can be identified, and on the one hand the (differential) existence of a protein or enzyme or a modification of the nucleic acid, but also its absence will qualify it as a response marker.

In particular aspects, the term "confidence interval" refers to, but is not limited to, quantification of uncertainty in measurement. It is usually reported as percentage of confidence interval, which is the range of values within which one can be sure a certain percentage of likelihood that the true value for the whole population lies.

EXAMPLES

Example 1. Sample Collection

Example 1a. Collection of Plasma Samples

Plasma samples were collected from several Providers located in the US, Russia, Hungary, and Germany according to the following specifications:

Plasma samples from patients with stages I-III (AJCC) of colorectal cancer and various controls according to the following groups were collected:
CRC-Group: Patients with colorectal cancer (pathologically confirmed)
Healthy controls: Patients without pathological findings in colonoscopy and no signs of acute or exacerbated chronic disease
Cancer Controls: Patients with carcinomas other than colorectal cancer, e.g. breast or prostate carcinoma Non-Cancer Controls: Patients with non-cancerous diseases Table 2 and 3 give an overview of two collected sample sets:

TABLE 2 overview of a set of samples.

| Diagnosis Group | Sample volume | Number of samples | Remarks |
|---|---|---|---|
| Colorectal cancer | 16 ml of plasma | 175 | Stage I, II, III regardless of symptoms |
| Non-cancer controls | | 175 | Symptomatic patients with non-acute conditions |
| Cancer controls | | 50 | Predominantly prostate and breast cancer |

TABLE 3 overview of a second set of samples.

| Diagnosis Group | Sample Volume | Number of samples | Remarks |
|---|---|---|---|
| Colorectal cancer | 16 ml of plasma | 200 | Stage I, II, III and no CRC-specific symptoms |
| Healthy controls | | 125 | Asymptomatic patients |
| Non-cancer controls | | 175 | Symptomatic patients with non-acute conditions |
| Cancer controls | | 50 | Predominantly prostate and breast cancer |

In-/Exclusion Criteria for Samples:

An equivalent number of samples at minimum 30 samples were collected for each group. To enroll a plasma remote sample the following criteria must be fulfilled (Table 4-8):

TABLE 4

General criteria for plasma sample enrollment.
General criteria - applied to all samples

| | |
|---|---|
| Consent | Consent form explained and signed by patient (~45 ml of blood) |
| Infectious | Patient not known to have HIV, HBV or HCV |
| Age | Patient was preferably 50 years or older (40 years minimum) |
| Med. Record | Med. record available, |
| Enrollment | Disease group still eligible for study enrollment |

TABLE 5

Criteria for enrollment of plasma samples in the colorectal cancer group.
CRC-Group - Samples derived from patients with Colorectal Cancer (CRC)

| | |
|---|---|
| Timing | Patient still PRE-treatment, i.e. has not received any treatment including neoadjuvant and colonoscopy tumor removal |
| Pathology | Histological type: adenocarcinoma |
| Staging | Stage I-III according to AJCC |
| History | Patient has no history of colon cancer |
| Colonoscopy | Report including histological analysis from colonoscopy exists Colonoscopy not done within last 7 days or more than 6 months ago |

TABLE 6

Criteria for enrollment of plasma samples in the cancer control group.
Cancer Controls - samples derived from patients with e.g. breast and prostate cancer

| | |
|---|---|
| Timing | Patient still pre-treatment, i.e. before any cancer-related therapy |
| History | Patient has no history of colon cancer |
| Pathology | Histological diagnosis available |
| Staging Info | TNM classification data |
| Symptoms | Patients not colonoscopied for any of the following CRC-specific symptoms were the preferred target population for this group: anorectal bleeding (hematochezia) altered bowel habits obvious/known anemia with hemoglobin <10 g/dl unexplained weight loss (10% of weight in 6 months) signs of bowel obstruction (change in stool shape) altered bowel habits |

TABLE 7

Criteria for enrollment of plasma samples in the healthy control group.
Healthy controls - no sign of acute disease

| | |
|---|---|
| Timing | Patient in 'normal' situation (e.g. no general anesthesia, surgery etc.) |
| Pathology | Histological type: normal mucosa, no inflammation or other findings |
| History | No history of cancer in last 5 years (beside basal cell skin) |
| Colonoscopy | Report including histological analysis from colonoscopy exists Colonoscopy not done within last 7 days or more than 6 months ago |
| Symptoms | No signs or symptoms of acute disease No change in symptoms of existent chronic disease (exacerbation) |

TABLE 8

Criteria for enrollment of plasma samples in the non-cancer control group.
Non-cancer controls - acute infectious, inflammatory, systemic disease

| | |
|---|---|
| Timing | Disease is currently active, |
| History | No history of cancer in last 5 years (beside basal cell skin) |
| Colonoscopy | Colonoscopy only if disease was located in colon, e.g. diverticulitis Colonoscopy not done within last 7 days or more than 6 months ago |

Each principal investigator provided clinical patient information as specified by the Case Report Form included in the sample collection kit supplied for every patient. This included, but is not limited to:
General patient data: age, gender, race
Symptoms
Diagnosis info: current diseases including pathology report details
Treatment information Furthermore, each provider was provided a study protocol with a description of the collection process and sample collection kits to ensure the use of same material for blood draw, plasma extraction and storage of samples.

For each patient a sample collection kit with pre-labelled tubes and printed forms is used. In one large bag it contains the Case Report Form (CRF) for the clinical information and a Process Checklist to record processing steps. The material required for the blood draw (needles and blood containers), the plasma extraction (Falcon Tubes and pipettes) and the storage of samples (cryovials) is bundled in smaller bags.

After the primary investigator decided to enroll a patient, blood was drawn and the CRF was completed. Blood collection tubes were need to be filled above the mark printed on the label to ensure correct EDTA concentration in the sample.

The blood tubes were either processed immediately or were kept on cold packs for up to three hours, if needed to be shipped to the laboratory.

Plasma was extracted from the drawn blood by a two step centrifugation process. Both steps were performed at 1,500×g at 4 degree Celsius. Blood containers were used for the first spin. The supernatant was then carefully pipetted from the 4-5 blood collection tubes in two 15 ml Falcon tubes stopping 5 mm above the buffy coat.

After the second spin the plasma from the small Falcon tubes was transferred to a large 50 ml Falcon tube for pooling before being aliquoted in 4-5 4.5 ml cryovials. At this step a residual volume of 0.5 to 1 ml remained in each small Falcon tube to ensure optimum separation of white blood cells from supernatant.

Cryovials were frozen upright immediately and in no more than 4 hours from blood draw. Freezing and storage occurred at −70 to −80 degrees Celsius.

Each step was recorded on the Process Checklist provided with the collection kit.

Samples were shipped on dry ice upon request.

Information recorded was entered in an electronic spreadsheet and was provided as the CRFs and the process checklists for subsequent analysis of the plasma samples. The clinical data provided in the electronic spreadsheet was reviewed to ensure:
Plausibility
Completeness
Pseudonymization and
compliance with the in-and exclusion criteria.

Example 1b. Collection of Urine Samples

Urine samples were collected by several providers located in the US, and Germany.

Each Provider provided a study protocol with a description of the collection process and sample collection kits to ensure the use of same material for urine collection and storage of samples. Prior to starting the collection in-/exclusion criteria were determined.

For each patient a sample collection kit with pre-labelled tubes and printed forms is used. In one large bag it contains the Case Report Form (CRF) for the clinical information and a Process Checklist to record processing steps. The material required for the urine collection (urine containers, pipette) and the storage of samples (cryovials) is bundled in smaller bags.

After the primary investigator decided to enroll a patient, the patient's prostate was massaged and first 20 ml of urine was collected and the CRF completed. The urine collection cup was needed to be filled to the mark on the collection container to ensure correct EDTA concentration in the sample.

The urine is pipetted into two 10 ml cryovials and frozen at −70 to −80 degree Celsius within one hour after collection.

Each step was recorded on the Process Checklist provided with the collection kit.

Samples were shipped on dry ice upon request.

Information recorded was entered in an electronic spreadsheet and was provided as the CRFs and the process checklists for subsequent analysis of the urine samples.

Example 2. Process Controls

The following process controls were prepared and used.

MagNA Pure negative control: 5% BSA (Bovine Serum Albumin Fraction V (Roche Cat #03 117 375 001) diluted in 1× Phosphate Buffered Saline (10×PBS Buffer pH 7.4 (Ambion Inc. Cat #9625).

MagNA Pure positive Control: methylated DNA (Chemicon Cat # S7821) spiked into 5% BSA solution, final concentration 25 ng/ml.

The said controls were prepared in bulk prior to each study, and stored in 4 ml aliquots which is the sufficient volume for one run of the MagNA Pure LC instrument (Roche).

Example 3. DNA Isolation from Plasma Samples

DNA isolation from 895 plasma samples was performed using the MagNA Pure Compact Nucleic Acid Isolation Kit (I) Large Volume (Roche). Plasma samples were thawed. DNA was extracted in parallel from eight 1 ml aliquots of each plasma sample. The samples and controls were filled into a microtiter plate, handled and pooled according to FIG. 2. Each run of the MagNA Pure LC instrument includes 3 three samples each of 8 ml divided into 1 ml aliquots; a negative control of 4 ml divided into 1 ml aliquots; and a positive control of 4 ml divided into 1 ml aliquots. The position on the microtiter plate of the negative and positive controls was randomly assigned for each run at the outset of the study. An elution volume of 100 µl per well was selected. Using 4 MagNA Pure LC instruments, runs were set up and completed in pairs. The provided DNA in elution buffer was then subjected to the pooling and concentration step.

Example 4. Pooling and Concentration

Figure 2:
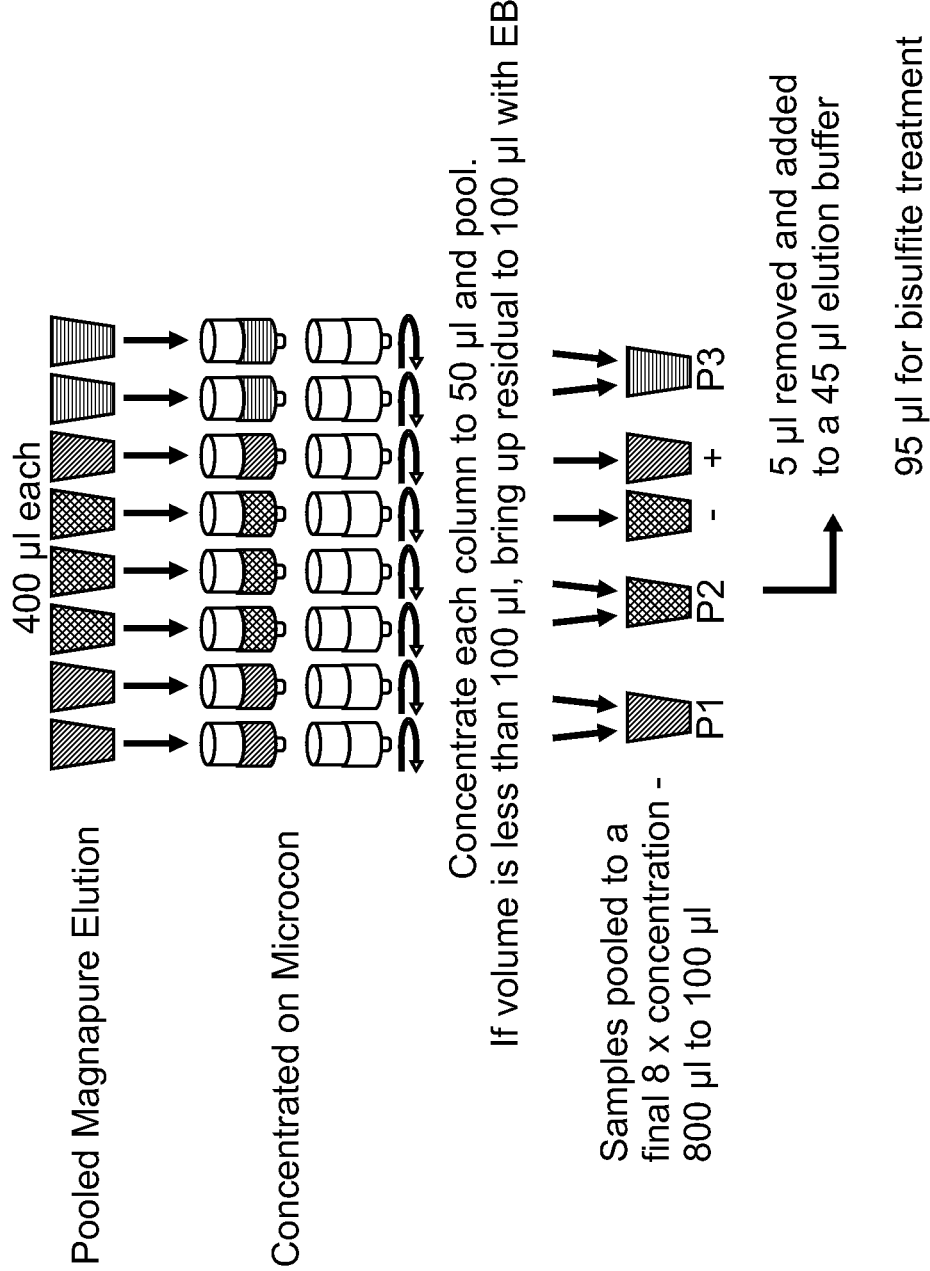
FIG. 2 shows an overview of an exemplary pooling and concentrating strategy.

The objective of this step was to pool the 8 DNA extractions performed in parallel for each remote sample and to concentrate the 800 µl eluate to a volume of 100 µl (see FIG. 2). According to the MagNA Pure Extraction protocol 100 µl of eluate were obtained for each 1 ml aliquote. Two Microcon YM-30 columns (Millipore) were used per remote sample. In other words, 4 eluates resulting in a volume of 400 µl were pooled on each filter. Subsequently the filters were centrifuged with a microcentrifuge until the volume is 50 µl. The two 50 µl concentrates were pooled, to provide a 100 µl sample comprising the DNA extracted from the 8 ml of plasma sample.

A single Microcon YM-30 column (Millipore) was used for the positive and negative controls. The resulting 50 µl of respective control was brought to 100 µl by addition of MagNA Pure Elution buffer provided by the MagNA Pure Compact Nucleic Acid Isolation Kit (I) Large Volume.

Example 5. Quality Control for DNA Extraction

5 µl were removed from each 100 µl of concentrated sample, positive control and negative control and were diluted in 45 µl of MagNA Pure Elution buffer provided by the MagNA Pure Compact Nucleic Acid Isolation Kit (I)

Large Volume. 12.5 µl of the diluted DNA were subjected to the CFF1 genomic DNA assay for determination of the concentration of the total DNA. The concentration of recovered DNA in the positive control samples was used as quality control measure to calibrate the DNA extraction step. The median DNA recovery for the positive controls was 2.8 ng/ml. The median DNA recovery from 895 plasma samples was 3.86 ng/ml, with a range of 0 to 1086 ng/ml.

CFF1 Genomic DNA Assay

```
CFF1 forward primer
                                      SEQ ID NO: 1
5'TAAGAGTAATAATGGATGGATGATG3'

CFF1 reverse primer
                                      SEQ ID NO: 2
5'CCTCCCATCTOCCTTCC3'

CFF1 TaqMan probe
                                      SEQ ID NO: 3
5'-6FAM-ATGGATGAAGAAAGAAAGGATGAGT-BHQ-1-3'
```

The following solutions were pipetted together and mixed according to Table 9.

TABLE 9

PCR mix preparation for CFF1 genomic DNA assay.
(Hybprobe Master Mix stands for the LightCycler FastStart DNA Master Hybridization Probes (Roche Cat# 2 239 272).)

| solution | Concentration of stock | volume | final concentration |
|---|---|---|---|
| Hybprobe Master Mix | 10x | 2 µl | 1x |
| MgCl$_2$ | 25 mmol/l | 1.2 µl | 2.500 mmol/l |
| Primer mixture | 10 µmol/l (each) | 1.25 µl | 0.625 µmol/l (each) |
| TaqMan probe | 10 µmol/l | 0.4 µl | 0.200 µmol/l (each) |
| water | — | 2.65 µl | — |
| Diluted DNA | — | 12.5 µl | — |
| Total react. volume | | 20 µl | |

The PCR was carried out in a LightCycler 2.0 PCR Machine (Roche) according to the conditions specified in Table 10.

TABLE 10

PCR cycling conditions for CFF1 genomic DNA assay at a LightCycler 2.0 PCR Machine (Roche).

| 1 | Activation | 95° C. | 10 min |
|---|---|---|---|
| 2 | Denaturation | 95° C. | 15 s |
| 3 | Annealing/extension and detection | 58° C. | 60 s |
| 5 | Cycling | Steps 2 to 3 were repeated 45 times | |
| 4 | Cooling | 40° C. | 30 s |

Example 6. Bisulfite Treatment and Purification of Bisulfite Treated DNA

The following devices were prepared: 50° C. water bath, 60° C. thermomixers, boiling water bath.

The following reagents were prepared: Prior to the start of the study, all dry bisulfite and radical scavenger reagents were weighed and aliquoted in each case into 75 tubes to provide 75 sets of aliquoted bisulfite treatment reagent. Each of the 75 sets is used for a batch of bisulfite treatment.

The bisulfite solution as well as the dioxane-radical scavenger solution was prepared fresh for each procedure. For the bisulfite solution, 10.36 g of sodium bisulfite and 2.49 g of sodium sulfite were dissolved by adding 22 ml of nuclease-free water. The solution was repeatedly rigorously mixed and incubated at 50° C. until all bisulfite particles were dissolved. For the dioxane-radical scavenger solution, 323 mg of 6-hydroxy-2,5,7,8-tetramethyl-chroman-2carboxylic acid (radical scavenger) were dissolved by adding 8.2 ml of 1,4-dioxane. The solution was rigorously mixed until all particles were dissolved. In addition, a 500 ml solution of 0.1 mol/l tris-(hydroxymethyl)-aminomethane 0.1 mmol/l EDTA, 50 ml of a 0.2 mol/l NaOH solution and 50 ml of a 0.1 mol/l NaOH solution were prepared.

Storage of samples: All samples were stored at 4° C.

Used Materials and Equipment:
Eppendorf Thermomixer 5355 (Brinkmann #022670107)
Eppendorf Thermomixer 2.0 ml block (Brinkmann #022670549)
VWR Water bath 1225 (VWR #13309-375)
VWR hotplate with stir 620, 7"×7" (VWR #12365-382)
Eppendorf Microcentrifuge 5417C
Mettler-Toledo Analytical Balance AG64
Millipore Y-30 Microcon Filter Devices (Millipore #42411)
Corning 4 L glass beaker (Corning #1003-4L)
Nalgene Graduated Cylinder 500 ml (NNI #3663-0500)
Nalgene Sterile 0.2 µM Filter unit, 500 ml (Nalgene #166-0020)
Nalgene floating microtube rack, 16 position (VWR #60986-098)
Nalgene floating microtube rack, 8 position (VWR #60986-099)
50 ml Falcon conical tube (Falcon 352070)
15 ml Falcon conical tube (Falcon 352096)
Nuclease free water (Ambion #9932)
Sodium Bisulfite (Sigma # S-9000)
Sodium Sulfite (Sigma #4672)
1,4-stabilized Dioxane (Sigma #33147)
Radical Scavenger-6-hydroxy-2,5,7,8-tetramethyl-chroman-2 carboxylic acid (Sigma #238813-5G)
0.5 mol/l EDTA (Ambion #9260G)
0.2 mol/l NaOH (Fisher # AC349685000)
1 mol/l tris-(hydroxymethyl)-aminomethane (Ambion #9855G)
Tube cap locks (ISC Bioexpress # C-3271-2)
Eppendorf Safe-Lock 2.0 ml Tubes (Eppendorf #22 60 004-4)
Column Collection Tube (Millipore #1065601)
Quik-Spin Minifuge (ISC Bioexpress # C-1301-P)
Portable Pipet-Aid (Drummond #4-000-100)
1.7 ml low-retention microcentrifuge tubes (ISC Bioexpress # C-3228-1)
0.65 ml low-retention microcentrifuge tubes (ISC Bioexpress # C-3226-1)

a) Bisulfite Treatment of Isolated DNA

Sample preparation: The 2 ml tubes containing the solution of isolated DNA of example 4 were removed from 4° C. Along with 20 samples of isolated DNA and process controls one positive control and one negative control for the bisulfite treatment were included in each batch of bisulfite treatment. The bisulfite negative control was MagNA Pure Elution buffer, while the bisulfite positive control contained 0.1 µg Chemicon Methylated DNA and 0.9 µg of Roche Human Genomic DNA per 1 ml of MagNA Pure Elution buffer.

The tubes were briefly centrifuged at 6,000 rpm. 354 µl of bisulfite solution and 146 µl of dioxane solution were added to each tube consecutively. The tubes were mixed rigorously for 10 s and centrifuged briefly at 6,000 rpm.

Bisulfite Reaction:

Tubes were locked and placed into a boiling water bath for 3 minutes to denature the DNA. Thereafter the tubes were transferred to the preheated thermomixer and incubated at 60° C. while mixing at 1,000 rpm for 30 min. After this the tubes were placed back into the boiling water bath for 3 min, before they were again incubated in the thermomixer for 1.5 h at 60° C. and 1,000 rpm. Subsequently, the tubes were placed back into the boiling water bath for 3 min, and incubated again in the thermomixer for 3 h at 60° C. and 1,000 rpm.

Desalting of Bisulfite Reaction Mixture:

The tubes of the bisulfite reaction were mixed and briefly centrifuged at 6,000 rpm. Precipitates formed during the heating were dissolved by repeatedly mixing and by the addition of 200 µl of water. Subsequently, the tubes were briefly centrifuged for 10 s. 400 µl of solution were removed from each tube an transferred to the corresponding appropriately labelled Micron YM-30 Microcon column. 1 column was used for each original remote sample, which was placed into a collection tube. The column assemblies were centrifuged for 20 min at 14,000×g. After centrifugation the column was transferred to a new collection tube and the remainder of about 400 µl of bisulfite reaction was transferred onto the corresponding Micron YM-30 Microcon column. Again, the column assemblies were centrifuged for 20 min at 14,000×g and the column was transferred to a new tube. After this second centrifugation, the filter membrane of the columns should look moist but there should be no visible volume of fluid. Columns with remaining liquid, were centrifuged repeatedly for 5 min at 14,000×g until the filter was just moist. Finally the columns are transferred into a new tube.

b) Purification of Bisulfite Treated DNA

Washing and Desulfonation of Bisulfite Treated DNA:

400 µl of 0.2 mol/l NaOH were transferred onto each just moist YM-30 Microcon column comprising a bisulfite treated DNA. The columns were centrifuged at 14,000×g for 12 min and then placed into a new tube. 400 µl of 0.1 mol/l NaOH were transferred onto each column and again centrifuged at 14,000×g for 12 min. After this second centrifugation, the filter membrane of the columns should look moist but there should be no visible volume of fluid. Columns with remained liquid, were centrifuged repeatedly for 5 min at 14,000×g until the filter was just moist. Finally the columns are transferred into a new tube. After this desulfonation step, columns were washed twice with 400 µl of water and subsequent centrifugation at 14,000×g for 12 min. A new tube for collecting the flow through was used for the second washing step. After the second washing, the filter membrane of the columns should look moist but there should be no visible volume of fluid. Columns with remained liquid, were centrifuged repeatedly for 5 min at 14,000×g until the filter was just moist. Columns with just moist were placed into a new tube for elution.

Elution of Bisulfite Treated DNA:

50 to 65 µl of pre-warmed 50° C. 0.1 mol/l Tris 0.1 mmol/l EDTA were transferred onto each column comprising the desulfonated DNA. Subsequently, the column assembly was placed in a thermomixer and incubated at 50° C. for 10 min while shaking at 1,000 rpm. Thereafter the columns were inverted and placed into a new labeled tube. The DNA is eluted from the respective column by centrifugation at 1,000×g for 7 min. Samples of eluted bisulfite treated DNA with a volume smaller than 50 µl were adjusted to 50 µl by the addition of the appropriate amount of 0.1 mol/l Tris 0.1 mmol/l EDTA.

For control purposes, 5 µl of the 50 µl of eluted DNA were diluted with 45 µl water. Thereof 12.5 µl were subjected to the HB14 assay for determination of the amount of bisulfite converted DNA and 20 µl for sulfite analysis. The median DNA recovery for 887 plasma samples was 3.32 ng/ml ranging from 0 to 1109 ng/ml.

HB14 assay (determination of the amount of bisulfite converted DNA):

```
HB14 forward primer
                                          SEQ ID NO: 4
5'-TGGTGATGGAGGAGGTTTAGTAAGT-3'

HB14 reverse primer
                                          SEQ ID NO: 5
5'-AACCAATAAAACCTACTCCTCCCTTAA-3'

HB14 TaqMan probe
                                          SEQ ID NO: 6
5'-FAM-ACCACCACCCAACACACAATAACAAACACA-BHQ1a-3'
```

The following solutions were pipetted together and mixed according to Table 11.

TABLE 11

PCR mix preparation for HB14 assay.
(Hybprobe Master Mix stands for the LightCycler FastStart DNA Master Hybridization Probes (Roche Cat# 2 239 272).)

| solution | Concentration of stock | volume | final concentration |
|---|---|---|---|
| Hybprobe Master Mix | 10x | 2 µl | 1x |
| MgCl$_2$ | 25 mmol/l | 1.6 µl | 3.000 mmol/l |
| Primer mixture | 10 µmol/l (each) | 1.8 µl | 0.900 µmol/l (each) |
| TaqMan probe | 10 µmol/l | 0.6 µl | 0.300 µmol/l (each) |
| water | — | 1.5 µl | — |
| bisulfite converted DNA | — | 12.5 µl | — |
| Total react. volume | | 20 µl | |

The PCR was carried out in a LightCycler 2.0 PCR machine (Roche) according to the conditions specified in Table 12.

TABLE 12

PCR cycling conditions for HB14 assay at a LightCycler 2.0 PCR machine (Roche).

| 1 | Activation | 95° C. | 10 min |
|---|---|---|---|
| 2 | Denaturation | 95° C. | 15 s |
| 3 | Annealing/extension and detection | 60° C. | 45 s |
| 5 | Cycling | Steps 2 to 3 were repeated 45 times | |
| 4 | Cooling | 40° C. | 30 s |

Sulfite Analysis:

Residual sulfite were measured in diluted bisulfite converted DNA samples using the Sulfite Cell Test (Merck Cat #1.14394.0001). A sulfite standard curve was prepared ranging from 100 mg/l to 0.78 mg/l sodium sulfite anhydrous ($Na_2SO_3$, M=126.04 g/mol) in 0.1 mol/l Tris 0.1 mmol/l EDTA. The detection-agent was prepared by placing one level grey micro-spoon (in the cap of the S03-1K bottle) of reagent into a reaction cell, close tightly and shake vigorously (or gently vortex 3 times for 5 s) until the reagent is completely dissolved.

Sulfite measurements were done in a 96 well plate. The final volume was 100 µl. To 30 µl of water in wells of a clear-bottom-plate, 20 µl of the diluted bisulfite converted DNA aliquot were added. For a standards, 50 µl of the sulfite-standards were pipetted into the clear-bottom-plate. Thereafter, 50 µl of the Merck sulfite-reagent were added to each well. For blank samples, 50 µl of water were added to 50 µl of the Merck sulfite-reagent. The plate was read at 412 nm on a Spectramax Plus Plate Reader (Molecular Devices). The data was analysed with SOFTMax PRO 4.0 software.

Example 7. Whole Genome Amplification of Bisulfite DNA

Example 7a. Whole Genome Amplification of Bisulfite DNA by Use of CircLigase ssDNA Ligase 15 µl of the bisulfite treated and purified DNA of example 6 are mixed with 2 µl of CircLigase 10× reaction buffer (Epicenter® Biotechnologies), 1 µl of 1 mmol/l ATP solution and 2 µl of 5 U/µl CircLigase ssDNA Ligase (Epicenter® Biotechnologies). The ligation mixture is incubated for 1 h at 60° C., before it is heated to 80° C. for 10 min to inactivate the ligase enzyme. After heating to 95° C. for 3 min it is stored on ice.

For amplification, 10 µl sample buffer of the TempliPhi™ DNA Sequencing Template Amplification Kit/TempliPhi™ 100/500 Amplification Kit (GE Healthcare) and a freshly prepared mixture of 18 µl reaction buffer of the TempliPhi™ Kit and 2 µl Phi29 DNA polymerase of the TempliPhi™ Kit are added to 10 µl of the ligation mixture. After incubation for 16 h at 30° C., the Phi29 DNA polymerase is inactivated by heating for 10 min at 65° C.

The amount of amplified bisulfite converted DNA can be determined according to the HB14 assay as described in example 6b. Therefore 10 µl of the inactivated amplification reaction mixture are mixed with 2.5 µl of water. This mixture is then applied into the HB14 assay. The efficiency of the whole genome amplification of bisulfite treated DNA can be determined by calculating the ratio of the determined concentration of bisulfite converted DNA after whole genome amplification to 15 times the determined concentration of bisulfite converted DNA before whole genome amplification (see example 6b). The factor 15 is thereby determined by the equivalent amount of eluted bisulfite converted DNA applied to the HB14 assay before the whole genome amplification and the equivalent amount of eluted bisulfite converted DNA applied to the HB14 assay after the whole genome amplification. If other volumes are used, a person skilled in the art knows how to calculate a corresponding factor.

The amount of total DNA is determined accordingly. Instead of the HB14 assay the CFF1 genomic DNA assay of example 5 is used. A person skilled in the art knows how to adjust the procedure for determination of the bisulfite converted DNA for the CFF1 genomic DNA assay. To verify that the ratio of original methylated to unmethylated DNA has not changed, an assay is performed which is specific for a defined methylation pattern. Such an assay is for example the HM 17378.71LC assay in example 8. Therefore equivalent amounts of bisulfite converted DNA before and after amplification are subject to a said assay. Here again, a person skilled in the art knows how to adjust accordingly the above specified procedure of the determination of the ratio of bisulfite converted DNA before and after amplification for determining the ratio of DNA representing a defined methylation pattern before and after whole genome amplification.

Example 7b. Whole Genome Amplification of Bisulfite DNA by Use of Terminal Nucleotidyl Transferase Overview:

For whole genome amplification of bisulfite converted DNA the following steps are carried out:
1. Fragmentation of the human DNA using DNA restriction enzymes.
2. Tailing (adding a poly-dA sequence) the 3' ends of the DNA fragments with terminal nucleotidyl transferase (TdT).
3. Conversion of all unmethylated cytosines into uracils by treatment with bisulfite and subsequent purification (including desulfonation).
4. Linear amplification of the bisulfite converted DNA by means of a primer extension reaction with primers complementary to the attached tail (poly-dT primers)
5. Quantification of the resulting DNA amount by means of real time PCR (CFF1 assay total amount DNA, HB14 assay amount of bisulfite converted DNA)

Realization:

The detailed experimental setup is depicted in Table 13. Six different reactions are performed comprising the use of the two different DNA restriction endonucleases StuI and BseRI as well as respective controls.

TABLE 13

Experimental setup.

| Step | Reaction no. | | | | | |
|---|---|---|---|---|---|---|
| | I | II | III | IV | V | VI |
| Fragmentation | StuI | StuI | BseRI | BseRI | x | x |
| Tailing | TdT + dATP | dATP | TdT + dATP | dATP | TdT + dATP | dATP |
| DNA conversion | bisulfite treatment and purification | | | | | |
| Amplification | primer extension reaction | | | | | |
| Quantification | real time PCR quantification | | | | | |

The single steps are performed according to the following conditions:
1. Fragmentation:

The enzymatic restriction of human genomic DNA (Roche) takes place in a total volume of 40 µl consisting of 1 µg DNA, 4 µl 10×NE Buffer 2 (New England Biolabs) and 5 units of the restriction enzymes StuI or BseRI, respectively. The negative controls (reactions V and VI) contain no restriction enzyme. The reactions are incubated for 2 hours at 37° C.

2. Tailing:

The tailing of the fragmented DNA with a poly-dA sequence is achieved using terminal nucleotidyl transferase (TdT, New England Biolabs) in the presence of dATP. Negative controls are not treated with TdT. The reaction takes place in a volume of 50 µl consisting of 40 µl of the fragmentation reaction, 1 µl 10×NE Buffer 4 (New England Biolabs), 0.25 mmol/l CoCl$_2$, 50 µmol/l dATP (Fermentas) and 2 units TdT (omitted in the respective negative controls (reactions II, IV and VI)). The mixtures are incubated 30 min at 37° C. and finally inactivated by heating to 70° C. for 10 min.

3. Bisulfite Conversion of DNA:

Unmethylated cytosines are converted to uracils according to embodiments and methods described herein. Whole reaction mixtures (each 50 µl) of the tailing reaction are subjected to the bisulfite treatment and purification (including desulfonation). After the bisulfite conversion the DNA is recovered in a volume of 50 µl.

4. Linear Amplification:

Whole genome amplification of the bisulfite DNA by a primer extension reaction is carried out in a volume of 50 µl containing 25 µl of the bisulfite converted DNA (as described in step 3.), 2 U Hotstar Taq polymerase (Qiagen), 25 pmol primer (dT$_{25}$), 1×PCR buffer (Qiagen), 0.2 mmol/l of each dNTP (Fermentas). Cycling is done using a Mastercycler (Eppendorf) with the following conditions: 15 min at 95° C. and 15 cycles at 96° C. for 1 min, 45° C. for 1 min and 72° C. for 5 min.

5. Real Time PCR Quantification:

The amplified bisulfite converted DNA (1 µl each) is subjected to quantitative real time PCR (GSTP1 gene assay) using a LightCycler 2.0 PCR machine (Roche). Reactions are performed in 20 µl volume using the LightCycler FastStart DNA Master Hybridization kit (Roche) containing 4 mmol/l MgCl2, 0.15 µmol/l of each detection probe (SEQ ID NO: 7 5'-GTTTAAGGTTAAGTTTGGGTGTTTGTA-Fluo-3' and SEQ ID NO: 8 5'-Red640-TTTTGTTTTGTGT-TAGGTTGTTTTTTAGG-Phosphate-3' and 0.3 µmol/l of each primer (forward primer SEQ ID NO: 9 5'-GGAGTG-GAGGAAATTGAGAT-3', reverse primer SEQ ID NO: 10 5'-CCACACAACAAATACTCAAAAC-3'). 40 cycles at 95° C. for 10 s, 56° C. for 30 S and 72° C. for 10 s are performed after initial incubation for 10 min at 95° C. Quantification is done in triplicates.

Results:

All reactions without TdT (reactions II, IV and VI) are expected to show no significant amplification of bisulfite converted DNA due to the absence of the tail which acts as the primer binding site. Due to a loss of approximately 20% during the bisulfite treatment and subsequent purification, these reactions yield 0.8 µg of bisulfite converted DNA. A slight amplification is expected in reaction mixture V comprising no restriction endonuclease but the terminal transferase. This is due to random fragmentation of the used human genomic DNA. These fragments act also as templates for the TdT and can subsequently be amplified. Assuming a loss of 20% during the bisulfite conversion and 90% efficiency of the linear amplification in each amplification cycle, the reaction mixtures I and III are expected to yield 10.8 µg of amplified bisulfite converted DNA.

DISCUSSION

The method for whole genome amplification by means of the terminal transferase is expected to be valuable to amplify bisulfite converted DNA up to approximately 10 fold. A higher amplification can be achieved by increasing the number of amplification cycles during the primer extension reactions.

Using poly-dT primers, this is limited due to the presence of several poly-dA and poly-dT sites within the human bisulfite genome. These sites might be amplified in an exponential manner (PCR), therefore hampering the linear amplification. This limitation can be circumvented by applying 5'-methylated dCTP (d5meCTP) in the tailing reaction and a poly-G primer in the amplification reaction. Since the resulting poly-5meC tails are unaffected by the bisulfite reaction, these tails represent the only possible primer binding sites for poly-G primers in the human bisulfite genome. Accordingly, a PCR amplification can be avoided. Another improvement of this method can be achieved using primer comprising the residual bases of the restriction endonuclease recognition site. This leads to an increased specificity of the primer again avoiding an unwanted PCR amplification.

Example 8. Quantification of the Methylation Pattern Defined by the HM 17378.71LC Assay For the quantification of a defined methylation pattern an assay suitable for measuring said methylation pattern was used. For example, such an assay is the HM 17378.71LC assay. Therefore 12.5 µl of the eluted bisulfite converted DNA of example 6 were subjected to the HM 17378.71LC assay. The 12.5 µl of eluted DNA of example 6 correspond the equivalent of 1.9 ml of original remote sample as subjected to example 2. Alternatively, also an equivalent amount of amplified bisulfite converted DNA of example 7 can be used. The assay was carried out in triplicates.

```
HM 17378.71LC assay
HM 17378.71LC TaqMan Flour LC Probe
                                    SEQ ID NO: 11
5'- GTtCGAAATGATtttATttAGtTGC-FL -3'

HM 17378.71LC TaqMan LC 640 Red Probe
                                    SEQ ID NO: 12
5'- LCred640-CGTTGAtCGCGGGGTtC-PH -3'

HM 17378.71LC forward primer
                                    SEQ ID NO: 13
5'-GtAGtAGttAGtttAGtAtttAttTT -3'

HM 17378.71LC reverse primer
                                    SEQ ID NO: 14
5'- CCCACCAaCCATCATaT -3'

HM 17378.71LC blocker oligonucleotide
                                    SEQ ID NO: 15
5'- CATCATaTCAaACCCCACAaTCAACACACAaC-INV -3'
(INV represents a inverted 3'end)
```

A small capital letter represents a bisulfite converted cytosine in the sequence of the named primers, probes and the blocker oligonucleotide.

The following solutions were pipetted together and mixed according to Table 14.

TABLE 14

PCR mix preparation for HM 17378.71LC assay.
(Hybprobe Master Mix stands for the LightCycler FastStart DNA Master Hybridization Probes (Roche Cat# 2 239 272).)

| solution | Concentration of stock | volume | final concentration |
| --- | --- | --- | --- |
| Hybprobe Master Mix | 10x | 2 µl | 1x |
| MgCl$_2$ | 25 mmol/l | 2 µl | 3.50 mmol/l |
| Primer mixture | 10 µmol/l (each) | 0.6 µl | 0.30 µmol/l (each) |

TABLE 14-continued

PCR mix preparation for HM 17378.71LC assay.
(Hybprobe Master Mix stands for the LightCycler FastStart DNA
Master Hybridization Probes (Roche Cat# 2 239 272).)

| solution | Concentration of stock | volume | final concentration |
|---|---|---|---|
| Blocker oligonucleotide | 100 µmol/l | 0.8 µl | 4.00 µmol/l |
| detection probe mixture | 10 µmol/l (each) | 0.3 µl | 0.15 µmol/l (each) |
| water | — | 1.8 µl | — |
| bisulfite converted DNA | — | 12.5 µl | — |
| Total react. volume | | 20 µl | |

The PCR was carried out in a LightCycler 2.0 PCR machine (Roche) according to the conditions specified in Table 15.

TABLE 15

PCR cycling conditions for HM 17378.71LC assay at a LightCycler 2.0 PCR machine (Roche).

| 1 | Activation | 95° C. | 10 min |
| 2 | Denaturation | 95° C. | 10 s |
| 3 | Annealing and detection | 56° C. | 30 s |
| 4 | Extension | 72° C. | 10 s |
| 5 | Cycling | Steps 2 to 4 were repeated 50 times | |
| 6 | Cooling | 40° C. | 30 s |

Example 9. Realization of a Study

Overview:

895 plasma samples were collected according to example 1a and analyzed according to the following: A workflow of examples 2 to 6 and 8 was performed in two studies. DNA was isolated from plasma samples, pooled and concentrated before it was bisulfite treated and purified. Subsequently, the bisulfite converted DNA was quantified according to the HB14 assay described in example 6. The methylation pattern defined by the HM17378.71LC assay was quantified (see example 7). The 90% limit of detection of the HM17278.71LC assay was estimated as 21 pg by a dilution series of methylated (SSS1 treated) DNA in a background of 50 ng blood DNA (Roche human genomic DNA). In the first study a 1.6 ml plasma equivalent of DNA was added per PCR reaction and each plasma sample run in duplicate. In the second study a 1.9 ml plasma equivalent of DNA was added per PCR reaction and run in triplicate. The complete workflow was carried out in batch format in parallel. Positive and negative control samples were run in each process step to determine fluctuations per process batch. Based on a process calibration phase, the MagNaPure extraction and bisulfite treatment steps were calibrated and batches in which control DNA concentrations were outside the range of 3 standard deviations were excluded from analysis.

Realization:

Each remote sample was processed within three days. On the first day DNA was isolated and concentrated. On the second day DNA was bisulfite treated and purified. Finally, on the third day a HM 17378.71LC assay in triplicates, a CFF1 genomic DNA assay, and a HB14 assay are carried out for a respective sample. Every day i) 12 MagNA Pure LC instrument runs were carried out with 4 instruments running three times in parallel and plates with eluted DNA were concentrated in pairs; ii) three batches of samples were subjected to bisulfite treatment and purification after bisulfite treatment, each batch comprising 20 samples of the MagNA Pure DNA isolation with one additional positive and one additional negative control (in total 66 samples including controls); and iii) five set of real-time PCR LightCycler runs were performed (1 set of CFF1 genomic DNA assay, 1 set of HB14 assay, and 3 sets of HM 17378.71LC assay).

Statistical Analysis:

Exemplary in the first study, the median DNA recovery for the positive controls was 2.8 ng/ml for DNA isolation. The corresponding median DNA recovery for 895 plasma samples was 3.86 ng/ml, with a range of 0 to 1086 ng/ml. For bisulfite treatment and purification, the median DNA recovery for 887 plasma samples was 3.32 ng/ml ranging from 0 to 1109 ng/ml.

The first study was designed to determine the optimal method of replicate aggregation and the threshold value (cut off value) for positive/negative classification. The second study was designed to validate the assay and classification rule using an independent sample set. Sample numbers were pre-determined to provide acceptable confidence intervals. In the first study duplicate analysis of methylation pattern defined by the HM17378.71LC assay was performed on each plasma sample. A sample was considered positive if both replicates were positive. Sensitivity and specificity on the data derived in the second study were computed by applying the threshold value (cut of value) determined in the first study. Because of the high specificity of the marker (threshold or cut off value for the HM17378.71LC assay) found in the first study, a qualitative threshold of 0 pg DNA comprising the methylation pattern defined by the HM17378.71LC assay was determined. In the second study, triplicate analysis was performed on each patient plasma sample. A sample was considered positive if at least 2 of the 3 replicates were positive. Amplification curves were analyzed automatically and also by two independent reviewers to validate true curves. Discrepancies were resolved by a third, independent reviewer.

Results:

The sensitivity was first determined in the first study and then in the second study. The results of the two studies are summarized by Table 16 and 17. Sensitivity in both studies ranged from 50 to 57% for detection of colorectal cancer. This results indicate that the marker defined by the HM17378.71LC assay and the selected threshold value (cut off value) is also highly specific (94-95%) in asymptomatic individuals over 50 years of age. Specificity was also high (92%) when patients with conditions such as gastritis, arthritis, respiratory infection and early stage cancers other than colorectal cancers were included. The marker was shown to detect colorectal cancer with similar sensitivity regardless of stage of progression or location of the lesion in the colon unlike fecal tests such as FOBT and iFOBT that have been shown to have a decreased sensitivity for both proximal colorectal cancers and early stage cancers.

Patient compliance and performance of current screening strategies limit the effectiveness of tests available on the market today. An easily administered blood-based test for early detection of colorectal cancer followed by colonoscopy for positive individuals has the potential to be a very effective tool for reducing mortality from this disease.

TABLE 16

Results of the first study.

| Group | Positives/Total Tested | % [95% CI] |
|---|---|---|
| CRC | 72/127 | 57 [47.66] |
| CRC Stage I | 3/11 | 27 [6.61] |
| CRC Stage II | 4/15 | 27 [8.55] |
| CRC Stage III | 35/59 | 59 [46.77] |
| CRC Stage IV | 27/36 | 75 [58.88] |
| Healthy | 10/233 | 4 [2.8] |
| All Controls | 28/365 | 8 [—] |

TABLE 17

Results of the second study.

| Group | # Positives/Total Tested | % [95% CI] |
|---|---|---|
| CRC | 104/209 | 50 [43.57] |
| CRC Stage I | 24/51 | 47 [33.62] |
| CRC Stage II | 29/65 | 45 [32.57] |
| CRC Stage III | 30/52 | 58 [43.71] |
| CRC Stage IV | 14/26 | 54 [33.73] |
| Healthy | 5/83 | 6 [2.14] |
| All Controls | 19/239 | 8 [5.12] |

The invention claimed is:

1. A method for determining the presence or absence of methylation of at least one cytosine, or a series of cytosines in cis, in human DNA of a blood sample, a plasma sample, a serum sample or a urine sample from a human individual, comprising:
   (a) providing the sample comprising human DNA,
   (b) isolating human DNA from the sample;
   (c) treating the isolated human DNA with bisulfite to produce bisulfite-treated sulfonated DNA;
   (d) heating the bisulfite-treated sulfonated DNA of step (c) to a temperature between 85° Celsius and 100° Celsius for between 3 minutes and 18 hours, thereby desulfonating the bisulfite-treated sulfonated DNA;
   (e) performing methylation specific amplification on the heated DNA of step (d) without any prior desulfonation step comprising an alkaline reagent, wherein the methylation specific amplification comprises steps of denaturation, annealing two or more primers and extension of the two or more primers; and
   (f) detecting the presence or absence of methylation of at least one cytosine, or a series of cytosines in cis when the amplified DNA of step (e) is amplified, thereby determining the presence or absence of methylation of at least one cytosine, or a series of cytosines in cis, in human DNA of the blood sample, the plasma sample, the serum sample or the urine sample from the human individual.

2. The method of claim 1, wherein said sample provided in step (a) is plasma, and the providing of the plasma sample comprises:
   (a) obtaining blood from a human individual;
   (b) adding EDTA (ethylene-diamine-tetra-acetic acid) to the blood and mixing and centrifuging to obtain plasma comprising human DNA;
   (c) transferring the plasma into a new container;
   (d) centrifuging the plasma;
   (e) transferring the re-centrifuged plasma into a new container;
   (f) cooling the plasma to a temperature of 0° Celsius to 10° Celsius; and
   (g) freezing, storing or transporting the plasma;
   wherein all of the steps (a) to (g) are performed within 8 hours.

3. The method of claim 1, wherein the sample provided in step (a) is urine and the providing of the urine sample comprises:
   (a) performing prostatic palpation, prostatic massage, or both from the middle of the prostate to the left side of the prostate, to the right side of the prostate or both for 10 seconds to 120 seconds;
   (b) collecting voided urine comprising human DNA;
   (c) adding EDTA to the urine; wherein the EDTA has a pH of 5.0, 6.0, 7.0, 7.5, 8.0, 8.5, 9.0, or 10;
   (d) cooling the urine to a temperature of 0° Celsius to 10° Celsius; and
   (e) freezing, storing or transporting the urine wherein steps (b) to (e) are performed within 120 minutes.

4. The method of claim 1, wherein said sample provided in step (a) is divided into different sub-samples subsequent to providing said sample, and/or wherein said sample provided in step (a) or at least one component of said sample is concentrated subsequent to providing said sample.

5. The method of claim 4, wherein the concentration comprises ultrafiltration.

6. The method of claim 1, wherein the isolation of human DNA in step (b) comprises: treating the sample with a protease; treating the sample with a chaotropic salt or a detergent; purifying and washing the human DNA.

7. The method of claim 1, wherein step (c) comprises: mixing of 10 to 250 µl of a solution comprising the human DNA with 45 to 75 µl of bisulfite solution, the bisulfite solution having a pH in the range of 5.45 to 5.50 comprising 4.83 to 4.93 mol/l hydrogen sulfite; and adding 5 to 500 µl of an organic radical scavenger solution, the organic radical scavenger solution comprising an organic solvent and 10 to 750 mmol/l of β-hydroxy-2,5,7,8-tetramethyl-chroman-2-carboxylic acid.

8. The method of claim 1, wherein after the heating of step (d) and prior to step (e) the heated DNA is cooled to a temperature between 0° Celsius and 80° Celsius.

\* \* \* \* \*